US011233960B2

(12) United States Patent
Talbert et al.

(10) Patent No.: US 11,233,960 B2
(45) Date of Patent: *Jan. 25, 2022

(54) FLUORESCENCE IMAGING WITH FIXED PATTERN NOISE CANCELLATION

(71) Applicant: Cilag GmbH International, Zug (CH)

(72) Inventors: Joshua D. Talbert, Salt Lake City, UT (US); Donald M. Wichern, Ogden, UT (US)

(73) Assignee: Cilag GmbH International

( * ) Notice: Subject to any disclaimer, the term of this patent is extended or adjusted under 35 U.S.C. 154(b) by 50 days.

This patent is subject to a terminal disclaimer.

(21) Appl. No.: 16/735,929

(22) Filed: Jan. 7, 2020

(65) Prior Publication Data

US 2020/0404201 A1    Dec. 24, 2020

Related U.S. Application Data

(60) Provisional application No. 62/864,218, filed on Jun. 20, 2019.

(51) Int. Cl.
*A61B 5/00* (2006.01)
*A61B 5/026* (2006.01)
(Continued)

(52) U.S. Cl.
CPC ........ *H04N 5/3655* (2013.01); *A61B 5/0071* (2013.01); *A61B 5/0084* (2013.01); *A61B 5/0261* (2013.01); *A61B 5/489* (2013.01); *A61B 5/4887* (2013.01); *A61B 5/4893* (2013.01); *A61B 5/7203* (2013.01); *G06T 5/002* (2013.01); *G06T 5/50* (2013.01); *G06T 7/0014* (2013.01); *G06T 11/60* (2013.01); *H04N 5/33* (2013.01); *H04N 13/239* (2018.05);
(Continued)

(58) Field of Classification Search
USPC .......................................... 348/45
See application file for complete search history.

(56) References Cited

U.S. PATENT DOCUMENTS 5,313,542 A   5/1994  Castonguay
5,318,024 A   6/1994  Kittrell et al.
(Continued)

FOREIGN PATENT DOCUMENTS

CN   111526775 A   8/2020
CN   111565620 A   8/2020
(Continued)

*Primary Examiner* — Patricia I Young
(74) *Attorney, Agent, or Firm* — Terrence J. Edwards; TechLaw Ventures, PLLC

(57) ABSTRACT

Fluorescence imaging with reduced fixed pattern noise is disclosed. A method includes actuating an emitter to emit a plurality of pulses of electromagnetic radiation and sensing reflected electromagnetic radiation resulting from the plurality of pulses of electromagnetic radiation with a pixel array of an image sensor. The method includes reducing fixed pattern noise in an exposure frame by subtracting a reference frame from the exposure frame. The method is such that at least a portion of the plurality of pulses of electromagnetic radiation emitted by the emitter comprises one or more of electromagnetic radiation having a wavelength from about 770 nm to about 790 nm or from about 795 nm to about 815 nm.

30 Claims, 29 Drawing Sheets

(51) Int. Cl.
  *G06T 11/60* (2006.01)
  *G06T 5/50* (2006.01)
  *G06T 7/00* (2017.01)
  *G16H 30/40* (2018.01)
  *H04N 13/214* (2018.01)
  *H04N 13/218* (2018.01)
  *H04N 13/239* (2018.01)
  *H04N 13/254* (2018.01)
  *H04N 13/257* (2018.01)
  *H04N 5/33* (2006.01)
  *H04N 5/365* (2011.01)
  *H04N 9/00* (2006.01)
  *G06T 5/00* (2006.01)

(52) U.S. Cl.
  CPC . *H04N 13/254* (2018.05); *G06T 2207/20224* (2013.01); *G06T 2207/30096* (2013.01); *G06T 2207/30101* (2013.01); *G16H 30/40* (2018.01)

(56) References Cited

U.S. PATENT DOCUMENTS

| | | | |
|---|---|---|---|
| 5,363,387 A | 11/1994 | Sinofsky | |
| 5,749,830 A | 5/1998 | Kaneko et al. | |
| 6,110,106 A | 8/2000 | MacKinnon et al. | |
| 6,236,879 B1 | 5/2001 | Konings | |
| 6,300,638 B1 | 10/2001 | Groger et al. | |
| 6,975,898 B2 | 12/2005 | Seibel | |
| 9,509,917 B2 | 11/2016 | Blanquart et al. | |
| 10,341,593 B2 * | 7/2019 | Blanquart | A61B 1/00009 |
| 2001/0000317 A1 | 4/2001 | Yoneya et al. | |
| 2002/0024605 A1 | 2/2002 | Merrill et al. | |
| 2002/0123666 A1 | 9/2002 | Matsumoto | |
| 2002/0158870 A1 | 10/2002 | Brunkhart et al. | |
| 2002/0161282 A1 | 10/2002 | Fulghum | |
| 2003/0100824 A1 | 5/2003 | Warren et al. | |
| 2004/0186351 A1 | 9/2004 | Imaizumi et al. | |
| 2004/0234152 A1 | 11/2004 | Liege et al. | |
| 2005/0020926 A1 | 1/2005 | Wiklof et al. | |
| 2005/0107808 A1 | 5/2005 | Evans et al. | |
| 2006/0069314 A1 | 3/2006 | Farr | |
| 2006/0239723 A1 | 10/2006 | Okuda et al. | |
| 2006/0276966 A1 | 12/2006 | Cotton et al. | |
| 2007/0016077 A1 | 1/2007 | Nakaoka et al. | |
| 2007/0046778 A1 * | 3/2007 | Ishihara | G01N 21/6456 348/68 |
| 2007/0081168 A1 | 4/2007 | Johnston | |
| 2007/0086495 A1 | 4/2007 | Sprague et al. | |
| 2007/0242330 A1 | 10/2007 | Rosman et al. | |
| 2007/0276234 A1 | 11/2007 | Shahidi | |
| 2008/0015446 A1 | 1/2008 | Mahmood et al. | |
| 2008/0058629 A1 | 3/2008 | Seibel et al. | |
| 2008/0081950 A1 | 4/2008 | Koenig et al. | |
| 2008/0177139 A1 | 7/2008 | Courtney et al. | |
| 2009/0067458 A1 | 3/2009 | Ji et al. | |
| 2009/0306478 A1 | 12/2009 | Mizuyoshi | |
| 2010/0049180 A1 | 2/2010 | Wells et al. | |
| 2010/0128109 A1 | 5/2010 | Banks | |
| 2010/0134605 A1 | 6/2010 | Demos et al. | |
| 2010/0261958 A1 | 10/2010 | Webb et al. | |
| 2010/0277087 A1 | 11/2010 | Ikeda | |
| 2011/0087212 A1 | 4/2011 | Aldridge et al. | |
| 2011/0196355 A1 | 8/2011 | Mitchell et al. | |
| 2011/0213252 A1 | 9/2011 | Fulghum | |
| 2011/0298933 A1 | 12/2011 | Yanowitz et al. | |
| 2011/0311142 A1 | 12/2011 | Robles-Kelly et al. | |
| 2012/0123205 A1 | 5/2012 | Nie et al. | |
| 2012/0294498 A1 | 11/2012 | Popovic | |
| 2013/0176395 A1 | 7/2013 | Kazakevich | |
| 2013/0296710 A1 | 11/2013 | Zuzak et al. | |
| 2014/0111623 A1 | 4/2014 | Zhao et al. | |
| 2014/0160259 A1 | 6/2014 | Blanquart et al. | |
| 2014/0160318 A1 | 6/2014 | Blanquart et al. | |
| 2014/0163319 A1 | 6/2014 | Blanquart et al. | |
| 2014/0201666 A1 | 7/2014 | Bedikian et al. | |
| 2014/0260260 A1 | 9/2014 | Morenko | |
| 2014/0267654 A1 | 9/2014 | Blanquart et al. | |
| 2014/0267656 A1 | 9/2014 | Blanquart | |
| 2014/0286093 A1 | 9/2014 | Abe et al. | |
| 2014/0300750 A1 | 10/2014 | Nagamune | |
| 2014/0336501 A1 | 11/2014 | Masumoto | |
| 2015/0073209 A1 | 3/2015 | Ikeda | |
| 2015/0119637 A1 | 4/2015 | Alvarez et al. | |
| 2015/0223733 A1 | 8/2015 | Al-Alusi | |
| 2015/0309284 A1 | 10/2015 | Kagawa et al. | |
| 2016/0006914 A1 | 1/2016 | Neumann | |
| 2016/0042513 A1 | 2/2016 | Yudovsky | |
| 2016/0062103 A1 | 3/2016 | Yang et al. | |
| 2016/0183775 A1 | 6/2016 | Blanquart et al. | |
| 2016/0195706 A1 | 7/2016 | Fujii | |
| 2016/0278678 A1 | 9/2016 | Valdes et al. | |
| 2017/0079724 A1 | 3/2017 | Yang et al. | |
| 2017/0214841 A1 * | 7/2017 | Blanquart | H04N 9/07 |
| 2017/0280029 A1 | 9/2017 | Steiner | |
| 2017/0280970 A1 | 10/2017 | Sartor et al. | |
| 2017/0360275 A1 | 12/2017 | Yoshizaki | |
| 2018/0000401 A1 | 1/2018 | Kang et al. | |
| 2018/0310828 A1 | 11/2018 | DiMaio et al. | |
| 2019/0125454 A1 | 5/2019 | Stokes et al. | |
| 2019/0154850 A1 | 5/2019 | Nishihara et al. | |
| 2019/0191974 A1 | 6/2019 | Talbert et al. | |
| 2019/0191975 A1 | 6/2019 | Talbert et al. | |
| 2019/0191976 A1 | 6/2019 | Talbert et al. | |
| 2019/0191978 A1 | 6/2019 | Talbert et al. | |
| 2019/0197712 A1 | 6/2019 | Talbert et al. | |
| 2020/0400570 A1 | 12/2020 | Talbert et al. | |
| 2020/0400572 A1 | 12/2020 | Talbert et al. | |
| 2020/0400825 A1 | 12/2020 | Talbert et al. | |
| 2020/0400826 A1 | 12/2020 | Talbert et al. | |
| 2020/0404131 A1 | 12/2020 | Talbert et al. | |
| 2020/0404201 A1 | 12/2020 | Talbert et al. | |
| 2020/0404202 A1 | 12/2020 | Talbert et al. | |

FOREIGN PATENT DOCUMENTS

| | | |
|---|---|---|
| CN | 111601536 A | 8/2020 |
| WO | 2014018951 A1 | 1/2014 |
| WO | 2015077493 A1 | 5/2015 |
| WO | 2017201093 A1 | 11/2017 |
| WO | 2017223206 A1 | 12/2017 |
| WO | 2018049215 A1 | 3/2018 |
| WO | 2019133736 A1 | 7/2019 |
| WO | 2019133737 A1 | 7/2019 |
| WO | 2019133739 A1 | 7/2019 |
| WO | 2019133741 A1 | 7/2019 |
| WO | 2019133750 A1 | 7/2019 |
| WO | 2019133753 A1 | 7/2019 |
| WO | 2020256972 A1 | 12/2020 |
| WO | 2020256975 A1 | 12/2020 |
| WO | 2020256976 A1 | 12/2020 |
| WO | 2020256977 A1 | 12/2020 |
| WO | 2020256978 A1 | 12/2020 |

* cited by examiner

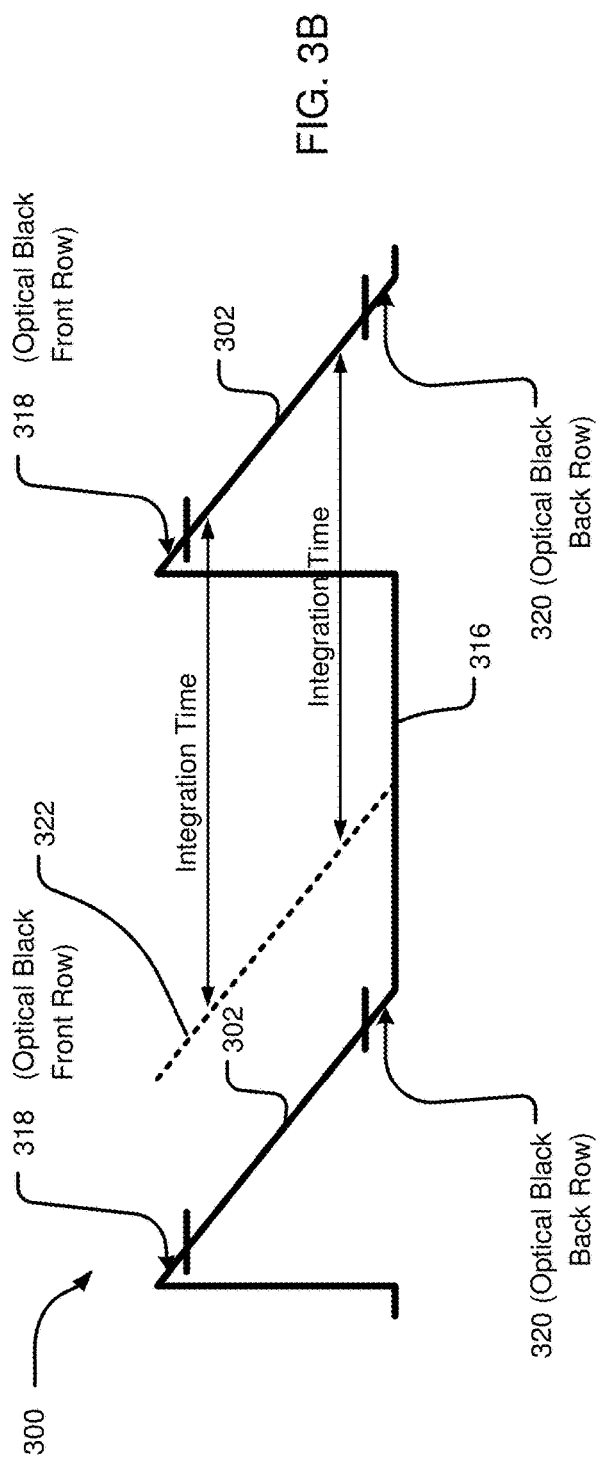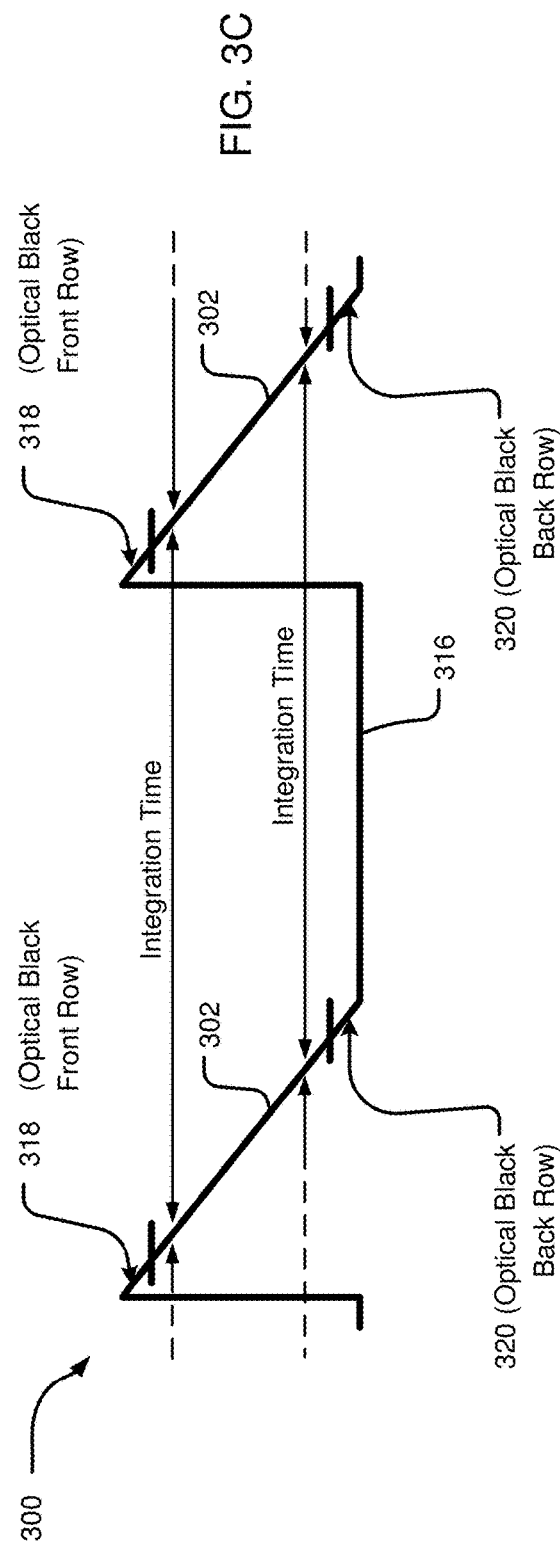

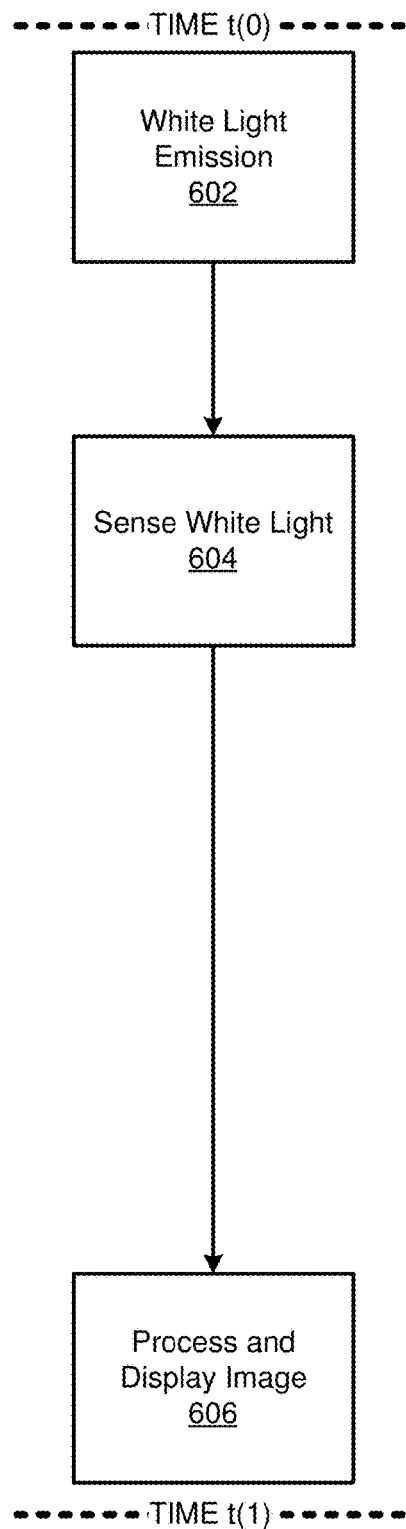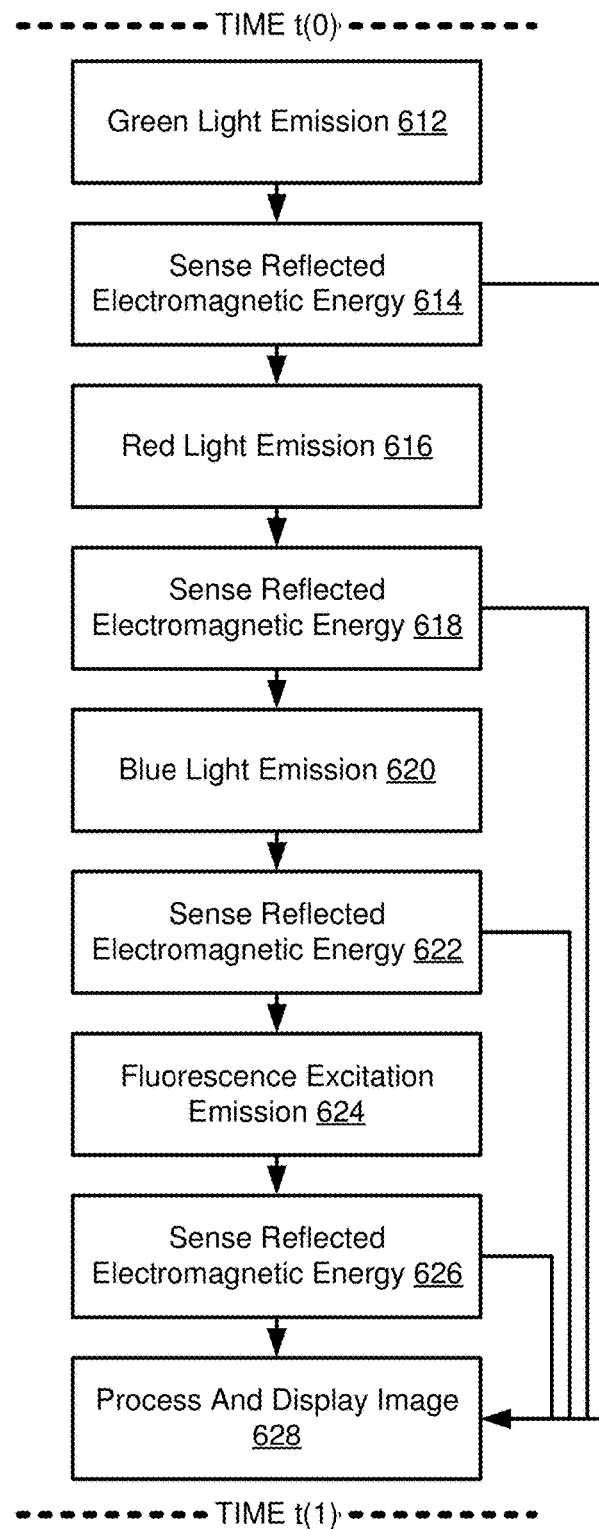
FIG. 6A
(Prior Art)
FIG. 6B

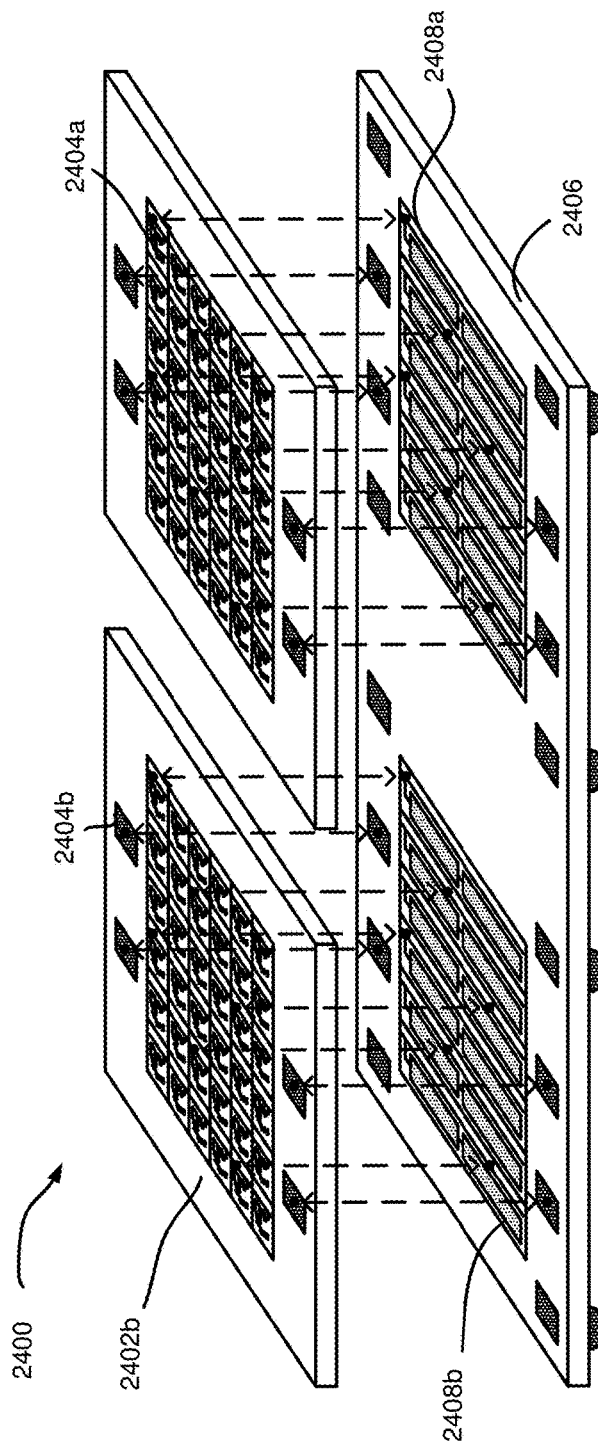
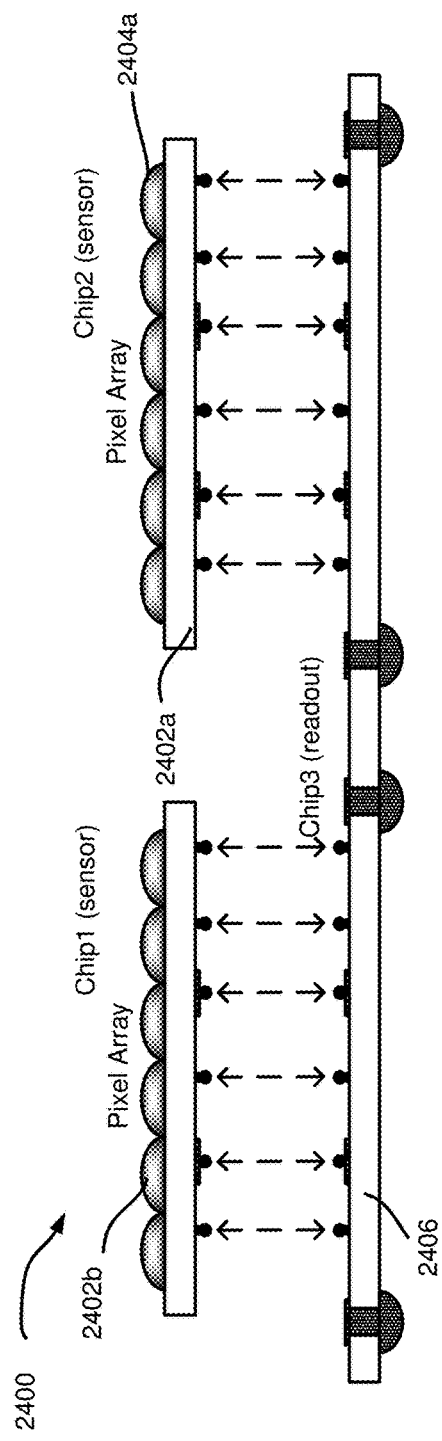
FIG. 24A
FIG. 24B 3D with double pixel array

FLUORESCENCE IMAGING WITH FIXED PATTERN NOISE CANCELLATION

CROSS-REFERENCE TO RELATED APPLICATIONS

This application claims the benefit of U.S. Provisional Patent Application No. 62/864,218, filed Jun. 20, 2019, titled "HYPERSPECTRAL AND FLUORESCENCE IMAGING WITH FIXED PATTERN NOISE CANCELLATION," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

This disclosure is directed to digital imaging and is particularly directed to fluorescence imaging in a light deficient environment.

BACKGROUND

Advances in technology have provided advances in imaging capabilities for medical use. An endoscope may be used to look inside a body and examine the interior of an organ or cavity of the body. Endoscopes are used for investigating a patient's symptoms, confirming a diagnosis, or providing medical treatment. A medical endoscope may be used for viewing a variety of body systems and parts such as the gastrointestinal tract, the respiratory tract, the urinary tract, the abdominal cavity, and so forth. Endoscopes may further be used for surgical procedures such as plastic surgery procedures, procedures performed on joints or bones, procedures performed on the neurological system, procedures performed within the abdominal cavity, and so forth.

In some instances of endoscopic imaging, it may be beneficial or necessary to view a space in color. A digital color image includes at least three layers, or "color channels," that cumulatively form an image with a range of hues. Each of the color channels measures the intensity and chrominance of light for a spectral band. Commonly, a digital color image includes a color channel for red, green, and blue spectral bands of light (this may be referred to as a Red Green Blue or RGB image). Each of the red, green, and blue color channels include brightness information for the red, green, or blue spectral band of light. The brightness information for the separate red, green, and blue layers are combined to create the color image. Because a color image is made up of separate layers, a conventional digital camera image sensor includes a color filter array that permits red, green, and blue visible light wavelengths to hit selected pixel sensors. Each individual pixel sensor element is made sensitive to red, green, or blue wavelengths and will only return image data for that wavelength. The image data from the total array of pixel sensors is combined to generate the RGB image. The at least three distinct types of pixel sensors consume significant physical space such that the complete pixel array cannot fit in the small distal end of an endoscope.

Because a traditional image sensor cannot fit in the distal end of an endoscope, the image sensor is traditionally located in a handpiece unit of an endoscope that is held by an endoscope operator and is not placed within the body cavity. In such an endoscope, light is transmitted along the length of the endoscope from the handpiece unit to the distal end of the endoscope. This configuration has significant limitations. Endoscopes with this configuration are delicate and can be easily misaligned or damaged when bumped or impacted during regular use. This can significantly degrade the quality of the images and necessitate that the endoscope be frequently repaired or replaced.

The traditional endoscope with the image sensor placed in the handpiece unit is further limited to capturing only color images. However, in some implementations, it may be desirable to capture images with fluorescence image data in addition to color image data. Fluorescence is the emission of light by a substance that has absorbed light or other electromagnetic radiation. Certain fluorescent materials "glow" or emit a distinct color that is visible to the human eye when the fluorescent material is subjected to ultraviolet light or other wavelengths of electromagnetic radiation. Certain fluorescent materials will cease to glow nearly immediately when the radiation source stops.

Fluorescence occurs when an orbital electron of a molecule, atom, or nanostructure is excited by light or other electromagnetic radiation, and then relaxes to its ground state by emitting a photon from the excited state. The specific frequencies of electromagnetic radiation that excite the orbital electron, or are emitted by the photon during relaxation, are dependent on the atom, molecule, or nanostructure. Fluorescence imaging has numerous practical applications, including mineralogy, gemology, medicine, spectroscopy for chemical sensors, detecting biological processes or signals, and others. Fluorescence can be used in biochemistry and medicine as a non-destructive means for tracking or analyzing biological molecules. Some fluorescent reagents or dyes can be configured to attach to certain types of tissue and thereby draw attention to that type of tissue.

However, fluorescence imaging requires specialized emissions of electromagnetic radiation and specialized imaging sensors capable of reading the specific relaxation wavelength for a specific fluorescent reagent. Different reagents or dyes are sensitive to different wavelengths of electromagnetic radiation and emit different wavelengths of electromagnetic radiation when fluoresced. A fluorescent imaging system may be highly specialized and tuned for a certain reagent or dye. Such imaging systems are useful for limited applications and are not capable of fluorescing more than one reagent or structure during a single imaging session. It is very costly to use multiple distinct imaging systems that are each configured for fluorescing a different reagent. Additionally, it may be desirable to administer multiple fluorescent reagents in a single imaging session and view the multiple reagents in a single overlaid image.

In light of the foregoing, described herein are systems, methods, and devices for fluorescent imaging in a light deficient environment. Such systems, methods, and devices may provide multiple datasets for identifying critical structures in a body and providing precise and valuable information about the body cavity.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified.

Advantages of the disclosure will become better understood with regard to the following description and accompanying drawings where:

FIGS. 3A to 3D are illustrations of the operational cycles of a sensor used to construct an exposure frame;

FIG. 6A is a schematic diagram of a process for recording a video with full spectrum light over a period of time from t(0) to t(1);

FIG. 6B is a schematic diagram of a process for recording a video by pulsing portioned spectrum light over a period of time from t(0) to t(1);

FIGS. 24A and 24B illustrate a perspective view and a side view, respectively, of an implementation of an imaging sensor having a plurality of pixel arrays for producing a three-dimensional image, wherein the plurality of pixel arrays and the image sensor are built on a plurality of substrates;

DETAILED DESCRIPTION

Figure 1:
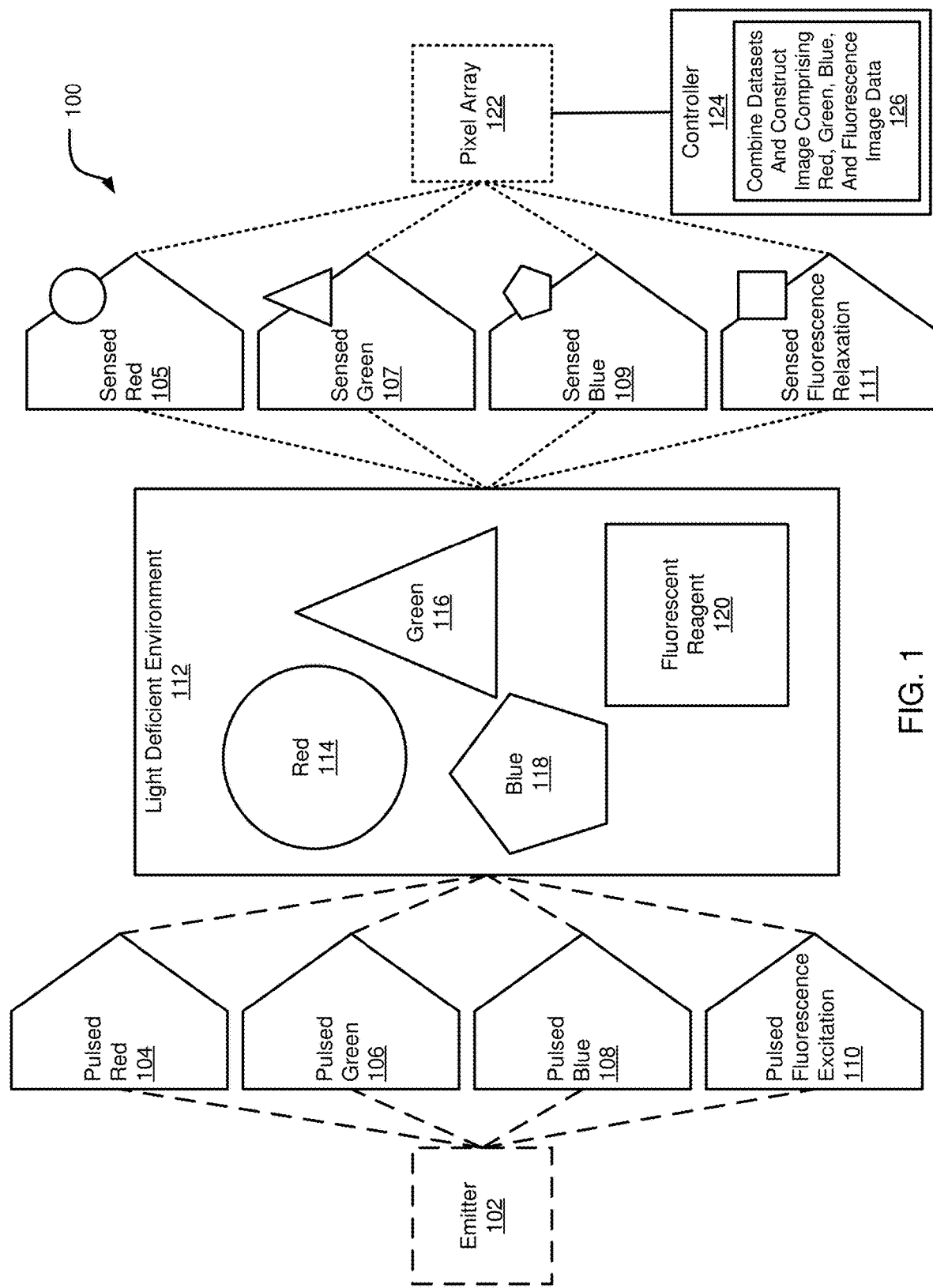
FIG. 1 is a schematic view of a system for digital imaging in a light deficient environment with a paired emitter and pixel array.

Disclosed herein are systems, methods, and devices for digital imaging that may be primarily suited to medical applications such as medical endoscopic imaging. An embodiment of the disclosure is an endoscopic system for fluorescence and/or color imaging in a light deficient environment.

An embodiment of the disclosure is an endoscopic imaging system with a CMOS (Complementary Metal Oxide Semiconductor) image sensor. CMOS image sensors suffer from multiple sources of image noise. Image noise is random variation of brightness or color information and can be caused by electronic noise. Image noise is generally undesirable and can degrade the quality of an image. Image noise can range from almost imperceptible specks on a digital image taken in good lighting conditions, to optical images that are almost entirely noise, from which only a small amount of information can be derived by sophisticated image processing. The amount of noise in an image generated by a CMOS image sensor is dependent on a wide range of physical conditions. Pure Poisson or Gaussian temporal noise with no coherent components such as photon shot noise or source follower read noise can look natural within a video stream. Other forms of perceivable noise will degrade image quality and may be unacceptable in some implementations.

One form of noise that can cause issues with CMOS image sensors is spatial noise (SN). Spatial noise has at least two sources, including pixel fixed pattern noise (pixel FPN) and column fixed pattern noise (column FPN). Pixel fixed pattern noise is mostly due to variations in photodiode leakage current (may be referred to as "dark signal") from pixel to pixel. This source can be dependent on junction temperature and exposure time. Column fixed pattern noise is a consequence of the readout architecture in which pixels from within the same column are channeled through common analog readout elements. In many implementations, it is desirable to cancel out image noise and particularly to cancel out fixed pattern noise. In light of the foregoing, disclosed herein are systems, methods, and devices for imaging in a light deficient environment and cancelling fixed pattern noise in resulting images.

Conventional endoscopes are designed such that the image sensor is placed at a proximal end of the device within a handpiece unit. This configuration requires that incident light travel the length of the endoscope by way of precisely coupled optical elements. The precise optical elements can easily be misaligned during regular use, and this can lead to image distortion or image loss. Embodiments of the disclosure place an image sensor within a distal end of the endoscope itself. This provides greater optical simplicity when compared with implementations known in the art. However, an acceptable solution to this approach is by no means trivial and introduces its own set of engineering challenges, not least of which that the image sensor must fit within a highly constrained area. Disclosed herein are systems, methods, and devices for digital imaging in a light deficient environment that employ minimal area image sensors and can be configured for fluorescence and color imaging.

In some instances, it is desirable to generate endoscopic imaging with multiple data types or multiple images overlaid on one another. For example, it may be desirable to generate an RGB image frame that further includes fluorescence imaging data overlaid on the RGB image frame. An overlaid image of this nature may enable a medical practitioner or computer program to identify critical body structures based on the fluorescence imaging data. Historically, this would require the use of multiple sensor systems including an image sensor for color imaging and one or more additional image sensors for fluorescence imaging. In such systems, the multiple image sensors would have multiple types of pixel sensors that are each sensitive to distinct ranges of electromagnetic radiation. In systems known in the art, this includes the three separate types of pixel sensors for generating an RGB color image along with additional pixel sensors for generating the fluorescence image data at different wavelengths of the electromagnetic spectrum. Traditionally, these multiple different pixel arrays consume a prohibitively large physical space and cannot be located at a distal tip of the endoscope. Considering the foregoing, disclosed herein are systems, methods, and devices for endoscopic imaging in a light deficient environment. The systems, methods, and devices disclosed herein provide means for employing multiple imaging techniques in a single imaging session while permitting one or more image sensors to be disposed in a distal tip of the endoscope.

Fluorescence Imaging

The systems, methods, and devices disclosed herein provide means for generating fluorescence imaging data in a light deficient environment. The fluorescence imaging data may be used to identify certain materials, tissues, components, or processes within a body cavity or other light deficient environment. In certain embodiments, fluorescence imaging is provided to a medical practitioner or computer-implemented program to enable the identification of certain structures or tissues within a body. Such fluorescence imaging data may be overlaid on black-and-white or RGB images to provide additional information and context.

Fluorescence is the emission of light by a substance that has absorbed light or other electromagnetic radiation. Certain fluorescent materials may "glow" or emit a distinct color that is visible to the human eye when the fluorescent material is subjected to ultraviolet light or other wavelengths of electromagnetic radiation. Certain fluorescent materials will cease to glow nearly immediately when the radiation source stops.

Fluorescence occurs when an orbital electron of a molecule, atom, or nanostructure is excited by light or other electromagnetic radiation, and then relaxes to its ground state by emitting a photon from the excited state. The specific frequencies of electromagnetic radiation that excite the orbital electron, or are emitted by the photon during relaxation, are dependent on the particular atom, molecule, or nanostructure. In most cases, the light emitted by the substance has a longer wavelength, and therefore lower energy, than the radiation that was absorbed by the substance. However, when the absorbed electromagnetic radiation is intense, it is possible for one electron to absorb two photons. This two-photon absorption can lead to emission of radiation having a shorter wavelength, and therefore higher energy, than the absorbed radiation. Additionally, the emitted radiation may also be the same wavelength as the absorbed radiation.

Fluorescence imaging has numerous practical applications, including mineralogy, gemology, medicine, spectroscopy for chemical sensors, detecting biological processes or signals, and so forth. Fluorescence may particularly be used in biochemistry and medicine as a non-destructive means for tracking or analyzing biological molecules. The biological molecules, including certain tissues or structures, may be tracked by analyzing the fluorescent emission of the biological molecules after being excited by a certain wavelength of electromagnetic radiation. However, relatively few cellular components are naturally fluorescent. In certain implementations, it may be desirable to visualize a certain tissue, structure, chemical process, or biological process that is not intrinsically fluorescent. In such an implementation, the body may be administered a dye or reagent that may include a molecule, protein, or quantum dot having fluorescent properties. The reagent or dye may then fluoresce after being excited by a certain wavelength of electromagnetic radiation. Different reagents or dyes may include different molecules, proteins, and/or quantum dots that will fluoresce at particular wavelengths of electromagnetic radiation. Thus, it may be necessary to excite the reagent or dye with a specialized band of electromagnetic radiation to achieve fluorescence and identify the desired tissue, structure, or process in the body.

Fluorescence imaging may provide valuable information in the medical field that may be used for diagnostic purposes and/or may be visualized in real-time during a medical procedure. Specialized reagents or dyes may be administered to a body to fluoresce certain tissues, structures, chemical processes, or biological processes. The fluorescence of the reagent or dye may highlight body structures such as blood vessels, nerves, particular organs, and so forth. Additionally, the fluorescence of the reagent or dye may highlight conditions or diseases such as cancerous cells or cells experiencing a certain biological or chemical process that may be associated with a condition or disease. The fluorescence imaging may be used in real-time by a medical practitioner or computer program for differentiating between, for example, cancerous and non-cancerous cells during a surgical tumor extraction. The fluorescence imaging may further be used as a non-destructive means for tracking and visualizing over time a condition in the body that would otherwise not be visible by the human eye or distinguishable in an RGB image.

The systems, methods, and devices for generating fluorescence imaging data may be used in coordination with reagents or dyes. Some reagents or dyes are known to attach to certain types of tissues and fluoresce at specific wavelengths of the electromagnetic spectrum. In an implementation, a reagent or dye is administered to a patient that is configured to fluoresce when activated by certain wavelengths of light. The endoscopic imaging system disclosed herein is used to excite and fluoresce the reagent or dye. The fluorescence of the reagent or dye is captured by the endoscopic imaging system to aid in the identification of tissues or structures in the body cavity. In an implementation, a patient is administered a plurality of reagents or dyes that are each configured to fluoresce at different wavelengths and/or provide an indication of different structures, tissues, chemical reactions, biological processes, and so forth. In such an implementation, the endoscopic imaging system emits each of the applicable wavelengths to fluoresce each of the applicable reagents or dyes. This may negate the need to perform individual imaging procedures for each of the plurality of reagents or dyes.

Imaging reagents can enhance imaging capabilities in pharmaceutical, medical, biotechnology, diagnostic, and medical procedure industries. Many imaging techniques such as X-ray, computer tomography (CT), ultrasound, magnetic resonance imaging (MRI), and nuclear medicine, mainly analyze anatomy and morphology and are unable to detect changes at the molecular level. Fluorescent reagents, dyes, and probes, including quantum dot nanoparticles and fluorescent proteins, assist medical imaging technologies by providing additional information about certain tissues, structures, chemical processes, and/or biological processes that are present within the imaging region. Imaging using fluorescent reagents enables cell tracking and/or the tracking of certain molecular biomarkers. Fluorescent reagents may be applied for imaging cancer, infection, inflammation, stem cell biology, and others. Numerous fluorescent reagents and dyes are being developed and applied for visualizing and tracking biological processes in a non-destructive manner. Such fluorescent reagents may be excited by a certain wavelength or band of wavelengths of electromagnetic radiation. Similarly, those fluorescent reagents may emit relaxation energy at a certain wavelength or band of wavelengths when fluorescing, and the emitted relaxation energy may be read by a sensor to determine the location and/or boundaries of the reagent or dye.

In an embodiment of the disclosure, an endoscopic imaging system pulses electromagnetic radiation for exciting an electron in a fluorescent reagent or dye. The endoscopic imaging system may pulse multiple different wavelengths of electromagnetic radiation for fluorescing multiple different reagents or dyes during a single imaging session. The endoscope includes an image sensor that is sensitive to the relaxation wavelength(s) of the one or more reagents or dyes. The imaging data generated by the image sensor can be used to identify a location and boundary of the one or more reagents or dyes. The endoscope system may further pulse electromagnetic radiation in red, green, and blue bands of visible light such that the fluorescence imaging can be overlaid on an RGB video stream.

Pulsed Imaging

Some implementations of the disclosure include aspects of a combined sensor and system design that allows for high definition imaging with reduced pixel counts in a controlled illumination environment. This is accomplished with frame-by-frame pulsing of a single-color wavelength and switching or alternating each frame between a single, different color wavelength using a controlled light source in conjunction with high frame capture rates and a specially designed corresponding monochromatic sensor. Additionally, electromagnetic radiation outside the visible light spectrum may be pulsed to enable the generation of a fluorescence image. The pixels may be color agnostic such that each pixel generates data for each pulse of electromagnetic radiation, including pulses for red, green, and blue visible light wavelengths along with other wavelengths used for fluorescence imaging.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems and methods for producing an image in a light deficient environment are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA) thereon to filter the incoming electromagnetic radiation into its separate components. In the visual range of the electromagnetic spectrum, such a CFA may be built on a Bayer pattern or modification thereon to separate green, red and blue spectrum components of the light.

As used herein, monochromatic sensor refers to an unfiltered imaging sensor. Since the pixels are color agnostic, the effective spatial resolution is appreciably higher than for their color (typically Bayer-pattern filtered) counterparts in conventional single-sensor cameras. Monochromatic sensors may also have higher quantum efficiency because fewer incident photons are wasted between individual pixels.

As used herein, an emitter is a device that is capable of generating and emitting electromagnetic pulses. Various embodiments of emitters may be configured to emit pulses and have very specific frequencies or ranges of frequencies from within the entire electromagnetic spectrum. Pulses may comprise wavelengths from the visible and non-visible ranges. An emitter may be cycled on and off to produce a pulse or may produce a pulse with a shutter mechanism. An emitter may have variable power output levels or may be controlled with a secondary device such as an aperture or filter. An emitter may emit broad spectrum or full spectrum electromagnetic radiation that may produce pulses through color filtering or shuttering. An emitter may comprise a plurality of electromagnetic sources that act individually or in concert.

It should be noted that as used herein the term "light" is both a particle and a wavelength and is intended to denote electromagnetic radiation that is detectable by a pixel array 122 and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

Referring now to the figures, FIG. 1 illustrates a schematic diagram of a system 100 for sequential pulsed imaging in a light deficient environment. The system 100 can be deployed to generate an RGB image with fluorescence imaging data overlaid on the RGB image. The system 100 includes an emitter 102 and a pixel array 122. The emitter 102 pulses a partition of electromagnetic radiation in the light deficient environment 112 and the pixel array 122 senses instances of reflected electromagnetic radiation. The emitter 102 and the pixel array 122 work in sequence such that one or more pulses of a partition of electromagnetic radiation results in image data sensed by the pixel array 122.

It should be noted that as used herein the term "light" is both a particle and a wavelength and is intended to denote electromagnetic radiation that is detectable by a pixel array 122 and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

A pixel array 122 of an image sensor may be paired with the emitter 102 electronically, such that the emitter 102 and the pixel array 122 are synced during operation for both receiving the emissions and for the adjustments made within the system. The emitter 102 may be tuned to emit electromagnetic radiation in the form of a laser, which may be pulsed to illuminate a light deficient environment 112. The emitter 102 may pulse at an interval that corresponds to the operation and functionality of the pixel array 122. The emitter 102 may pulse light in a plurality of electromagnetic partitions such that the pixel array receives electromagnetic energy and produces a dataset that corresponds in time with each specific electromagnetic partition. For example, FIG. 1 illustrates an implementation wherein the emitter 102 emits four different partitions of electromagnetic radiation, including red 104, green 106, blue 108, and a fluorescence excitation 110 wavelength. The fluorescence excitation 110 wavelength may include a plurality of different partitions of electromagnetic radiation that are selected to fluoresce a plurality of fluorescent reagents that are present within the light deficient environment 112. The fluorescent excitation 110 wavelength may be selected to fluoresce a particular fluorescent reagent that is present in the light deficient environment 112.

The light deficient environment 112 includes structures, tissues, and other elements that reflect a combination of red 114, green 116, and/or blue 118 light. A structure that is perceived as being red 114 will reflect back pulsed red 104 light. The reflection off the red structure results in sensed red 105 by the pixel array 122 following the pulsed red 104 emission. The data sensed by the pixel array 122 results in a red exposure frame. A structure that is perceived as being green 116 will reflect back pulsed green 106 light. The reflection off the green structure results in sensed green 107 by the pixel array 122 following the pulsed green 106 emission. The data sensed by the pixel array 122 results in a green exposure frame. A structure that is perceived as being blue 118 will reflect back pulsed blue 108 light. The reflection off the blue structure results in sensed blue 109 by the pixel array 122 following the pulsed blue 108 emission. The data sensed by the pixel array 122 results in a blue exposure frame.

When a structure is a combination of colors, the structure will reflect back a combination of the pulsed red 104, pulsed green 106, and/or pulsed blue 108 emissions. For example, a structure that is perceived as being purple will reflect back light from the pulsed red 104 and pulsed blue 108 emissions. The resulting data sensed by the pixel array 122 will indicate that light was reflected in the same region following the pulsed red 104 and pulsed blue 108 emissions. When the resultant red exposure frame and blue exposure frames are combined to form the RGB image frame, the RGB image frame will indicate that the structure is purple.

In an embodiment where the light deficient environment 112 includes a fluorescent reagent or dye or includes one or more fluorescent structures, tissues, or other elements, the pulsing scheme may include the emission of a certain fluorescence excitation wavelength. The certain fluorescence excitation wavelength may be selected to fluoresce a known fluorescent reagent, dye, or other structure. The fluorescent structure will be sensitive to the fluorescence excitation wavelength and will emit a fluorescence relaxation wavelength. The fluorescence relaxation wavelength will be sensed by the pixel array 122 following the emission of the fluorescence excitation wavelength. The data sensed by the pixel array 122 results in a fluorescence exposure frame. The fluorescence exposure frame may be combined with multiple other exposure frames to form an image frame. The data in the fluorescence exposure frame may be overlaid on an RGB image frame that includes data from a red exposure frame, a green exposure frame, and a blue exposure frame.

In an embodiment where the light deficient environment 112 includes structures, tissues, or other materials that emit a spectral response to certain partitions of the electromagnetic spectrum, the pulsing scheme may include the emission of a hyperspectral partition of electromagnetic radiation for the purpose of eliciting the spectral response from the structures, tissues, or other materials present in the light deficient environment 112. The spectral response includes the emission or reflection of certain wavelengths of electromagnetic radiation. The spectral response can be sensed by the pixel array 122 and result in a hyperspectral exposure frame. The hyperspectral exposure frame may be combined with multiple other exposure frames to form an image frame. The data in the hyperspectral exposure frame may be overlaid on an RGB image frame that includes data from a red exposure frame, a green exposure frame, and a blue exposure frame.

In an embodiment, the pulsing scheme includes the emission of a laser mapping or tool tracking pattern. The reflected electromagnetic radiation sensed by the pixel array 122 following the emission of the laser mapping or tool tracking pattern results in a laser mapping exposure frame. The data in the laser mapping exposure frame may be provided to a corresponding system to identify, for example, distances between tools present in the light deficient environment 112, a three-dimensional surface topology of a scene in the light deficient environment 112, distances, dimensions, or positions of structures or objects within the scene, and so forth. This data may be overlaid on an RGB image frame or otherwise provided to a user of the system.

The emitter 102 may be a laser emitter that is capable of emitting pulsed red 104 light for generating sensed red 105 data for identifying red 114 elements within the light deficient environment 112. The emitter 102 is further capable of emitting pulsed green 106 light for generating sensed green 107 data for identifying green 116 elements within the light deficient environment. The emitter 102 is further capable of emitting pulsed blue 108 light for generating sensed blue 109 data for identifying blue 118 elements within the light deficient environment. The emitter 102 is further capable of emitting pulsed fluorescence excitation 110 wavelength(s) of electromagnetic radiation for identifying a fluorescent reagent 120 within the light deficient environment 112. The fluorescent reagent 120 is identified by exciting the fluorescent reagent 120 with the pulsed fluorescence excitation 110 light and then sensing (by the pixel array 122) the fluorescence relaxation 111 wavelength for that particular fluorescent reagent 120. The emitter 102 is capable of emitting the pulsed red 104, pulsed green 106, pulsed blue 108, and pulsed fluorescence excitation 110 wavelengths in any desired sequence.

The pixel array 122 senses reflected electromagnetic radiation. Each of the sensed red 105, the sensed green 107, the sensed blue 109, and the sensed fluorescence relaxation 111 data can be referred to as an "exposure frame." Each exposure frame is assigned a specific color or wavelength partition, wherein the assignment is based on the timing of the pulsed color or wavelength partition from the emitter 102. The exposure frame in combination with the assigned specific color or wavelength partition may be referred to as a dataset. Even though the pixels 122 are not color-dedicated, they can be assigned a color for any given dataset based on a priori information about the emitter.

For example, during operation, after pulsed red 104 light is pulsed in the light deficient environment 112, the pixel array 122 senses reflected electromagnetic radiation. The reflected electromagnetic radiation results in an exposure frame, and the exposure frame is catalogued as sensed red 105 data because it corresponds in time with the pulsed red 104 light. The exposure frame in combination with an indication that it corresponds in time with the pulsed red 104 light is the "dataset." This is repeated for each partition of electromagnetic radiation emitted by the emitter 102. The data created by the pixel array 122 includes the sensed red 105 exposure frame identifying red 114 components in the light deficient environment and corresponding in time with the pulsed red 104 light. The data further includes the sensed green 107 exposure frame identifying green 116 components in the light deficient environment and corresponding in time with the pulsed green 106 light. The data further includes the sensed blue 109 exposure frame identifying blue 118 components in the light deficient environment and corresponding in time with the pulsed blue 108 light. The data further includes the sensed fluorescence relaxation 111 exposure frame identifying the fluorescent reagent 120 and corresponding in time with the pulsed fluorescence excitation 110 wavelength(s) of light.

In one embodiment, three datasets representing RED, GREEN and BLUE electromagnetic pulses are combined to form a single image frame. Thus, the information in a red exposure frame, a green exposure frame, and a blue exposure frame are combined to form a single RGB image frame. One or more additional datasets representing other wavelength partitions may be overlaid on the single RGB image frame. The one or more additional datasets may represent, for example, fluorescence imaging responsive to the pulsed excitation 110 wavelength between 770 nm and 790 nm and between 795 nm and 815 nm.

It will be appreciated that the disclosure is not limited to any particular color combination or any particular electromagnetic partition, and that any color combination or any electromagnetic partition may be used in place of RED, GREEN and BLUE, such as Cyan, Magenta and Yellow; Ultraviolet; infrared; any combination of the foregoing, or any other color combination, including all visible and non-visible wavelengths, without departing from the scope of the disclosure. In the figure, the light deficient environment 112 to be imaged includes red 114, green 116, and blue 118 portions, and further includes a fluorescent reagent 120. As illustrated in the figure, the reflected light from the electromagnetic pulses only contains the data for the portion of the object having the specific color that corresponds to the pulsed color partition. Those separate color (or color interval) datasets can then be used to reconstruct the image by combining the datasets at 126. The information in each of the multiple exposure frames (i.e., the multiple datasets) may be combined by a controller 124, a control unit, a camera control unit, the image sensor, an image signal processing pipeline, or some other computing resource that is configurable to process the multiple exposure frames and combine the datasets at 126. The datasets may be combined to generate the single image frame within the endoscope unit itself or offsite by some other processing resource.

Figure 2:
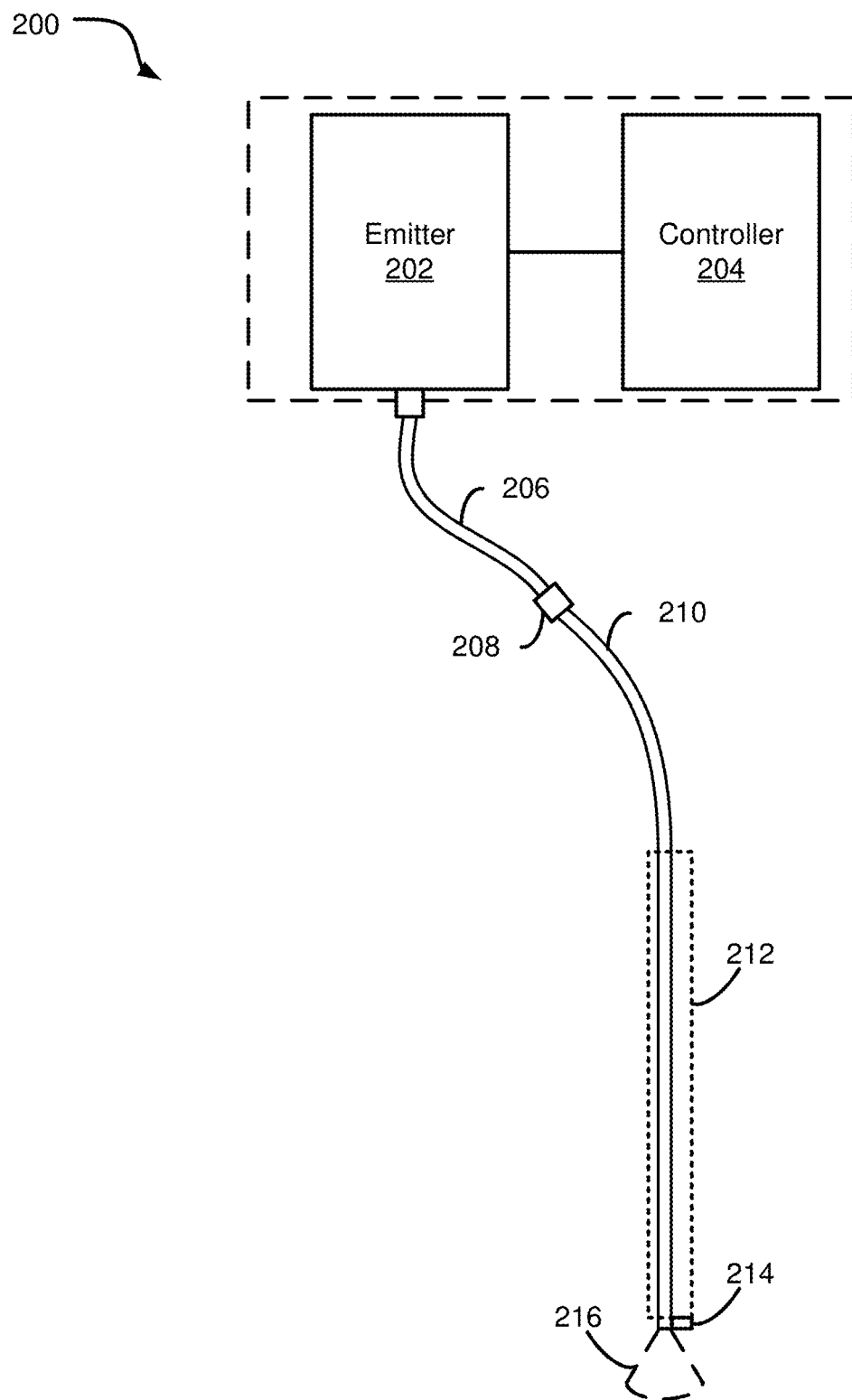
FIG. 2 is a system for providing illumination to a light deficient environment for endoscopic imaging.

FIG. 2 is a system 200 for providing illumination to a light deficient environment, such as for endoscopic imaging. The system 200 may be used in combination with any of the systems, methods, or devices disclosed herein. The system 200 includes an emitter 202, a controller 204, a jumper waveguide 206, a waveguide connector 208, a lumen waveguide 210, a lumen 212, and an image sensor 214 with accompanying optical components (such as a lens). The emitter 202 (may be generically referred to as a "light source") generates light that travels through the jumper waveguide 206 and the lumen waveguide 210 to illuminate a scene at a distal end of the lumen 212. The emitter 202 may be used to emit any wavelength of electromagnetic energy including visible wavelengths, infrared, ultraviolet, hyperspectral, fluorescence excitation, laser scanning pulsing schemes, or other wavelengths. The lumen 212 may be inserted into a patient's body for imaging, such as during a procedure or examination. The light is output as illustrated by dashed lines 216. A scene illuminated by the light may be captured using the image sensor 214 and displayed for a doctor or some other medical personnel. The controller 204 may provide control signals to the emitter 202 to control when illumination is provided to a scene. In one embodiment, the emitter 202 and controller 204 are located within a camera control unit (CCU) or external console to which an endoscope is connected. If the image sensor 214 includes a CMOS sensor, light may be periodically provided to the scene in a series of illumination pulses between readout periods of the image sensor 214 during what is known as a blanking period. Thus, the light may be pulsed in a controlled manner to avoid overlapping into readout periods of the image pixels in a pixel array of the image sensor 214.

In one embodiment, the lumen waveguide 210 includes one or more optical fibers. The optical fibers may be made of a low-cost material, such as plastic to allow for disposal of the lumen waveguide 210 and/or other portions of an endoscope. In one embodiment, the lumen waveguide 210 is a single glass fiber having a diameter of 500 microns. The jumper waveguide 206 may be permanently attached to the emitter 202. For example, a jumper waveguide 206 may receive light from an emitter within the emitter 202 and provide that light to the lumen waveguide 210 at the location of the connector 208. In one embodiment, the jumper waveguide 106 includes one or more glass fibers. The jumper waveguide may include any other type of waveguide for guiding light to the lumen waveguide 210. The connector 208 may selectively couple the jumper waveguide 206 to the lumen waveguide 210 and allow light within the jumper waveguide 206 to pass to the lumen waveguide 210. In one embodiment, the lumen waveguide 210 is directly coupled to a light source without any intervening jumper waveguide 206.

The image sensor 214 includes a pixel array. In an embodiment, the image sensor 214 includes two or more pixel arrays for generating a three-dimensional image. The image sensor 214 may constitute two more image sensors that each have an independent pixel array and can operate independent of one another. The pixel array of the image sensor 214 includes active pixels and optical black ("OB") or optically blind pixels. The active pixels may be clear "color agnostic" pixels that are capable of sensing imaging data for any wavelength of electromagnetic radiation. The optical black pixels are read during a blanking period of the pixel array when the pixel array is "reset" or calibrated. In an embodiment, light is pulsed during the blanking period of the pixel array when the optical black pixels are being read. After the optical black pixels have been read, the active pixels are read during a readout period of the pixel array. The active pixels may be charged by the electromagnetic radiation that is pulsed during the blanking period such that the active pixels are ready to be read by the image sensor during the readout period of the pixel array.

Figure 2A:
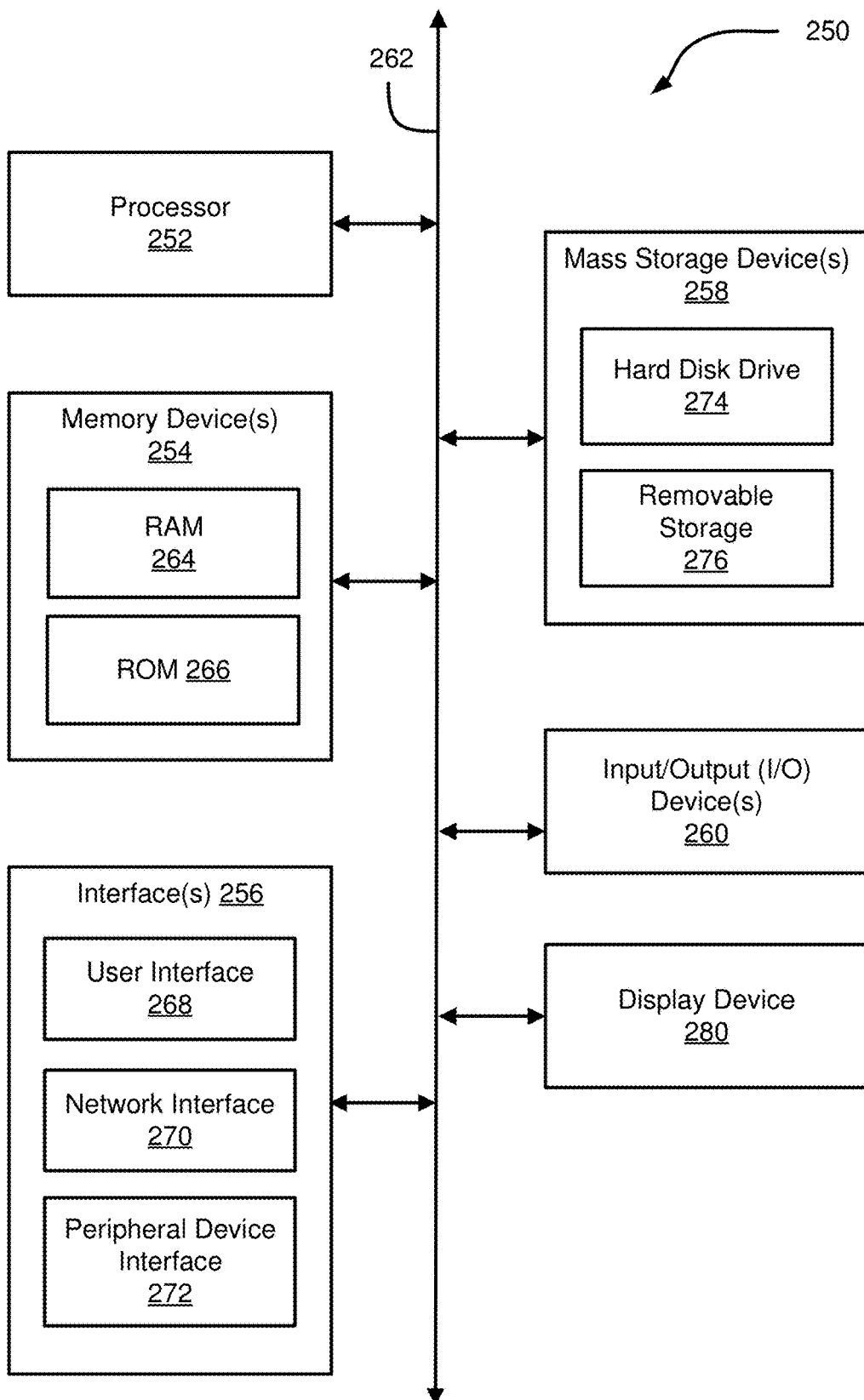
FIG. 2A is a schematic diagram of complementary system hardware.

FIG. 2A is a schematic diagram of complementary system hardware such as a special purpose or general-purpose computer. Implementations within the scope of the present disclosure may also include physical and other non-transitory computer readable media for carrying or storing computer executable instructions and/or data structures. Such computer readable media can be any available media that can be accessed by a general purpose or special purpose computer system. Computer readable media that stores computer executable instructions are computer storage media (devices). Computer readable media that carry computer executable instructions are transmission media. Thus, by way of example, and not limitation, implementations of the disclosure can comprise at least two distinctly different kinds of computer readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer executable instructions or data structures and which can be accessed by a general purpose or special purpose computer. Combinations of the above should also be included within the scope of computer readable media.

Further, upon reaching various computer system components, program code means in the form of computer executable instructions or data structures that can be transferred automatically from transmission media to computer storage media (devices) (or vice versa). For example, computer executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered storage, such as FusionIO). Thus, it should be understood that computer storage media (devices) can be included in computer system components that also (or even primarily) utilize transmission media.

Computer executable instructions comprise, for example, instructions and data which, when executed by one or more processors, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above-mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 2A is a block diagram illustrating an example computing device 250. Computing device 250 may be used to perform various procedures, such as those discussed herein. Computing device 250 can function as a server, a client, or any other computing entity. Computing device 250 can perform various monitoring functions as discussed herein, and can execute one or more application programs, such as the application programs described herein. Computing device 250 can be any of a wide variety of computing devices, such as a desktop computer, a notebook computer, a server computer, a handheld computer, camera control unit, tablet computer and the like.

Computing device 250 includes one or more processor(s) 252, one or more memory device(s) 254, one or more interface(s) 256, one or more mass storage device(s) 258, one or more Input/Output (I/O) device(s) 260, and a display device 280 all of which are coupled to a bus 262. Processor(s) 252 include one or more processors or controllers that execute instructions stored in memory device(s) 254 and/or mass storage device(s) 258. Processor(s) 252 may also include various types of computer readable media, such as cache memory.

Memory device(s) 254 include various computer readable media, such as volatile memory (e.g., random access memory (RAM) 264) and/or nonvolatile memory (e.g., read-only memory (ROM) 266). Memory device(s) 254 may also include rewritable ROM, such as Flash memory.

Mass storage device(s) 258 include various computer readable media, such as magnetic tapes, magnetic disks, optical disks, solid-state memory (e.g., Flash memory), and so forth. As shown in FIG. 2, a particular mass storage device is a hard disk drive 274. Various drives may also be included in mass storage device(s) 258 to enable reading from and/or writing to the various computer readable media. Mass storage device(s) 258 include removable media 276 and/or non-removable media.

I/O device(s) 260 include various devices that allow data and/or other information to be input to or retrieved from computing device 250. Example I/O device(s) 260 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 280 includes any type of device capable of displaying information to one or more users of computing device 250. Examples of display device 280 include a monitor, display terminal, video projection device, and the like.

Interface(s) 256 include various interfaces that allow computing device 250 to interact with other systems, devices, or computing environments. Example interface(s) 256 may include any number of different network interfaces 270, such as interfaces to local area networks (LANs), wide area networks (WANs), wireless networks, and the Internet. Other interface(s) include user interface 268 and peripheral device interface 272. The interface(s) 256 may also include one or more user interface elements 268. The interface(s) 256 may also include one or more peripheral interfaces such as interfaces for printers, pointing devices (mice, track pad, etc.), keyboards, and the like.

Bus 262 allows processor(s) 252, memory device(s) 254, interface(s) 256, mass storage device(s) 258, and I/O device(s) 260 to communicate with one another, as well as other devices or components coupled to bus 262. Bus 262 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 250 and are executed by processor(s) 252. Alternatively, the systems and procedures described herein can be implemented in hardware, or a combination of hardware, software, and/or firmware. For example, one or more application specific integrated circuits (ASICs) or field programmable gate arrays (FPGAs) can be programmed to carry out one or more of the systems and procedures described herein.

Figure 3A:
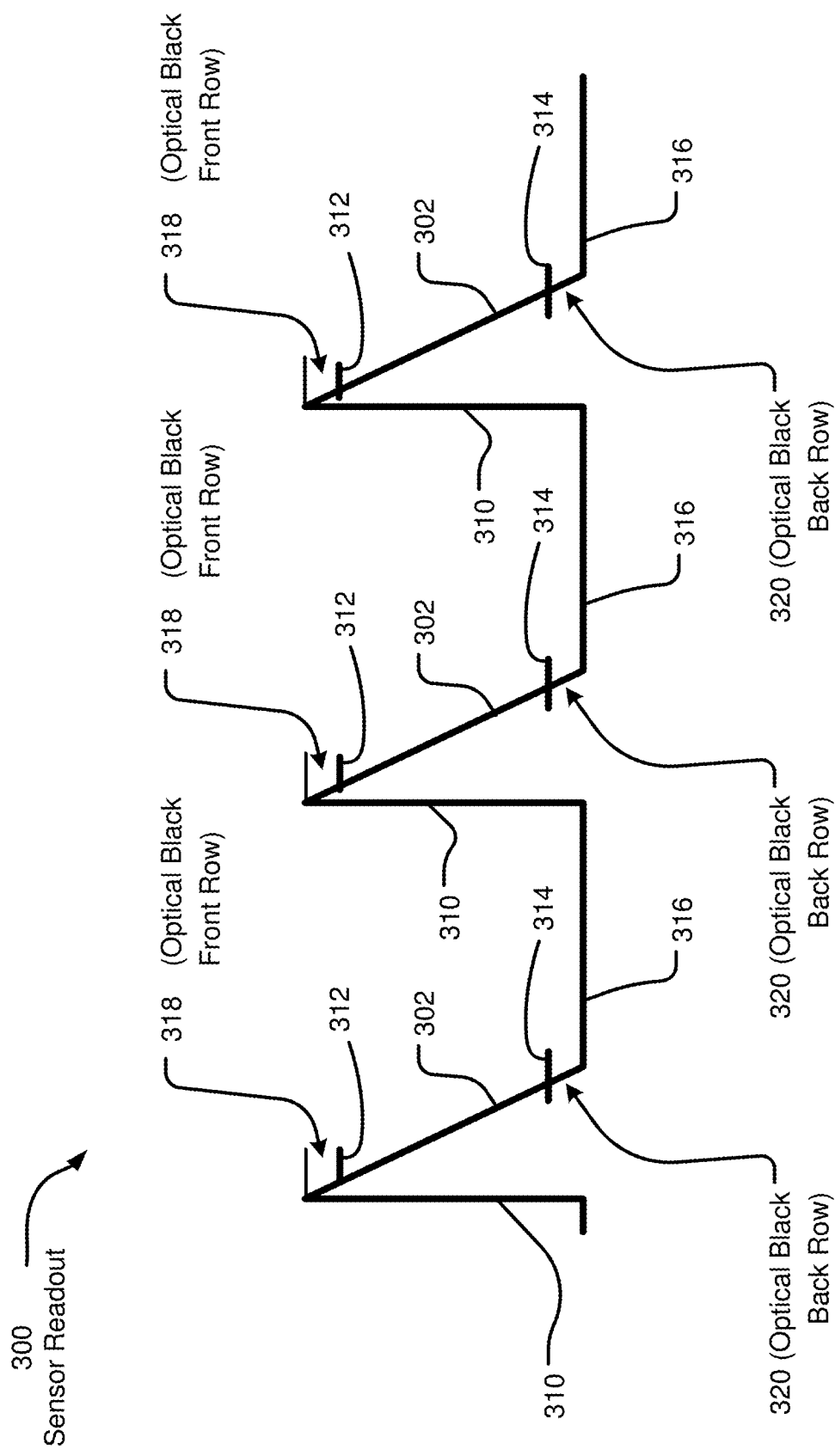

FIG. 3A illustrates the operational cycles of a sensor used in rolling readout mode or during the sensor readout 300. The frame readout period may start at and may be represented by vertical line 310. The readout period 302 is represented by the diagonal or slanted line. The sensor may be read out on a row by row basis, the top of the downwards slanted edge being the sensor top row 312 and the bottom of the downwards slanted edge being the sensor bottom row 314. The time between the last row readout and the next readout period may be called the blanking period 316. It should be noted that some of the sensor pixel rows might be covered with a light shield (e.g., a metal coating or any other substantially black layer of another material type). These covered pixel rows may be referred to as optical black rows 318 and 320. Optical black rows 318 and 320 may be used as input for correction algorithms. As shown in FIG. 3A, these optical black rows 318 and 320 may be located on the top of the pixel array or at the bottom of the pixel array or at the top and the bottom of the pixel array.

FIG. 3B illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 322) may be used to start the integration time by resetting the pixel. The light will then integrate until the next readout period. The position of the electronic shutter 322 can be moved between two readout periods 302 to control the pixel saturation for a given amount of light. It should be noted that this technique allows for a constant integration time between two different lines but introduces a delay when moving from top to bottom rows.

FIG. 3C illustrates the case where the electronic shutter 322 has been removed. In this configuration, the integration of the incoming light may start during the readout period 302 and may end at the next readout period 302, which also defines the start of the next integration.

Figure 3D:
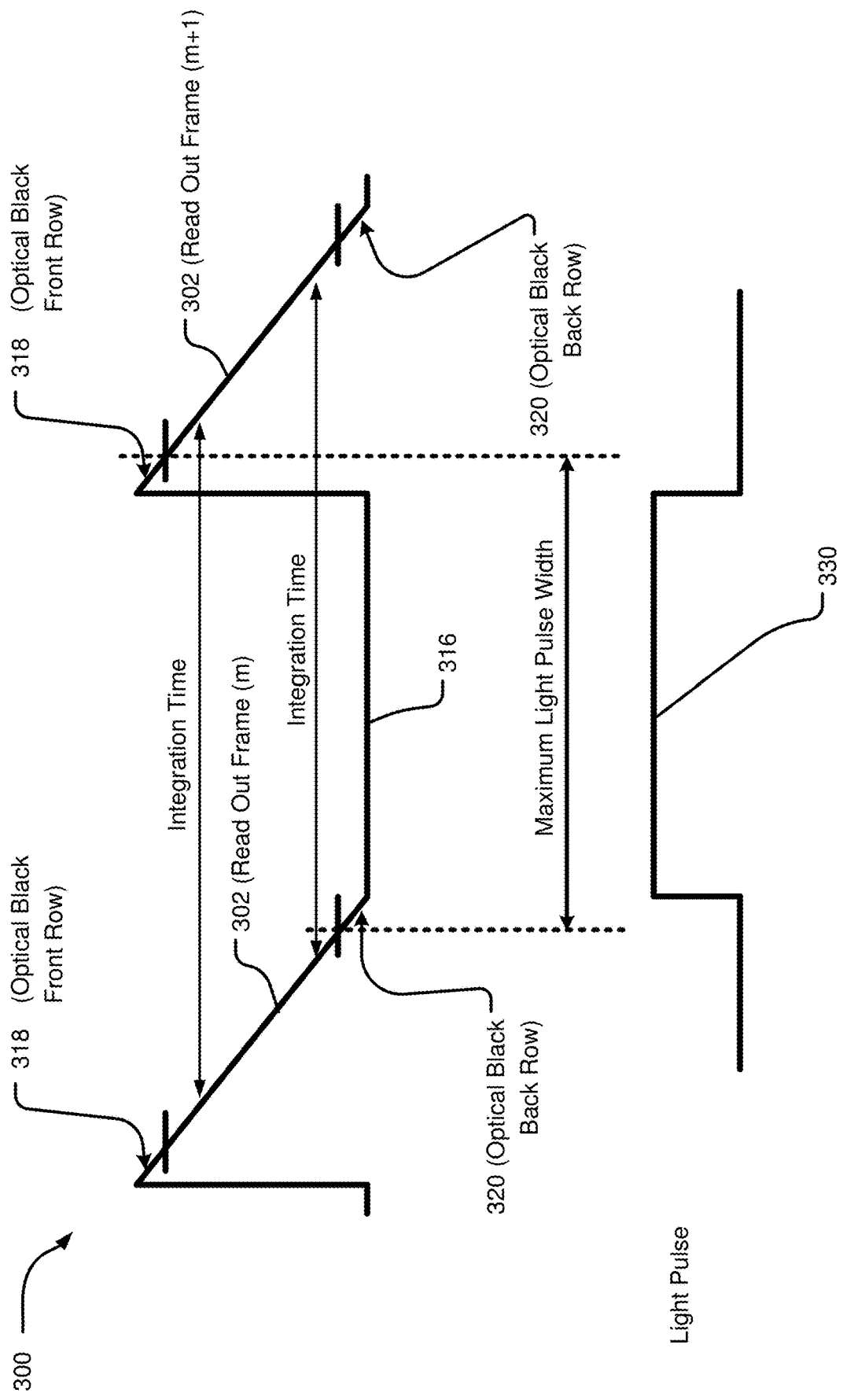

FIG. 3D shows a configuration without an electronic shutter 322, but with a controlled and pulsed light 330 during the blanking period 316. This ensures that all rows see the same light issued from the same light pulse 330. In other words, each row will start its integration in a dark environment, which may be at the optical black back row 320 of read out frame (m) for a maximum light pulse width, and will then receive a light strobe and will end its integration in a dark environment, which may be at the optical black front row 318 of the next succeeding read out frame (m+1) for a maximum light pulse width. In the FIG. 3D example, the image generated from the light pulse will be solely available during frame (m+1) readout without any interference with frames (m) and (m+2). It should be noted that the condition to have a light pulse to be read out only in one frame and not interfere with neighboring frames is to have the given light pulse firing during the blanking period 316. Because the optical black rows 318, 320 are insensitive to light, the optical black back rows 320 time of frame (m) and the optical black front rows 318 time of frame (m+1) can be added to the blanking period 316 to determine the maximum range of the firing time of the light pulse 330.

As illustrated in the FIG. 3A, a sensor may be cycled many times to receive data for each pulsed color or wavelength (e.g., Red, Green, Blue, or other wavelength on the electromagnetic spectrum). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

Figure 4A:
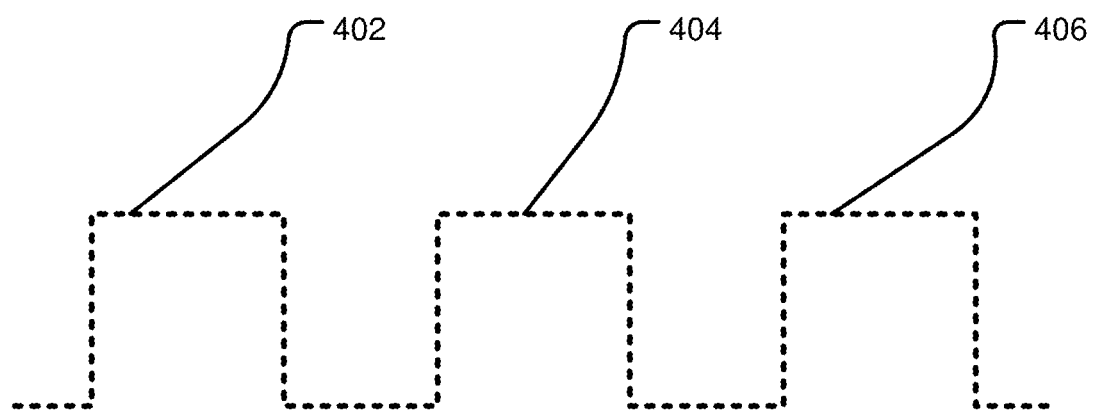
FIG. 4A is a graphical representation of the operation of an embodiment of an electromagnetic emitter.

FIG. 4A graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. FIG. 4A illustrates Pulse 1 at 402, Pulse 2 at 404, and Pulse 3 at 406. In an embodiment, the emitter may pulse during the readout period 302 of the sensor operation cycle. In an embodiment, the emitter may pulse during the blanking period 316 of the sensor operation cycle. In an embodiment, the emitter may pulse for a duration that is during portions of two or more sensor operational cycles. In an embodiment, the emitter may begin a pulse during the blanking period 316, or during the optical black portion 320 of the readout period 302, and end the pulse during the readout period 302, or during the optical black portion 318 of the readout period 302 of the next succeeding cycle. It will be understood that any combination of the above is intended to fall within the scope of this disclosure as long as the pulse of the emitter and the cycle of the sensor correspond.

Figure 4B:
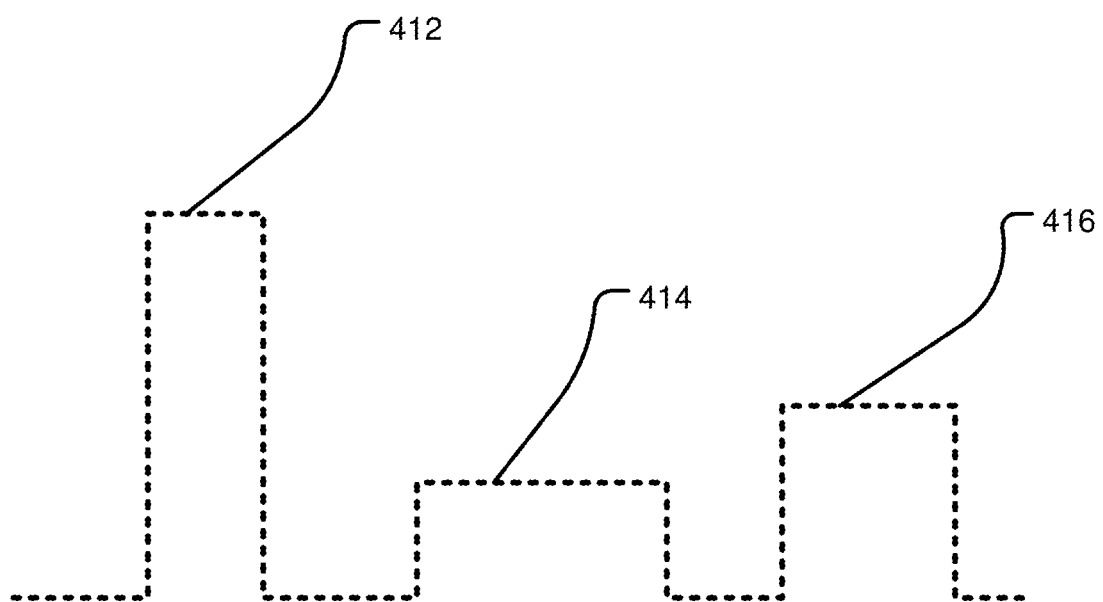
FIG. 4B is a graphical representation of varying the duration and magnitude of the emitted electromagnetic pulse to provide exposure control.

FIG. 4B graphically represents varying the duration and magnitude of the emitted electromagnetic pulse (e.g., Pulse 1 at 412, Pulse 2 at 414, and Pulse 3 at 416) to control exposure. An emitter having a fixed output magnitude may be pulsed during any of the cycles noted above in relation to FIGS. 3D and 4A for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time the emitter pulses a fixed output magnitude, the magnitude of the emission itself may be increased to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality. FIG. 4B illustrates varying the magnitude and duration of the pulses. In the illustration, Pulse 1 at 412 has a higher magnitude or intensity than either Pulse 2 at 414 or Pulse 3 at 416. Additionally, Pulse 1 at 412 has a shorter duration than Pulse 2 at 414 or Pulse 3 at 416, such that the electromagnetic energy provided by the pulse is illustrated by the area under the pulse shown in the illustration. In the illustration, Pulse 2 at 414 has a relatively low magnitude or intensity and a longer duration when compared to either Pulse 1 at 412 or Pulse 3 at 416. Finally, in the illustration, Pulse 3 at 416 has an intermediate magnitude or intensity and duration, when compared to Pulse 1 at 412 and Pulse 2 at 414.

Figure 5:
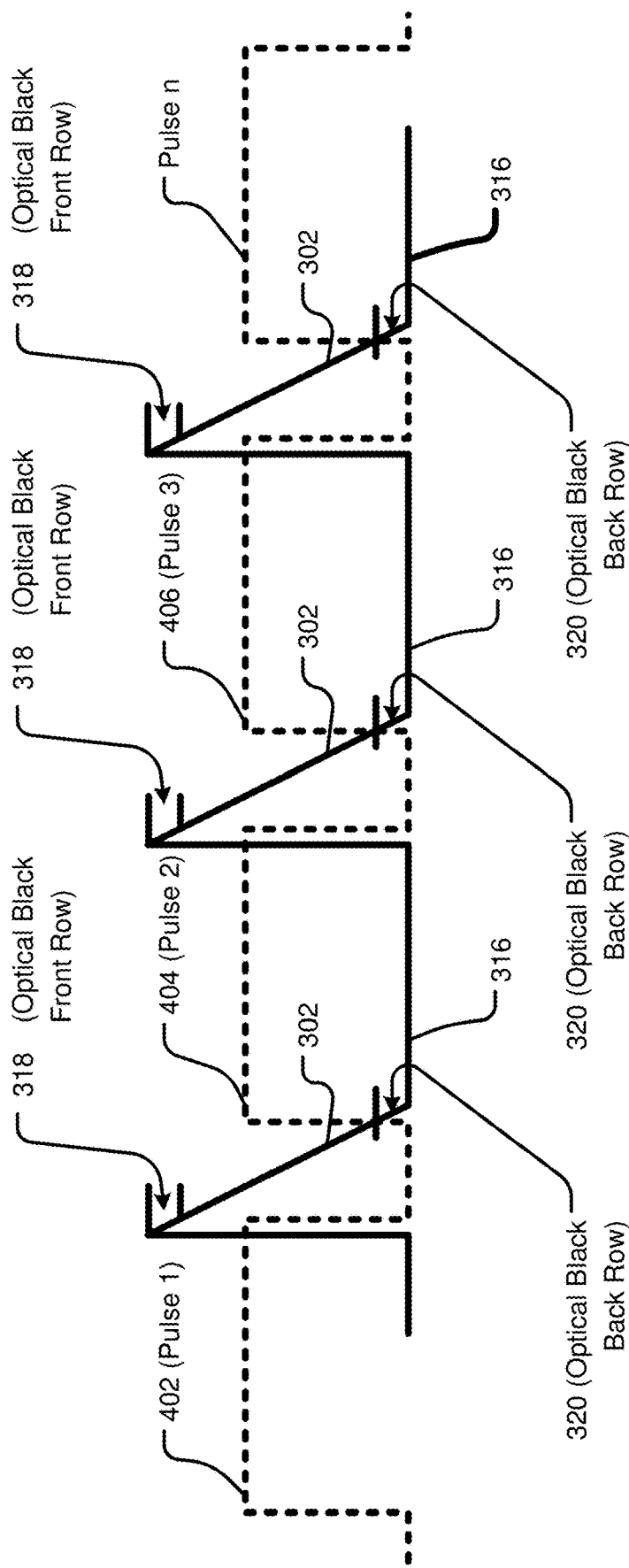
FIG. 5 is a graphical representation of an embodiment of the disclosure combining the operational cycles of a sensor, the electromagnetic emitter, and the emitted electromagnetic pulses of FIGS. 3A-4B, which demonstrate the imaging system during operation.

FIG. 5 is a graphical representation of an embodiment of the disclosure combining the operational cycles, the electromagnetic emitter, and the emitted electromagnetic pulses of FIGS. 3A-3D and 4A to demonstrate the imaging system during operation in accordance with the principles and teachings of the disclosure. As can be seen in the figure, the electromagnetic emitter pulses the emissions primarily during the blanking period 316 of the image sensor such that the pixels will be charged and ready to read during the readout period 302 of the image sensor cycle. The dashed lines in FIG. 5 represent the pulses of electromagnetic radiation (from FIG. 4A). The pulses of electromagnetic radiation are primarily emitted during the blanking period 316 of the image sensor but may overlap with the readout period 302 of the image sensor.

An exposure frame includes the data read by the pixel array of the image sensor during a readout period 302. The exposure frame may be combined with an indication of what type of pulse was emitted by the emitter prior to the readout period 302. The combination of the exposure frame and the indication of the pulse type may be referred to as a dataset. Multiple exposure frames may be combined to generate a black-and-white or RGB color image. Additionally, hyperspectral, fluorescence, and/or laser mapping imaging data may be overlaid on a black-and-white or RGB image.

In an embodiment, an exposure frame is the data sensed by the pixel array during the readout period 302 that occurs subsequent to a blanking period 316. The emission of electromagnetic radiation is emitted during the blanking period 316. In an embodiment, a portion of the emission of electromagnetic radiation overlaps the readout period 302. The blanking period 316 occurs when optical black pixels of the pixel array are being read and the readout period 302 occurs when active pixels of the pixel array are being read. The blanking period 316 may overlap the readout period 302.

FIGS. 6A and 6B illustrate processes for recording an image frame. Multiple image frames may be strung together to generate a video stream. A single image frame may include data from multiple exposure frames, wherein an exposure frame is the data sensed by a pixel array subsequent to an emission of electromagnetic radiation. FIG. 6A illustrates a traditional process that is typically implemented with a color image sensor having a color filter array (CFA) for filtering out certain wavelengths of light per pixel. FIG. 6B is a process that is disclosed herein and can be implemented with a monochromatic "color agnostic" image sensor that is receptive to all wavelengths of electromagnetic radiation.

The process illustrated in FIG. 6A occurs from time t(0) to time t(1). The process begins with a white light emission 602 and sensing white light 604. The image is processed and displayed at 606 based on the sensing at 604.

The process illustrated in FIG. 6B occurs from time t(0) to time t(1). The process begins with an emission of green light 612 and sensing reflected electromagnetic radiation 614 subsequent to the emission of green light 612. The process continues with an emission of red light 616 and sensing reflected electromagnetic radiation 618 subsequent to the emission of red light 616. The process continues with an emission of blue light 620 and sensing reflected electromagnetic radiation 622 subsequent to the emission of blue light 620. The process continues with one or more emissions of a fluorescence excitation wavelengths 624 and sensing reflected electromagnetic energy 626 subsequent to each of the one or more emissions of fluorescence excitation wavelengths of electromagnetic radiation 624. The image is processed and displayed at 628 based on each of the sensed reflected electromagnetic energy instances 614, 618, 622, and 626.

The process illustrated in FIG. 6B provides a higher resolution image and provides a means for generating an RGB image that further includes fluorescence imaging data. When partitioned spectrums of light are used, (as in FIG. 6B) a sensor can be made sensitive to all wavelengths of electromagnetic energy. In the process illustrated in FIG. 6B, the monochromatic pixel array is instructed that it is sensing electromagnetic energy from a predetermined partition of the full spectrum of electromagnetic energy in each cycle. Therefore, to form an image the sensor need only be cycled with a plurality of differing partitions from within the full spectrum of light. The final image is assembled based on the multiple cycles. Because the image from each color partition frame cycle has a higher resolution (compared with a CFA pixel array), the resultant image created when the partitioned light frames are combined also has a higher resolution. In other words, because each and every pixel within the array (instead of, at most, every second pixel in a sensor with a CFA) is sensing the magnitudes of energy for a given pulse and a given scene, just fractions of time apart, a higher resolution image is created for each scene.

As can be seen graphically in the embodiments illustrated in FIGS. 6A and 6B between times t(0) and t(1), the sensor for the partitioned spectrum system in FIG. 6B has cycled at least four times for every one of the full spectrum system in FIG. 6A. In an embodiment, a display device (LCD panel) operates at 50-60 frames per second. In such an embodiment, the partitioned light system in FIG. 6B may operate at 200-240 frames per second to maintain the continuity and smoothness of the displayed video. In other embodiments, there may be different capture and display frame rates. Furthermore, the average capture rate could be any multiple of the display rate.

In an embodiment, it may be desired that not all partitions be represented equally within the system frame rate. In other words, not all light sources have to be pulsed with the same regularity so as to emphasize and de-emphasize aspects of the recorded scene as desired by the users. It should also be understood that non-visible and visible partitions of the electromagnetic spectrum may be pulsed together within a system with their respective data value being stitched into the video output as desired for display to a user.

An embodiment may comprise a pulse cycle pattern as follows:
  i. Green pulse;
  ii. Red pulse;
  iii. Blue pulse;
  iv. Green pulse;
  v. Red pulse;
  vi. Blue pulse;
  vii. Fluorescence excitation pulse;
  viii. (Repeat)

As can be seen in the example, a fluorescence excitation partition may be pulsed at a rate differing from the rates of the other partition pulses. This may be done to emphasize a certain aspect of the scene, with the fluorescence imaging data simply being overlaid with the other data in the video output to make the desired emphasis. It should be noted that the addition of a fluorescence partition on top of the RED, GREEN, and BLUE partitions does not necessarily require the serialized system to operate at four times the rate of a full spectrum non-serial system because every partition does not have to be represented equally in the pulse pattern. As seen in the embodiment, the addition of a partition pulse that is represented less in a pulse pattern (fluorescence excitation in the above example), would result in an increase of less than 20% of the cycling speed of the sensor to accommodate the irregular partition sampling.

In various embodiments, the pulse cycle pattern may further include any of the following wavelengths in any suitable order. Such wavelengths may be particularly suited for exciting a fluorescent reagent to generate fluorescence imaging data by sensing the relaxation emission of the fluorescent reagent based on a fluorescent reagent relaxation emission:
  i. 770±20 nm;
  ii. 770±10 nm;
  iii. 770±5 nm;
  iv. 790±20 nm;
  v. 790±10 nm;
  vi. 790±5 nm;

vii. 795±20 nm;
viii. 795±10 nm;
ix. 795±5 nm;
x. 815±20 nm;
xi. 815±10 nm;
xii. 815±5 nm;
xiii. 770 nm to 790 nm; and/or
xiv. 795 nm to 815 nm.

Figure 7A:
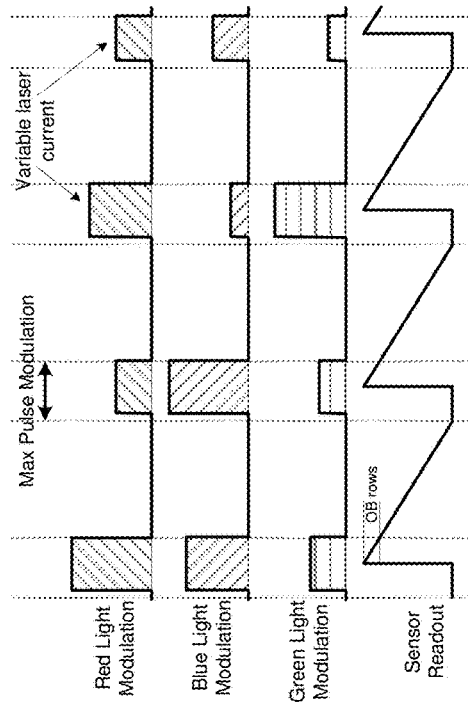
FIGS. 7A-7E illustrate schematic views of the processes over an interval of time for recording a frame of video for both full spectrum light and partitioned spectrum light.
Figure 7C:
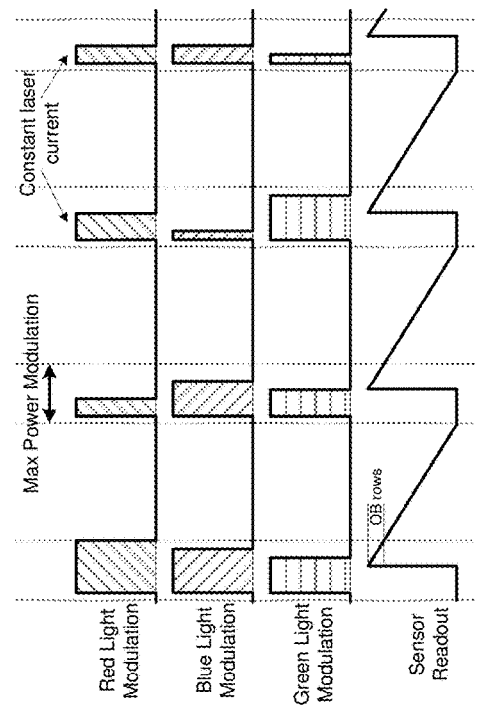
Figure 7B:
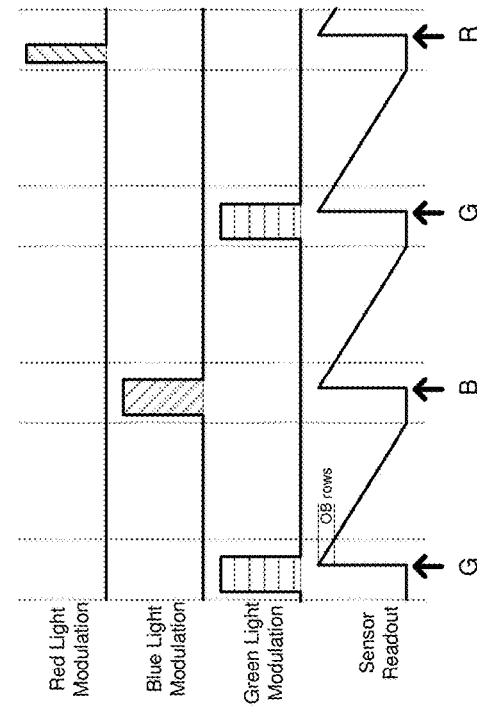

The partition cycles may be divided so as to accommodate or approximate various imaging and video standards. In an embodiment, the partition cycles may comprise pulses of electromagnetic energy in the Red, Green, and Blue spectrum as follows as illustrated best in FIGS. 7A-7D. In FIG. 7A, the different light intensities have been achieved by modulating the light pulse width or duration within the working range shown by the vertical grey dashed lines. In FIG. 7B, the different light intensities have been achieved by modulating the light power or the power of the electromagnetic emitter, which may be a laser or LED emitter, but keeping the pulse width or duration constant. FIG. 7C shows the case where both the light power and the light pulse width are being modulated, leading to greater flexibility. The partition cycles may use Cyan Magenta Yellow (CMY), infrared, ultraviolet, hyperspectral, and fluorescence using a non-visible pulse source mixed with visible pulse sources and any other color space required to produce an image or approximate a desired video standard that is currently known or yet to be developed. It should also be understood that a system may be able to switch between the color spaces on the fly to provide the desired image output quality.

Figure 7D:
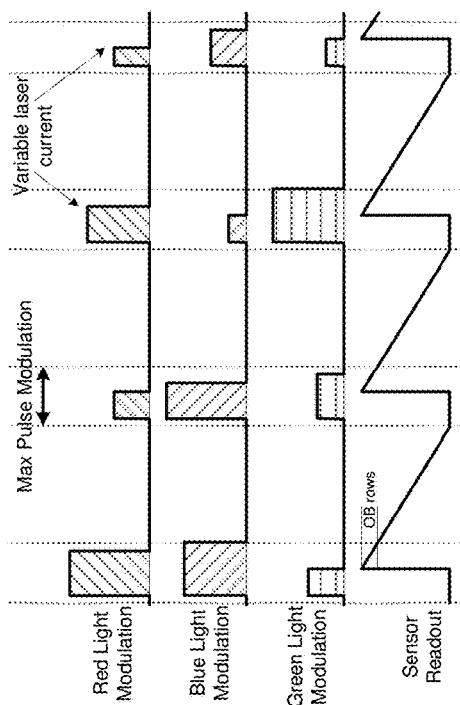

In an embodiment using color spaces Green-Blue-Green-Red (as seen in FIG. 7D) it may be desirous to pulse the luminance components more often than the chrominance components because users are generally more sensitive to light magnitude differences than to light color differences. This principle can be exploited using a mono-chromatic sensor as illustrated in FIG. 7D. In FIG. 7D, green, which contains the most luminance information, may be pulsed more often or with more intensity in a (G-B-G-R-G-B-G-R . . . ) scheme to obtain the luminance data. Such a configuration would create a video stream that has perceptively more detail, without creating and transmitting unperceivable data.

Figure 7E:
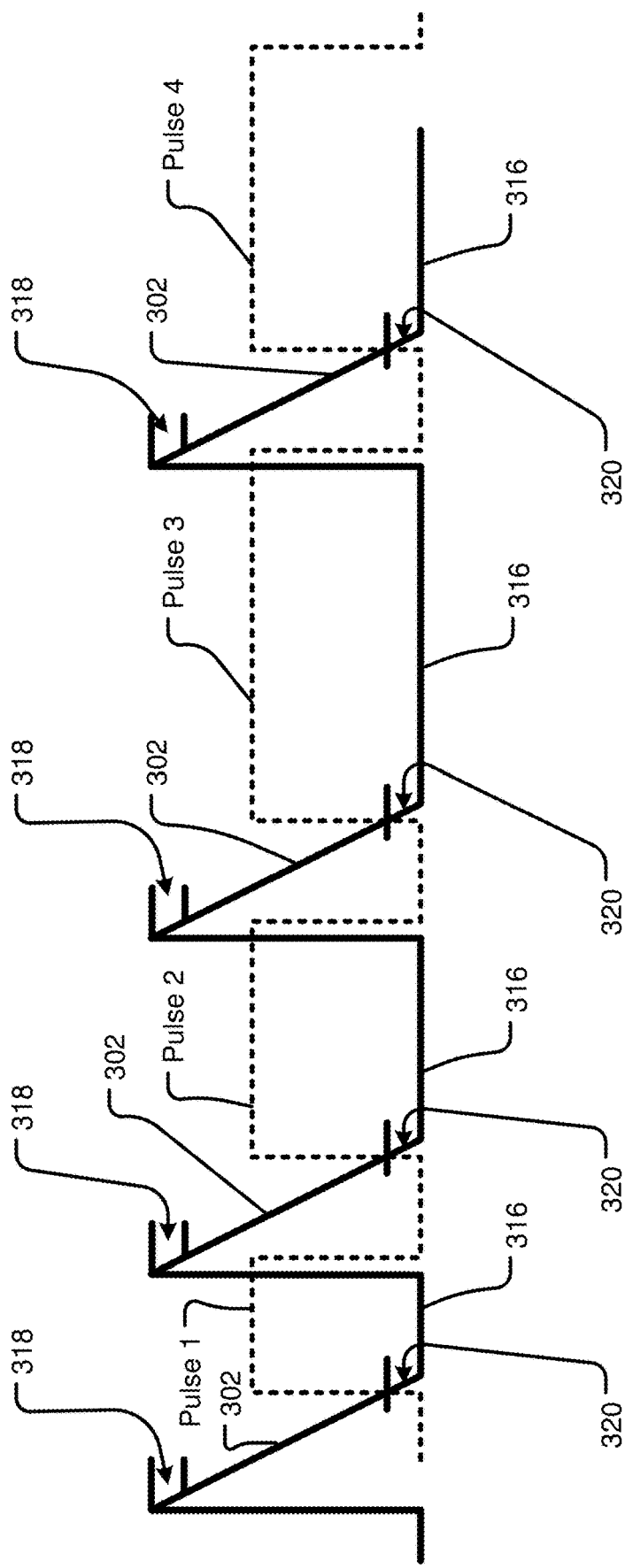

In an embodiment, duplicating the pulse of a weaker partition may be used to produce an output that has been adjusted for the weaker pulse. For example, blue laser light is considered weak relative to the sensitivity of silicon-based pixels and is difficult to produce in comparison to the red or green light, and therefore may be pulsed more often during a frame cycle to compensate for the weakness of the light. These additional pulses may be done serially over time or by using multiple lasers that simultaneously pulse to produce the desired compensation effect. It should be noted that by pulsing during a blanking period (time during which the sensor is not reading out the pixel array), the sensor is insensitive to differences/mismatches between lasers of the same kind and simply accumulates the light for the desired output. In another embodiment, the maximum light pulse range may be different from frame to frame. This is shown in FIG. 7E, where the light pulses are different from frame to frame. The sensor may be built to be able to program different blanking times with a repeating pattern of two or three or four or n frames. In FIG. 7E, four different light pulses are illustrated, and Pulse 1 may repeat for example after Pulse 4 and may have a pattern of four frames with different blanking times. This technique can be used to place the most powerful partition on the smallest blanking time and therefore allow the weakest partition to have wider pulse on one of the next frames without the need of increasing the readout speed. The reconstructed frame can still have a regular pattern from frame to frame as it is constituted of many pulsed frames.

Figures 8A, 8B:
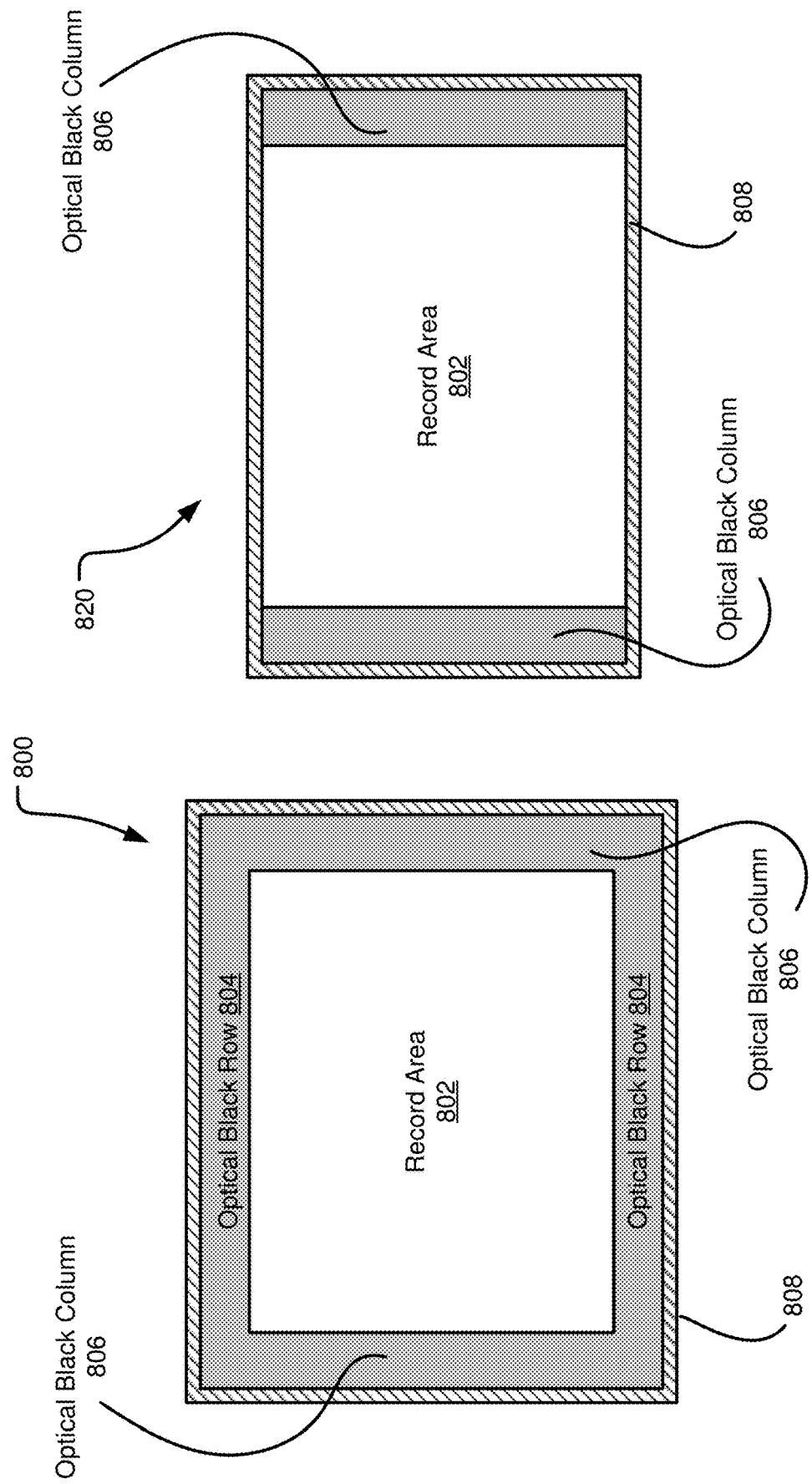
FIG. 8A illustrates a traditional image sensor with optical black pixels disposed around a recording area of active pixels.
FIG. 8B illustrates an embodiment of a minimal area image sensor.

Referring now to FIGS. 8A and 8B, implementations of image sensors are illustrated. The image sensor illustrated in FIG. 8A is a traditional image sensor 800 including a pixel array common in the prior art. The minimal area image sensor 820 illustrated in FIG. 8B is a pixel array in accordance with the teachings and principles of the disclosure. The minimal area image sensor 820 may be used in a distal tip of an endoscope. The distal tip of an endoscope is necessarily small because the distal tip is usually inserted in small areas such as body cavities. The distal tip of an endoscope is often too small to accommodate a traditional image sensor 800.

In a space-constrained environment such as the distal tip of an endoscope, it may be desirable to reduce non-sensitive portions of an image sensor to maximize the area of the image sensor that is devoted to light sensing elements. This can reduce the total area of the image sensor while preserving image quality. One implementation for reducing the non-light sensing elements in the image sensor is to eliminate or reduce the number of optical black ("OB") rows in the image sensor. However, eliminating the optical black rows can also eliminate the possibility of implementing an OB-based column fixed pattern noise cancellation method that is commonly used in conventional imaging systems. Column fixed pattern noise cancellation requires black pixel data with typically 10 to 100 black pixels per column. The black pixels correct for a column-wise random offset prior to reading out light sensing pixels. Disclosed herein are alternative methods, systems, and devices for correcting for fixed pattern noise when using a minimal area image sensor 820.

Image sensors can incorporate special purpose, optically blind or optical black ("OB") rows and/or columns. Optical black pixels may alternatively be referred to as manufacturing buffer pixels or dummy pixels. An optical black row 804 is located at the top and/or bottom of a record area 802. The record area 802 includes the imaging pixel array. An optical black column 806 is located to the right and/or left of the pixel array. The optical black rows and columns are used to offset calibration of the record area 802.

The example layout of the traditional image sensor 800 includes an optical black row 804 on the top and bottom of the traditional record area 802. The traditional image sensor 800 further includes an optical black column 806 on the left and right sides of the record area 802. The example layout of the minimal area image sensor 820 includes optical black columns 806 on the left and right sides of the record area 802. The minimal area image sensor 820 does not include any optical black rows 804. Each of the example embodiments may include a guard ring 808 surrounding the circumference of the image sensor 800, 820.

The optical black rows 804 may be used to monitor the analog pixel black level for purposes of an optical black clamp algorithm. The optical black rows 804 may also be used by a digital algorithm for the purpose of cancelling column fixed pattern noise (CFPN). The optical black columns 806 may be used to assess the line offset as a means to cancel out line noise in the record area 802. Because line noise can be temporal, the line offset may be computed anew for each line of the record area 802 in every frame.

The minimal area image sensor 820 provides an overall reduction in the size of the image sensor by removing the optical black rows 804 from the top and bottom sides of the record area 802. When deploying the minimal area image sensor 820, the optical black columns 806 are used for the optical black clamp algorithm rather than any optical black rows 804. In an embodiment, all fixed pattern noise, including column fixed pattern noise, can be cancelled by acquiring frames of dark data. This negates the need for a dedicated CFPN correction and its associated optical black rows 804.

Figure 9:
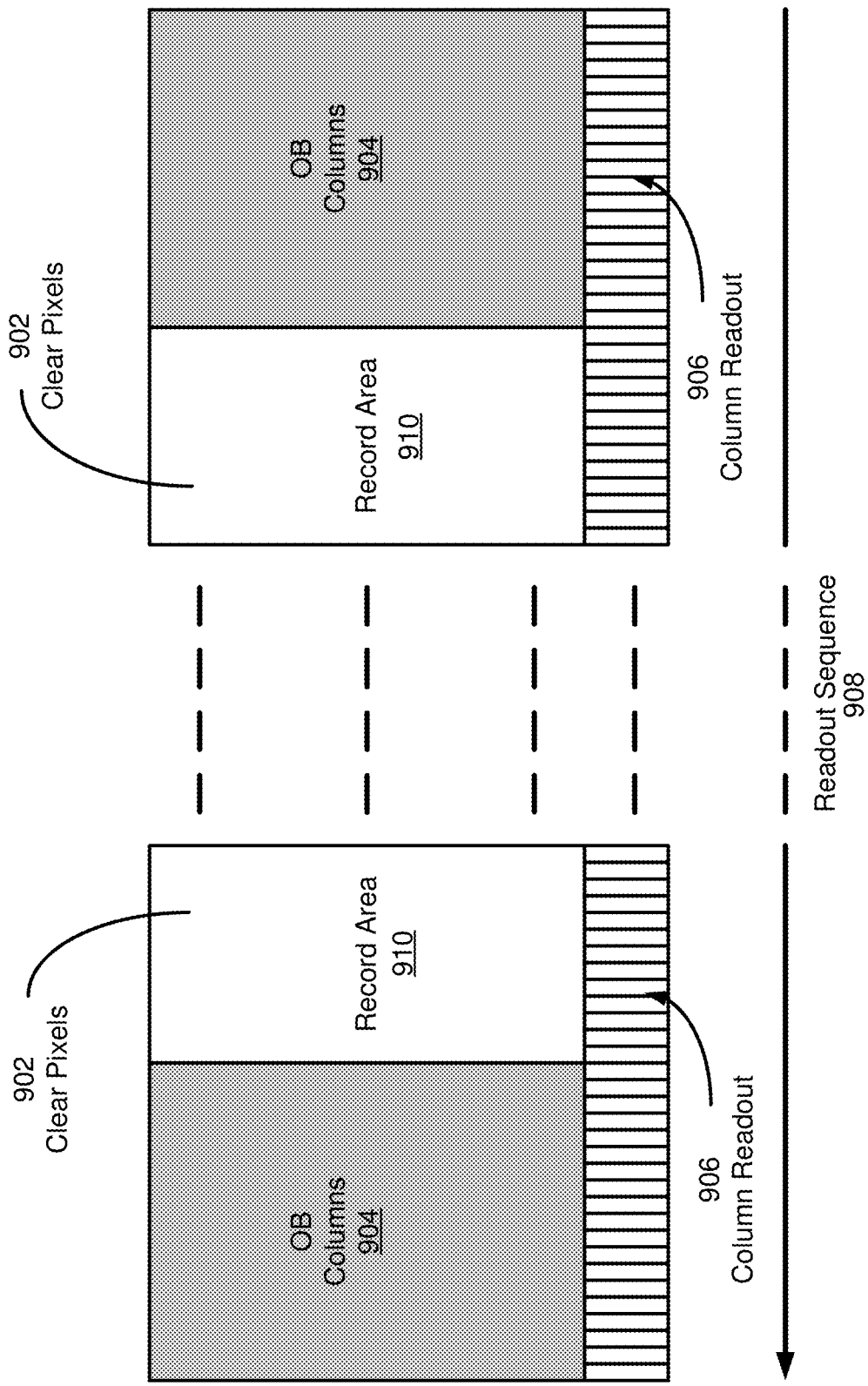
FIG. 9 is a readout sequence of an embodiment of an image sensor.
Figure 10:
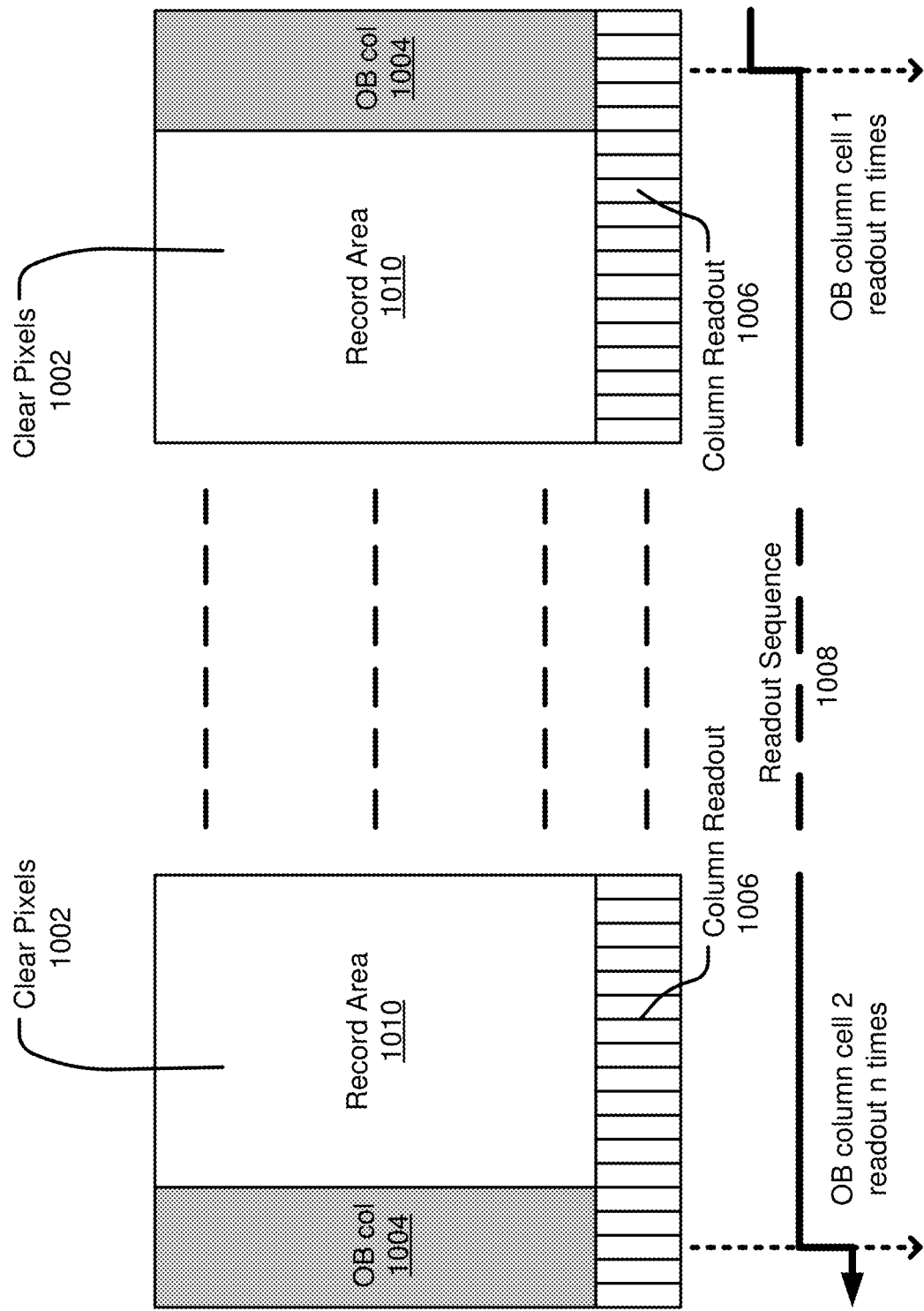
FIG. 10 is a readout sequence of an embodiment of a minimal area image sensor.

The number of optical black columns 806 might typically be 100 or more depending on space constraints. The more optical black columns 806 that are available, the greater the line-offset precision may be. Greater precision means lower line noise post-correction. Normally, all available physical optical black pixels are read for each line as shown in FIG. 9. A further degree of pixel array size reduction can be achieved if, instead of having the requisite number of physical optical black pixels, (given a certain precision target), a smaller number of physical optical black pixels are implemented and the physical optical black pixels are resampled multiple times during the horizontal readout process of the record area 802 and the optical black columns 806. This approach is illustrated in FIG. 10.

In an alternative embodiment, a minimal area image sensor includes optical black rows 804 but does not include optical black columns 806. In such an embodiment, the optical black rows 804 may be read before and after reading the active pixels in the record area 802 of the pixel array.

The disclosures provided herein may be applied to all forms of fixed pattern noise and are not necessarily restricted to cancelling column fixed pattern noise. Other types of fixed pattern noise may be cancelled by acquiring frames of dark data to negate the need for a dedicated column fixed pattern noise correction with its associated optical black rows. In an embodiment, an off-sensor frame of memory is used for storing each pixel's calibration data and subsequently cancelling all sources of fixed pattern noise at the pixel level. Although more memory may be needed for a black frame calibration than for a column fixed pattern noise algorithm, there may be an advantage in that all sources of fixed pattern noise can be eliminated or significantly mitigated by way of the methods, systems, and devices disclosed herein. Example sources of fixed pattern noise that can be eliminated or mitigated by way of the disclosures herein include column fixed pattern noise, pixel fixed pattern noise, and row fixed pattern noise.

FIG. 9 illustrates a readout sequence 908 for a pixel array common in the prior art. As shown in FIG. 9, the readout sequence 908 begins with column readout 906 for each of the optical black columns 904. The optical black columns 904 may be similar to those optical black columns 806 illustrated in FIGS. 8A and 8B. Upon completion of the column readout 906 for the optical black columns 904, the readout sequence 908 begins the column readout 906 for the record area 910. The record area 910 may be similar to the record area 802 illustrated in FIGS. 8A and 8B. The record area 910 may include clear pixels 902 or color agnostic pixels. The readout sequence 908 continues until the entire record area 910 has been read. After the record area 910 has been read, the optical black columns 904 on the opposite side are read. The readout sequence 908 continues line-by-line until every row of the pixel array has been read.

FIG. 10 illustrates a readout sequence 1008 for a pixel array having an area size reduction that reduces the number of optical black pixels. In the readout sequence 1008 illustrated in FIG. 10, the optical black columns 1004 undergo column readout 1006 multiple times. As shown in FIG. 10, the optical black column 1004 readout can be resampled m time or n times. The record area may include clear pixels 1002.

Raw CMOS image sensor data present at the output of the digitizer may be far from ideal. It may often be the case that the optimal order with which to read out a horizontal row of pixels does not equate to the actual physical order within the array. Also, raw data often reveals undesirable artifacts that reflect the nature of the readout architecture. These readout artifacts may include column fixed pattern noise arising from the variation in offset from column to column and may further include temporal line noise resulting from circuit resets associated with the horizontal readout process.

Another property of CMOS (Complementary Metal Oxide Semiconductor) sensors is that a degree of dark signal may be generated by the photodiode within the pixel. The amount of integrated signal arising from dark signal depends on exposure time and temperature. Because the dark signal may be indistinguishable from photo-signal, changes in the dark signal translate to changes in signal pedestal in the analog domain. Therefore, it may be important to sample and adjust for the dark signal so the available dynamic range of the analog to digital converter can be fully exploited.

Figure 11:
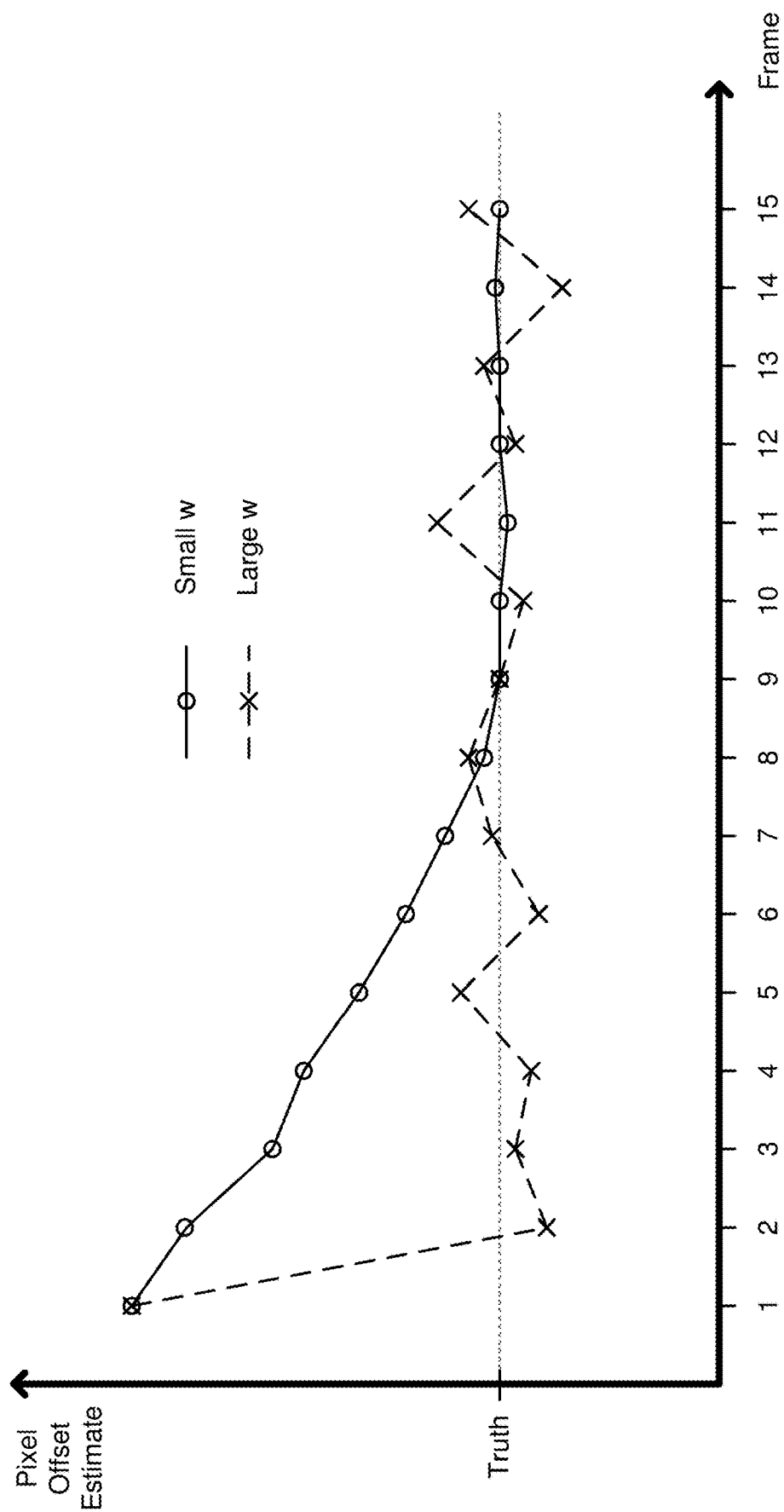
FIG. 11 is a graphical representation of a simple exponential smoothing pixel offset estimation with small and large values for w.

FIG. 11 is a graphical representation of a simple exponential smoothing (SES) pixel offset estimation with small and large values for w. SES pixel offset estimation can be implemented to reduce or eliminate fixed pattern noise in exposure frames.

Exponential smoothing is a timeseries forecasting method. Exponential smoothing results in a prediction that is a weighted sum of past observations, wherein the weights decay exponentially as past observations get older. In an embodiment, SES is used to generate a reference frame based on a plurality of dark exposure frames. Each of the plurality of dark exposure frames is generated by the pixel array and includes dark frame data that is sensed when the emitter is not emitting electromagnetic radiation. The reference frame may be applied to reduce fixed pattern noise in exposure frames and/or image frames generated by the image sensor. SES is used to increase the precision of the reference frame. In an embodiment, the SES algorithm explicitly uses an exponentially decreasing weight for factoring in previously captured dark exposure frames.

In an embodiment, SES is applied to dark frame data from a plurality of dark exposure frames. SES is used to generate a reference frame based on the dark frame data captured in the plurality of dark exposure frames. The reference frame does not include imaging data that is displayed on a screen or otherwise provided to a user, and instead includes data that is used to remove fixed pattern noise from exposure frames and/or image frames. The reference frame is calculated by applying SES to the plurality of dark exposure frames. The plurality of dark exposure frames are captured over time and older dark exposure frames are given less weight when calculating the reference frame. The reference frame includes reference data that is subtracted from exposure frames and/or image frames in furtherance of reducing fixed pattern noise. Each of the plurality of dark exposure frames is sensed by the pixel array when a light deficient environment is dark, and an emitter is not pulsing electromagnetic radiation.

In an embodiment, an emitter emits pulses of electromagnetic radiation in a pattern that includes varying wavelengths of electromagnetic radiation. In an embodiment, the pattern includes red, green, blue, and fluorescence wavelengths of electromagnetic radiation. The pattern may further include instances wherein the emitter is not emitting electromagnetic radiation. The pixel array can be configured to sense dark frame data when the emitter is not emitting electromagnetic radiation. When the pixel array senses dark frame data, this results in a dark exposure frame. In an embodiment, the pattern of varying wavelengths of electromagnetic radiation further includes instances wherein the emitter is not emitting electromagnetic radiation. The pixel array generates an exposure frame in response to each emission of electromagnetic radiation, and additionally generates a dark exposure frame in response to an instance wherein the emitter is not emitting electromagnetic radiation. The exposure frames and dark exposure frames may be captured in a repeating pattern over time such that the dark exposure frames are interspersed between (non-dark) exposure frames. A series of exposure frames may be combined to generate an image frame, and in an embodiment, there is a dark exposure frame corresponding with each image frame or grouping of image frames. The series of dark exposure frames are used to generate a reference frame, and the reference frame is used to reduce the fixed pattern noise present in the exposure frames (and image frames). SES is applied to the series of dark exposure frames such that older dark exposure frames have lesser weight than newer dark exposure frames.

In an embodiment, a single reference frame is incrementally adjusted each time a dark exposure frame is sensed by the pixel array. Each pixel sample taken in the dark exposure frame is divided by an appropriate binary number ($2^w$) before being added to the buffer content and multiplied by $(2^w-1)/2^w$. FIG. 11 graphically illustrates the impact on the pixel offset estimate for small values of w and large values of w. As shown in FIG. 11, high values of w result in greater statistical precision over time in a stable scenario. Lower values of w cause the SES correction to be more reactive to rapid changes at the expense of precision and stability. In an embodiment, the value of w is tunable via control registers in communication with the endoscopic system.

In an embodiment, dark current temperature dependence can be overcome by using a running average calibration as described herein. In a rolling shutter operation, pixel integration time may be changed on a frame-to-frame basis to accommodate light environment changes controlled by an auto exposure algorithm. For example, the frame readout sequence illustrated in FIGS. 3A-3D illustrate an electronic shutter being adjusted within the frame to control integration time. Because the calibration may be performed at a given integration time, the dark frame correction algorithm may lose efficacy and become inaccurate when trying to correct frames with different integration time. One implementation of the disclosure to overcome this issue is to introduce a second calibration point per pixel. This may require a second frame of memory. The second calibration point for each pixel may be collected at a different integration time. Pixel calibration data at a given integration time may be computed using linear interpolation. However, the use of linear interpolation can introduce interpolation error and complicate backend processing of the image data.

When pulsing light in a light deficient environment, the pixel integration time may be substantially constant from frame to frame. This is illustrated especially in FIG. 3D, where light intensity is adjusted by changing the light pulse width or level. In this implementation, only one integration time calibration may be required, and interpolation may not be needed. In an embodiment, dark frame subtraction can be used to adjust for the average offset of each pixel. This can suppress all forms of fixed pattern noise. Because the pixel offsets have temperature dependence, the correction can be a running average process by taking sample dark frames at regular intervals and updating stored correction data based on the samples. The resultant quality of this correction may depend on the sampling statistics.

In an embodiment, the uncertainty of a pixel offset estimate is equal to the temporal noise of that pixel divided by the square root of the number of samples. This uncertainty may directly translate to post-correction pixel fixed pattern noise and is independent of the original fixed pattern noise. In an embodiment where a video stream is captured at the rate of 60 image frames per second, the pixel fixed pattern noise may be less than one-fourth of the pixel temporal noise to be imperceptible to a human viewer. The statistics for the perception criterion depend only on pixel temporal noise as follows:

$$PFPN_{required} \leq \frac{\sigma_T}{4}$$

$$PFPN_{realized} = \frac{\sigma_T}{\sqrt{N_f}}$$

$$\therefore N_f \geq 16$$

where $\sigma_T$ is the pixel temporal noise. Therefore, the frame correction process should be effective so long as there are at least 16 dark frames used to compute the average.

In an embodiment, SES capture on dark frames only is calculated according to:

$$b_{i,j} = d_{i,j} \quad (j = 0)$$
$$b_{i,j} = \frac{1}{2^w} d_{i,j} + \frac{(2^w-1)}{2^w} b_{i,(j-1)} \quad (j > 0)$$

where $b_{i,j}$ is the dark frame correction buffer content for pixel i, following dark frame number j and $d_{i,j}$ is the raw dark data for pixel i, taken from dark frame j. w is a tunable integer.

In an embodiment, SES is applied non-dark exposure frames according to:

$$x'_i = x_i - b_i + B$$

where $x_i$ is the raw data input for pixel i in any non-dark frame and $b_i$ is the current dark frame buffer content. $x'_i$ is the output and B is the black clamp target level.

Figure 12:
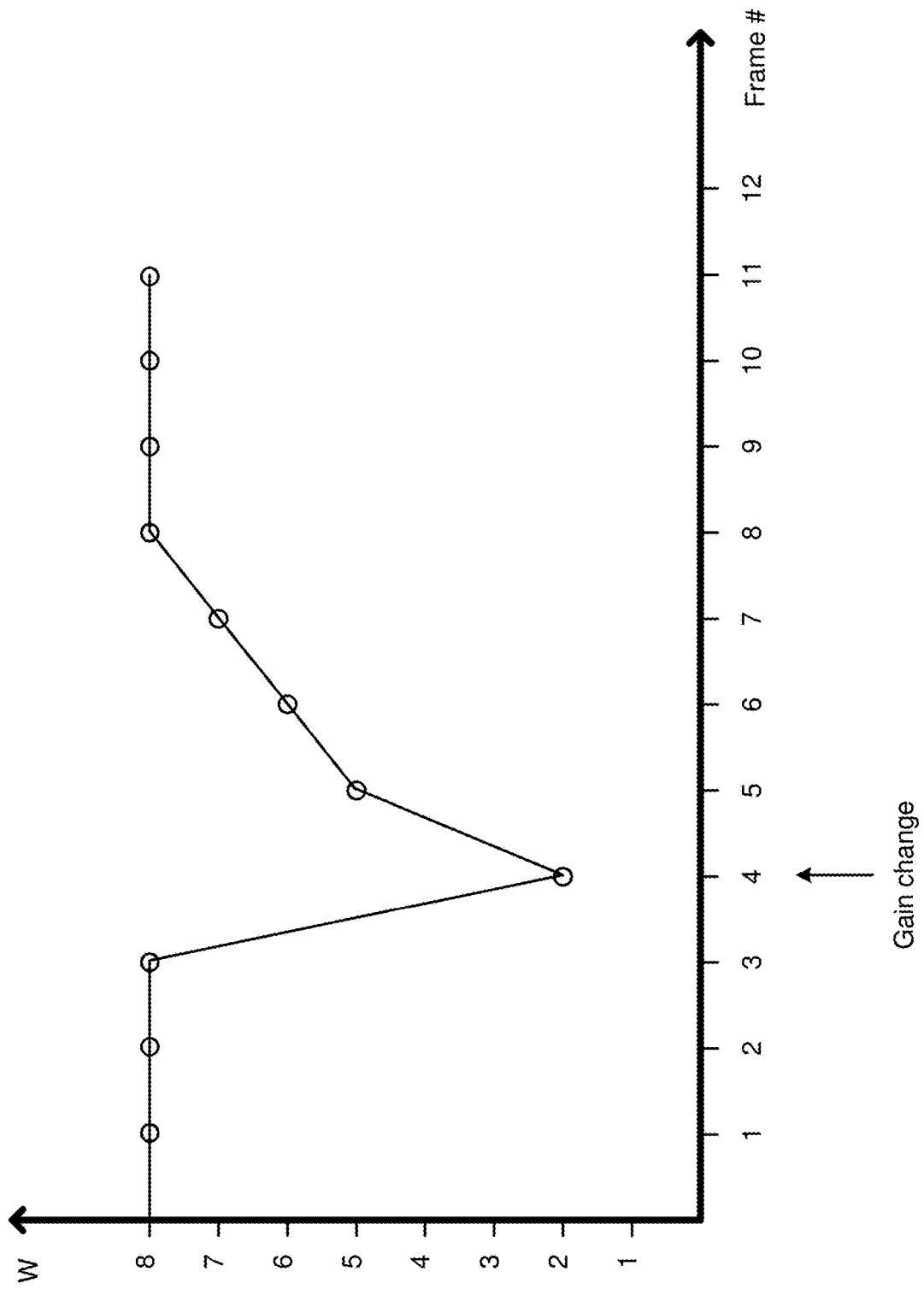
FIG. 12 is a graphical representation of a modulation of the simple exponential smoothing index after a gain change.

FIG. 12 is a graphical representation of a modulation of the simple exponential smoothing (SES) index after a gain change. In an embodiment, the values of w are tunable via control registers in communication with the endoscopic system. The value of w may be automatically adjusted to ensure corrections are reactive at startup, when $T_J$ is changing most dramatically, or in certain embodiments following changes in exposure time. For example, if a large change in gain or exposure time occurs, the value of w can be lowered and then restored to a baseline incrementally from frame to frame. The incremental adjustments can vary linearly or in a roughly exponential manner as shown in FIG. 12.

Figure 13:
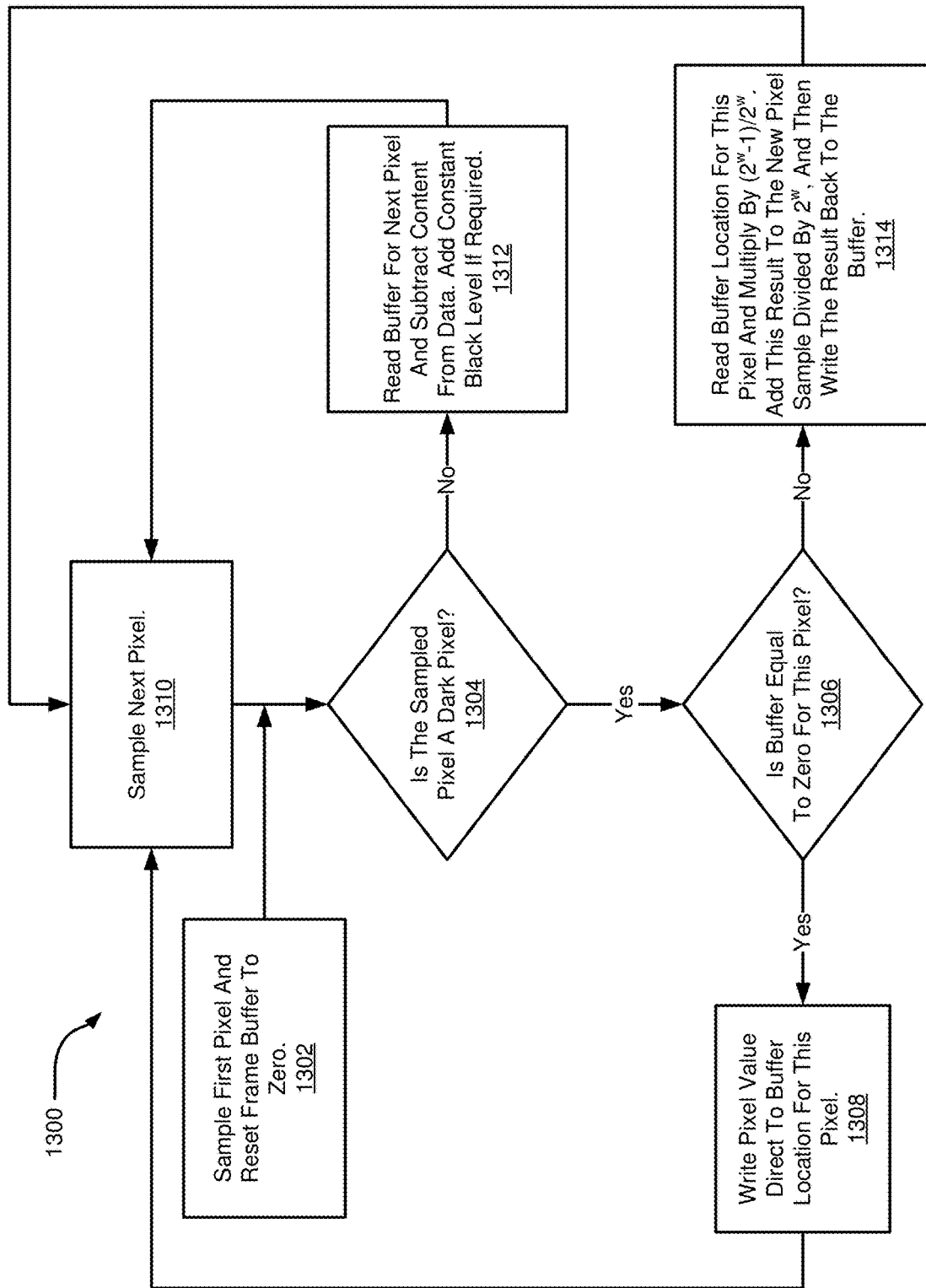
FIG. 13 is a schematic diagram of a process flow for cancellation of fixed pattern noise.

FIG. 13 is a schematic diagram of a process flow 1300 for cancellation of fixed pattern noise. The process flow 1300 includes sampling at 1302 the first pixel and resetting the frame buffer to zero. The process flow 1300 includes determining at 1304 whether the sampled pixel is a dark pixel (may be referred to as an optical black pixel). If it is determined at 1304 that the sampled pixel is a dark pixel, then the process flow 1300 includes determining at 1306 whether the buffer for the pixel is zero. If it is determined at 1306 that the buffer for the pixel dark pixel is zero, then the pixel value is written at 1308 directly to the buffer location for the dark pixel. The next pixel is sampled at 1310. If it is determined at 1306 that the buffer for the dark pixel is not equal to zero, then the buffer location for the dark pixel is read at 1314 and multiplied by $$\frac{(2^w - 1)}{2^w}.$$

The result is added to the new pixel sample and divided by $2^w$ and then written back to the buffer. The next pixel is sampled at 1310.

If it is determined at 1304 that the sampled pixel is not a dark pixel, then the process flow 1300 includes reading the buffer for the active (non-dark) pixel at 1312 and subtracting content from the data. The process flow 1300 may further including adding constant black level if required. The next pixel is sampled at 1310.

Figure 14:
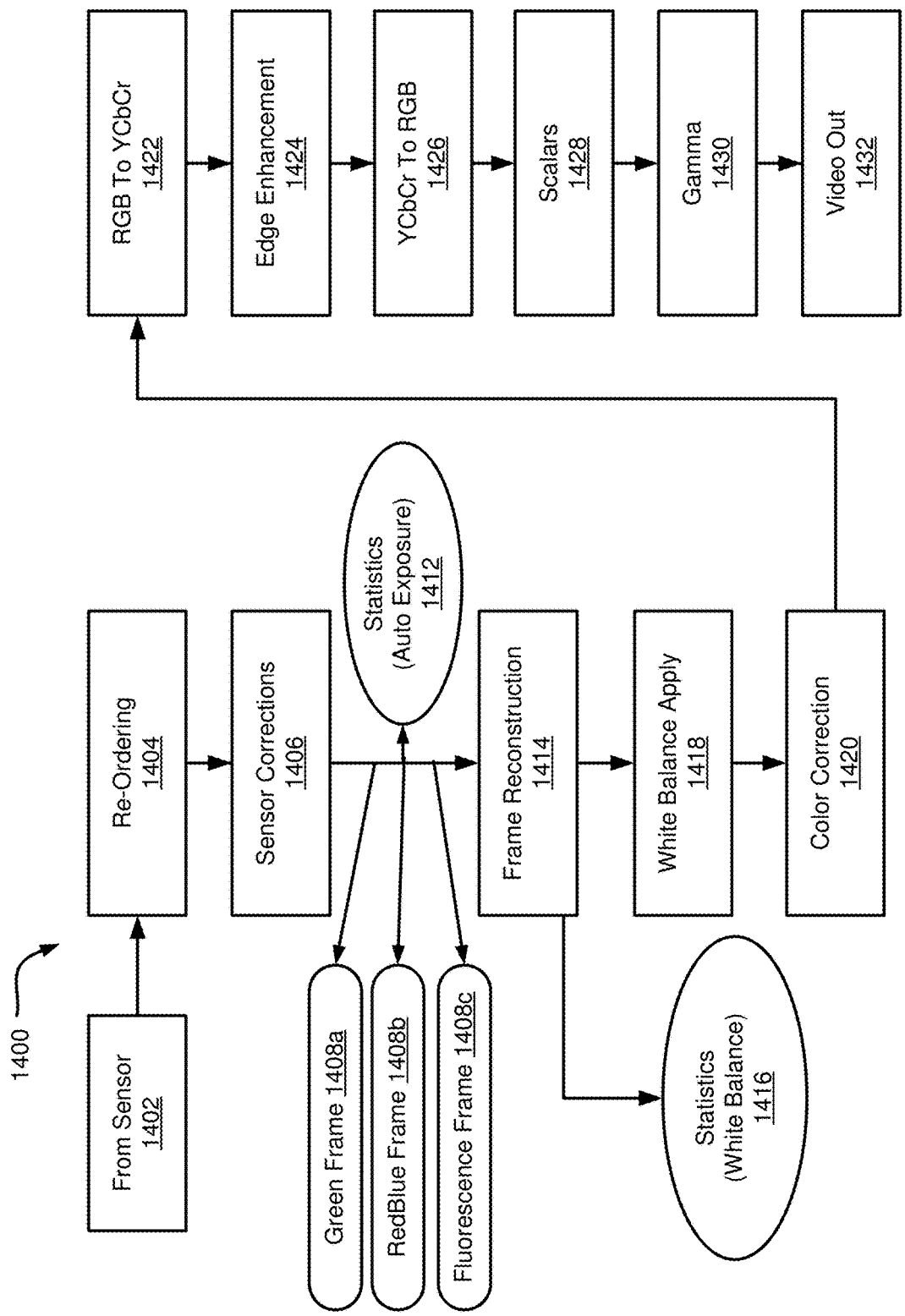
FIG. 14 is a schematic diagram of a process flow to be implemented by a controller and/or monochrome image signal processor for generating a video stream having RGB images with fluorescence data overlaid thereon.

FIG. 14 illustrates a process flow 1400 to be implemented by a controller and/or monochrome image signal processor (ISP) for generating a video stream having RGB images with fluorescence data overlaid thereon. The image signal processor (ISP) chain may be assembled for the purpose of generating sRGB image sequences from raw sensor data, yielded in the presence of the G-R-G-B-Fluorescence light pulsing scheme. In the process flow 1400, the first stage is concerned with making corrections (see receiving data from the sensor at 1402, re-ordering at 1404, and sensor corrections at 1406 in FIG. 14) to account for any non-idealities in the sensor technology for which it is most appropriate to work in the raw data domain. At the next stage, multiple frames (for example, a green frame 1408a, a red-blue frame 1408b, and a fluorescence frame 1408c) are buffered because each final frame derives data from multiple raw frames. The frame reconstruction at 1264 proceeds by sampling data from a current frame and two buffered frames (see 1408a, 1408b, and/or 1408c). The reconstruction process results in full color frames in linear RGB color space that include fluorescence image data. In this example, the white balance coefficients at 1418 and color correction matrix at 1420 are applied before converting to YCbCr space at 1422 for subsequent edge enhancement at 1424. After edge enhancement at 1424, images are transformed back to linear RGB at 1426 for scaling at 1428, if applicable. Finally, the gamma transfer function at 1430 is applied to translate the data into the sRGB domain at 1432.

Figure 15:
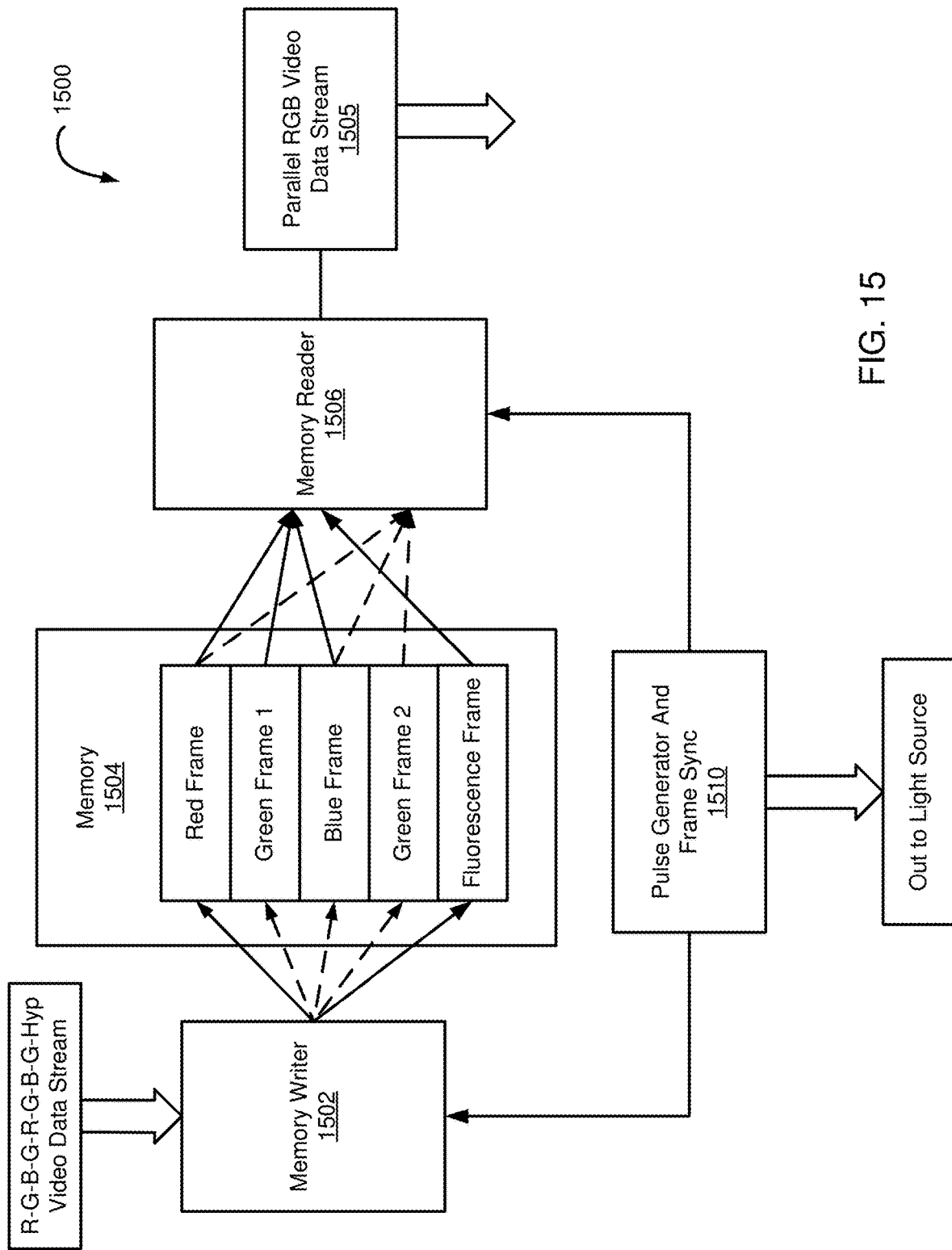
FIG. 15 is a schematic diagram of method and hardware schematics for use with a partitioned light system.

FIG. 15 is an example of color fusion hardware 1500. The color fusion hardware 1500 stores in memory 1504 an R-G-B-G-Fluorescence video data stream with a memory writer 1502 and converts the video data stream to a parallel RGB+Fluorescence video data stream at 1505. The bit width on the input side may be, e.g., 12 bits per color. The output width for that example would be at least 36 bits per pixel. Other embodiments may have different initial bit widths and 3+ times that number for the output width. The memory writer 1502 block takes as its input the RGBG-Fluorescence video stream and writes each frame to its correct frame memory 1504 (the memory writer triggers off the same pulse generator (see 2510) that runs the laser light source). The memory 1504 may store exposure frame data in a pattern such as the one illustrated, namely: Red, Green 1, Blue, Green 2, Fluorescence and then starts back with Red again. The memory reader 1506 reads three frames at once to construct an RGB pixel. Each pixel is three times the bit width of an individual color component. The memory reader 1506 also triggers off the laser pulse generator at 2510. In an embodiment, the memory reader 1506 waits until Red, Green 1 and Blue frames have been written, then proceeds to read them out in parallel while the writer continues writing Green 2, Fluorescence, and starts back on Red. When Red completes the reader begins reading from Blue, Green 2, Fluorescence, and Red. This pattern continues indefinitely.

Figure 16:
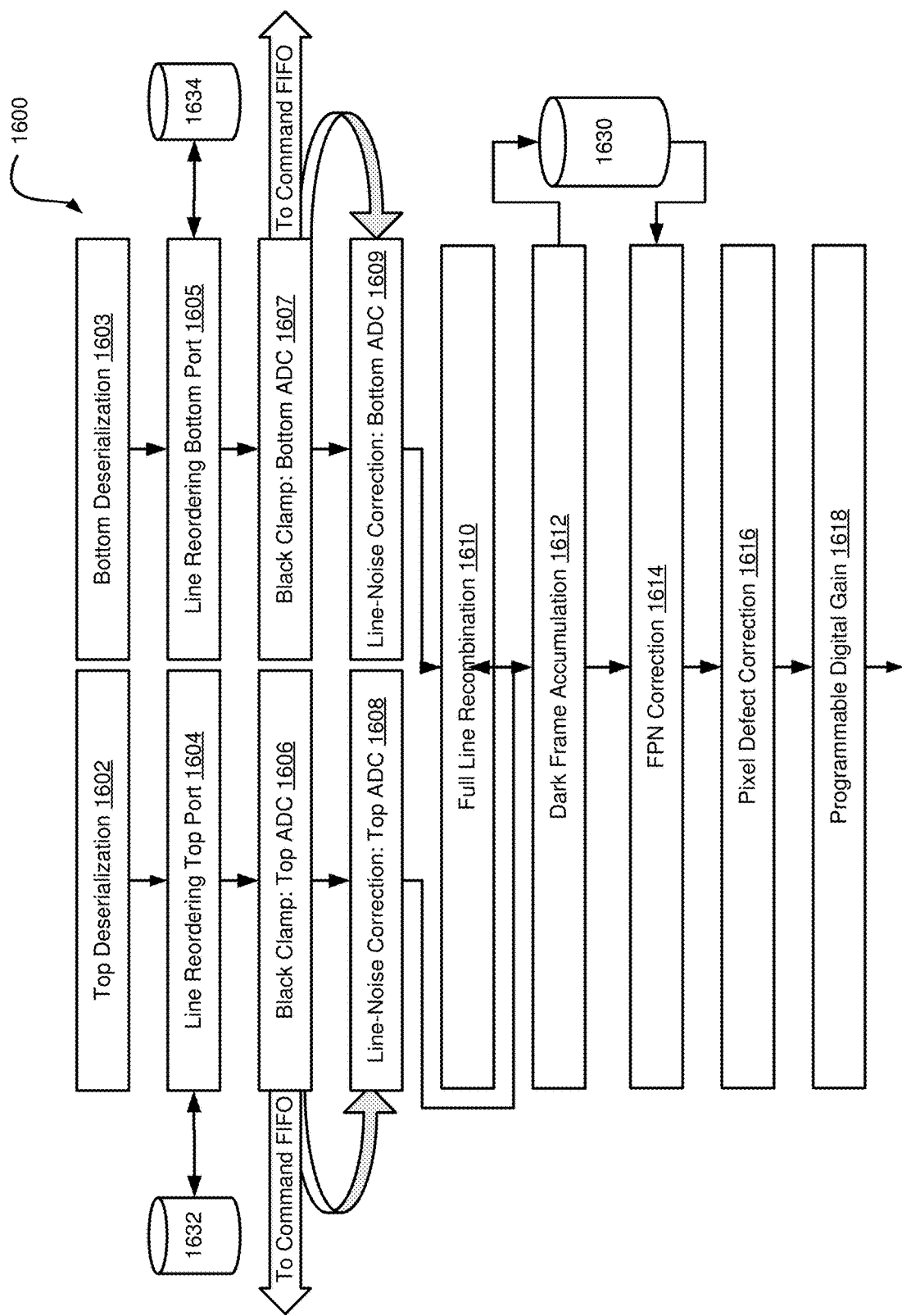
FIG. 16 is a schematic diagram of a process flow for performing corrections and adjustments on digital image data.

FIG. 16 is a schematic diagram of a process flow 1600 for sensor correction processes. The process flow 1600 is an example implementation of the front end of an image signal process that has been developed in the context of a system incorporating a minimal area image sensor. In the example process flow 1600, there are two digitizers on the sensor converting the even and odd-numbered columns respectively and transmitting serial data on two differential ports. The process flow 1600 may be employed in a color and fluorescence pulsed system as discussed herein. The process flow 1600 may be employed to counteract non-idealities in CMOS image sensors such as fixed pattern noise (FPN) and line noise. Fixed pattern noise is a dispersion in the offsets of the sense elements. Typically, most of the FPN is a pixel to pixel dispersion which stems from random variations in dark current from photodiode to photodiode. The systems disclosed herein maintain complete control of the illumination source, and this enables dark data to be acquired and used to correct for the pixel and column offsets. In the illustrated example, a single frame buffer may be used to make a running average of the whole frame without light using, e.g., simple exponential smoothing. This dark average frame may be subtracted from every illuminated frame during regular operation. Line noise is a stochastic temporal variation in the offsets of pixels within each row. Because line noise is temporal, the correction is computed for each line and each frame. For this purpose, there are usually many optically blind (OB) pixels within each row in a pixel array. The OB pixels must first be sampled to assess the line offset before sampling the light sensitive pixels. The line offset is then subtracted during the line noise correction process.

The process flow 1600 includes performing top deserialization 1602 and bottom deserialization 1603. The process flow 1600 includes performing line reordering at the top port at 1604 and line reordering at the bottom port at 1605. The information may be stored in separate databases 1632, 1634 or other memory devices upon the completion of line reordering. The process flow 1600 includes performing a black clamp calculation on the top ADC at 1606 and a black clamp calculation on the bottom ADC at 1607. The information exits the process flow 1600 on a first-in-first-out (FIFO) basis. The process flow 1600 includes performing line noise correction at the top ADC at 1608 and line noise correction at the bottom ADC at 1609. The process flow 1600 includes performing full line recombination at 1610 and dark frame accumulation at 1612. The information may be stored in a database 1630 or other memory device before fixed pattern noise (FPN) correction is performed. The process flow includes performing fixed pattern noise (FPN) correction at 1614 and pixel defect correction at 1616. The process flow 1600 includes performing programmable digital gain at 1618 before a video stream exits the process flow 1600 to be provided to a user.

Individual optical black pixels which do not behave normally may badly degrade the quality of the black offset measurements. An approach disclosed herein includes computing the media of a group of five pixels for each optical black pixel. The five pixels include the pixel in question and its four nearest neighbors. The final line offset estimate may then be computed as the mean of all the medians. In an embodiment, some provisions are made to avoid losing statistics at the beginning and the end. Such provisions include buffering the whole sample of optical blacks and wrapping around the sample of five. Buffering necessitates pipelining the data and results in a delay equal to at least the total number of optical blacks per analog to digital converter channel, per row.

The line offset estimate for an even channel (assuming two analog to digital converters with odd-even interspersion), row # r can be computed as follows:

$$L_{r,even} = \frac{2 \cdot \sum_{i=0,2,4...}^{N_{OB}-2} \mu_i}{N_{OB}}$$

The line offset where $N_{OB}$ may be the total number of optical black pixels per row and $\mu_i$ may be the median for optical black pixel i, computed thus:

$$\mu_0 = \text{median}[x_{(N_{OB}-4)}, x_{(N_{OB}-2)}, x_0, x_2, x_4]$$
$$\mu_2 = \text{median}[x_{(N_{OB}-2)}, x_0, x_2, x_4, x_6]$$
$$\mu_4 = \text{median}[x_0, x_2, x_4, x_6, x_8]$$
$$\ldots$$
$$\mu_{(N_{OB}-2)} = \text{median}[x_{(N_{OB}-6)}, x_{(N_{OB}-4)}, x_{(N_{OB}-2)}, x_0, x_2]$$

Likewise, the line offset estimate for an odd channel (assuming two analog to digital converters with odd-even interspersion), row # r can be computed as follows:

$$L_{r,odd} = \frac{2 \cdot \sum_{i=1,3,5...}^{N_{OB}-1} \mu_i}{N_{OB}}$$

where $$\mu_1 = \text{median}[x_{(N_{OB}-3)}, x_{(N_{OB}-1)}, x_1, x_3, x_5]$$
$$\mu_3 = \text{median}[x_{(N_{OB}-1)}, x_1, x_3, x_5, x_7]$$
$$\mu_5 = \text{median}[x_1, x_3, x_5, x_7, x_9]$$
$$\ldots$$
$$\mu_{(N_{OB}-1)} = \text{median}[x_{(N_{OB}-5)}, x_{(N_{OB}-3)}, x_{(N_{OB}-1)}, x_1, x_3]$$

The overall frame black level may be computed by accumulating each of the line offsets to compute the overall black level. In this approach, the overall black level is determined using simple exponential smoothing (SES). Simple exponential smoothing allows the rows at the end of the frame to have a greater influence on the final black estimate. This may be desirable in certain implementations for addressing changes in black offset occurring on sub-frame timescales. The simple exponential smoothing algorithm determines a running estimate that may be incrementally adjusted each time a sample is made available. For convenience the sample can be divided by a binary number ($2^q$) before being added to the previous estimate. The previous estimate may be first multiplied by $(2^q-1)/2^q$ each time, in order to normalize the result. High values of q result in greater statistical precision over time in a stable scenario. Lower values of q may make the correction more reactive to rapid changes. q should be made available as a tunable parameter. This may be computed as follows:

$$k_r = L_r(r=0)$$

$$k_r = L_r \ (r = 0)$$
$$k_r = \frac{1}{2^q} L_r + \frac{(2^q - 1)}{2^q} k_{(r-1)} \ (r > 0)$$

where $k_r$ is the black level estimate after row r and $L_r$ may be the line offset estimate for row r. The decision about what to do with the black clamp digital to analog converters may be made after the final row in the array has been added.

The black clamp algorithm at 1606, 1607 may require a target black level, and this can be provided by an adjustable parameter. The black clamp digital to analog converter on the sensor for the channel in question would be pushed up or down depending on whether the observed black estimate may be above or below the target. The size of the push could be the smallest unit, i.e. one digital to analog converter count, provided the black offset may be close to the target. In the case that the black level may be a long way from the target, a larger proportional push could be made. The algorithm would need to know a rough calibration of the correspondence between black clamp digital to analog converter counts and sensor analog to digital converter counts and the directionality of digital to analog converter adjustments with respect to the output black level.

The line noise is corrected at 1608 and 1609. Line noise refers to stochastic, temporal variations in the offset of a horizontal row of pixels. There may be multiple sources, but it can be considered as reset noise arising from analog elements being reset each time a row of pixels is read out. It may be temporal, and a new correction should be computed for each new line per every frame. Since the amplification stage at the analog to digital converter input may be the final analog element, there may be good reason to suspect that the line noise appears phenomenologically independent per analog to digital converter channel. One approach is to correct each analog to digital converter channel separately.

It can be challenging to completely eliminate line noise because the sample of optical black pixels used for the line offset estimate may be separate from the sample to which the correction may be applied. The sample statistics are finite. Assuming the noise is Gaussian, the post-correction line noise may be approximately equal to the uncertainty in the line offset estimate arising from the pixel temporal noise present in the optical black pixels:

$$\sigma_{L,post} \approx \frac{\sigma_P}{\sqrt{N_{OB}}}$$

where $\sigma_{L,post}$ is the post correction temporal line noise, $\sigma_p$ is optical black pixel temporal noise, and $N_{OB}$ is the number of optical black pixels. The line noise correction also intro duces a spatial line noise component, mostly as a consequence of the pixel fixed pattern noise present within the optical black pixels:

$$FPN_{L,post} \approx \frac{FPN_P}{\sqrt{N_{OB}}}$$

This artifact can be eliminated by the fixed pattern noise correction later in the chain. Simulations have indicated that in order for temporal line noise to be invisible, the magnitude should be less than approximately 1/10 of the pixel temporal noise.

Line-noise correction application to optically sighted (clear) pixels:

$$x'_i = x_i - L + B$$

where L is the line offset estimate for the current line, ported from the 'Black Clamp' module and B is the black clamp target level.

Full line recombination at 1610 includes combining the two data channels (i.e., the top data channel and the bottom data channel) into a full line. The top and bottom data channels need to be interleaved in such a way that the final clear pixel order reflects the correct order in the array.

The fixed pattern noise correction at 1614 includes adjusting a running offset estimate on a per physical pixel basis. CMOS image sensors have multiple noise sources. The magnitude and appearance of noise depends on a range of physical conditions. Pure Poisson or Gaussian temporal noise with no coherent components (e.g. photon shot noise or source follower 1/f read noise) looks as natural as noise can look. All other perceivable noise types may degrade the image quality to a greater extent for the same amplitude. Spatial noise (fixed pattern noise) may be especially damaging and CMOS sensors inherently have at least two sources. CMOS image sensors experience pixel fixed pattern noise and column fixed pattern noise. The pixel fixed pattern noise may be mostly due to variations in photodiode leakage current (dark signal) from pixel to pixel (DSNU). This source may be exponentially dependent on junction temperature ($T_j$) and linearly dependent on exposure time. Column fixed pattern noise may be a consequence of the readout architecture, in which pixels from within the same column are channeled through common analog readout elements.

Typically, an on-chip digital fixed pattern noise correction involves dealing only with the column fixed pattern noise component and requires one offset correction register per column. The precision of such a correction might typically be 20 bits or so per column, which translates to around 5 kB of RAM for a 1920×1080 array. One of the benefits of migrating the digital sensor corrections to the image signal processor may be the ready availability of RAM. This opens up the possibility of a comprehensive fixed pattern noise correction which cancels out any row, column or pixel-wise component. This may be accomplished by means of simple exponential smoothing (SES) in which each fresh dark frame sample may be used to adjust a running offset estimate on a per physical pixel basis.

The programmable digital gain 1618 may be executed by a programmable digital amplifier. CMOS image sensors are usually equipped with digital programmable gain stages with very fine increments. This may be to facilitate auto exposure processes which typically modulate the gain and the exposure time. The programmable digital amplifier can be used to align the range of the sensor analog to digital converter to the range of the image signal processor (e.g. ×2 for 11 bit analog to digital converter to 12-bit image signal processor). A small amount of digital gain may also be used to trim off the imprint of the digital line noise and fixed pattern noise corrections which becomes apparent at the full range of the analog to digital converter.

A more space conservative approach involves combining large amounts of control RAM into single, long registers. In the extreme case, all parameters could be placed into a single register, requiring no address ROM. This solution may be not very practical because writing control registers takes time and typical video applications involve changing a small number of operational parameters on a frame-by-frame basis. The most practical solution may be afforded by concatenating functionally related sets of parameters into a small number of long registers. The difference in space implied by having ten registers (requiring 4 address bits) versus one may be negligible. In particular it makes sense that all of the parameters which are written periodically at a high rate belong together in an exclusive register (the frame register), in order to keep the time required to write it to a minimum. Such parameters include the exposure times, gains, incremental offset adjustments and any others necessary to maintain continuous high-quality video. If the digital data-path logic has been migrated off chip as described earlier, the black clamp voltage adjustment data also belongs in such a register since it should be revised every frame too. In an implementation, during this configuration phase can registers be written and therefore the timing of the frame register writes with respect to the overall frame timing should be carefully controlled by the camera.

Other examples of parametric register groupings could include; analog currents, analog voltages, pixel timing, vertical timing, sensor commands (resets etc.) and so on. In FIG. 15, the arrangement of registers may be shown for a specific minimal-area sensor design. The "Command" register may be used for top level event-oriented 1-bit commands such as chip resets and the loads for the other registers shown below it. A 2-wire protocol address decoder decides which shift register to direct incoming 2-wire protocol data toward. To load the "Format" register, e.g., the external controller sends a command with the address associated with the Format register. This places the stream of data into the Format-register shift register. Then in order to latch the data, a follow up command may be sent to the Command register with the particular "load Format" bit set. It will be appreciated that a plurality of control registers may be used. The control registers may be digital latches that may be loaded via shift registers. The shift registers may be arbitrary in length. In an embodiment, a majority of the plurality of control registers may be loaded using shift registers that include many tens of bits. In an embodiment, a majority of the plurality of control registers may be loaded using shift registers that include hundreds of bits. In an embodiment, a majority of the plurality of control registers may be loaded using shift registers that include thousands of bits. In an embodiment, the shift registers may be loaded using a serial, 2-wire protocol. In an embodiment, one of the shift registers may be dedicated to frame-to-frame parameter changes, such as, e.g., integration times and black clamp offset adjustments.

Figure 17:
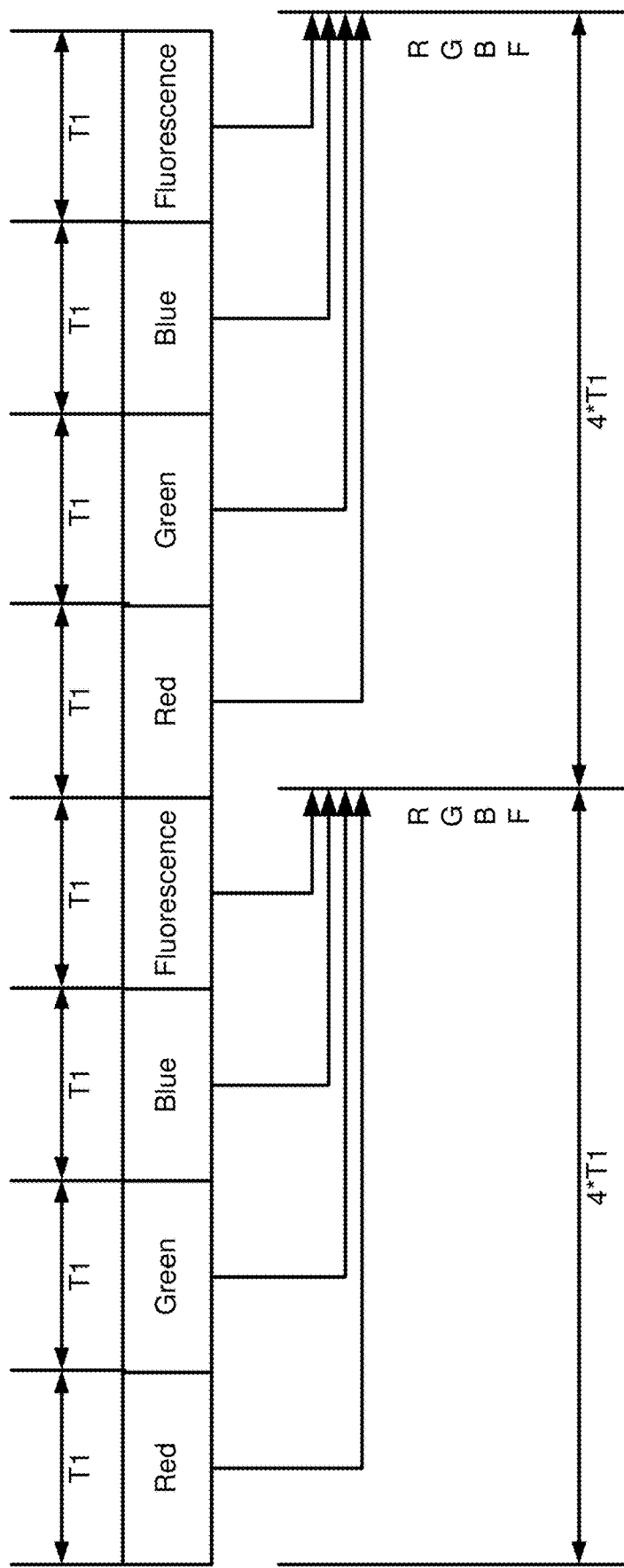
FIG. 17 is a schematic diagram of a pattern reconstruction process for generating an RGB image with fluorescence data overlaid thereon by pulsing partitioned spectrums of light.

FIG. 17 is a schematic diagram of a pattern reconstruction process. The example pattern illustrated in FIG. 17 includes Red, Green, Blue, and Fluorescence pulses of light that each last a duration of T1. In various embodiments, the pulses of light may be of the same duration or of differing durations.

The Red, Green, Blue, and Fluorescence exposure frames are combined to generate an RGB image with fluorescence data overlaid thereon. A single image frame comprising a red exposure frame, a green exposure frame, a blue exposure frame, and a fluorescence exposure frame requires a time period of 4*T1 to be generated. The time durations shown in FIG. 17 are illustrative only and may vary for different implementations. In other embodiments, different pulsing schemes may be employed. For example, embodiments may be based on the timing of each color component or frame (T1) and the reconstructed frame having a period twice that of the incoming color frame (2×T1). Different frames within the sequence may have different frame periods and the average capture rate could be any multiple of the final frame rate.

In an embodiment, the dynamic range of the system is increased by varying the pixel sensitivities of pixels within the pixel array of the image sensor. Some pixels may sense reflected electromagnetic radiation at a first sensitivity level, other pixels may sense reflected electromagnetic radiation at a second sensitivity level, and so forth. The different pixel sensitivities may be combined to increase the dynamic range provided by the pixel configuration of the image sensor. In an embodiment, adjacent pixels are set at different sensitivities such that each cycle includes data produced by pixels that are more and less sensitive with respect to each other. The dynamic range is increased when a plurality of sensitivities are recorded in a single cycle of the pixel array. In an embodiment, wide dynamic range can be achieved by having multiple global TX, each TX firing only on a different set of pixels. For example, in global mode, a global TX1 signal is firing a set 1 of pixels, a global TX2 signal is firing a set 2 of pixel, a global TXn signal is firing a set n of pixels, and so forth.

Figure 18A:
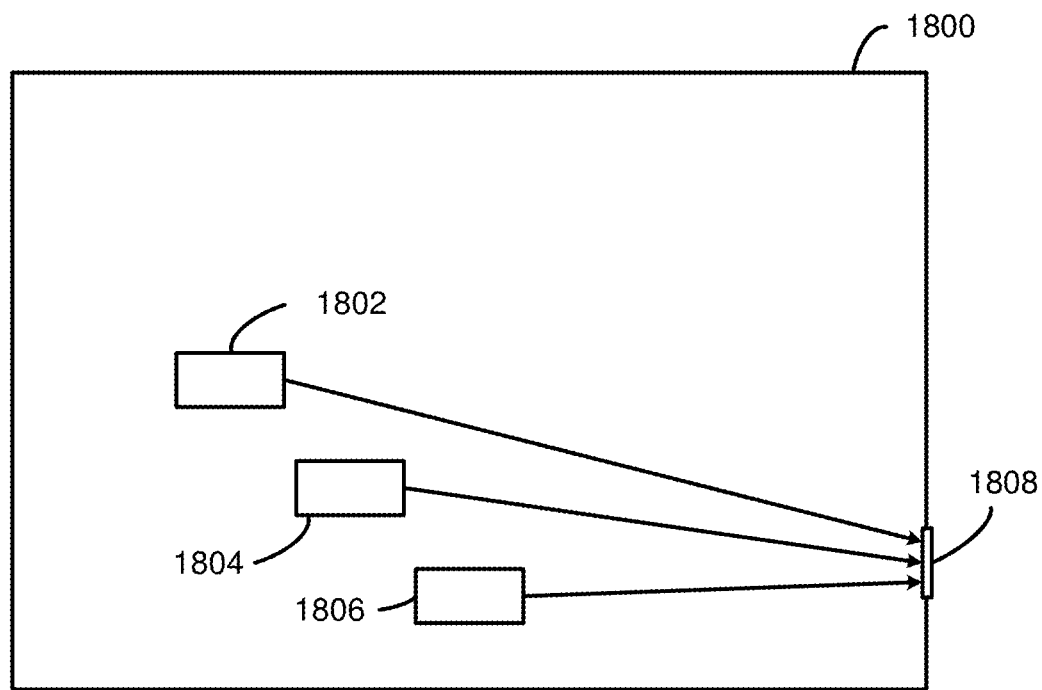
FIGS. 18A-18C illustrate a light source having a plurality of emitters.
Figure 18B:
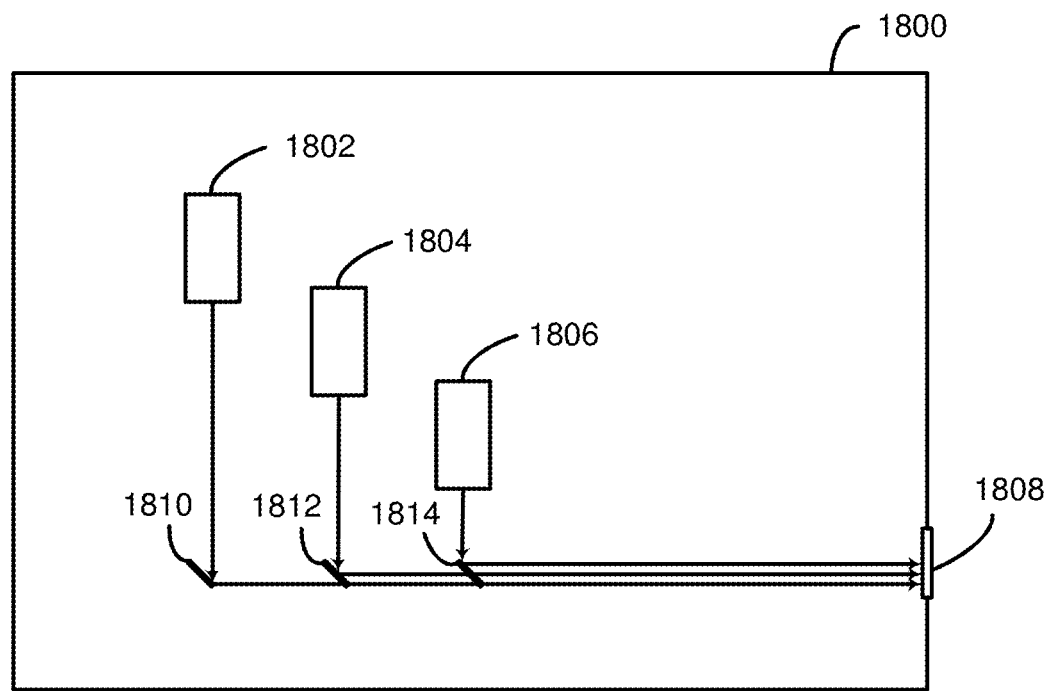
Figure 18C:
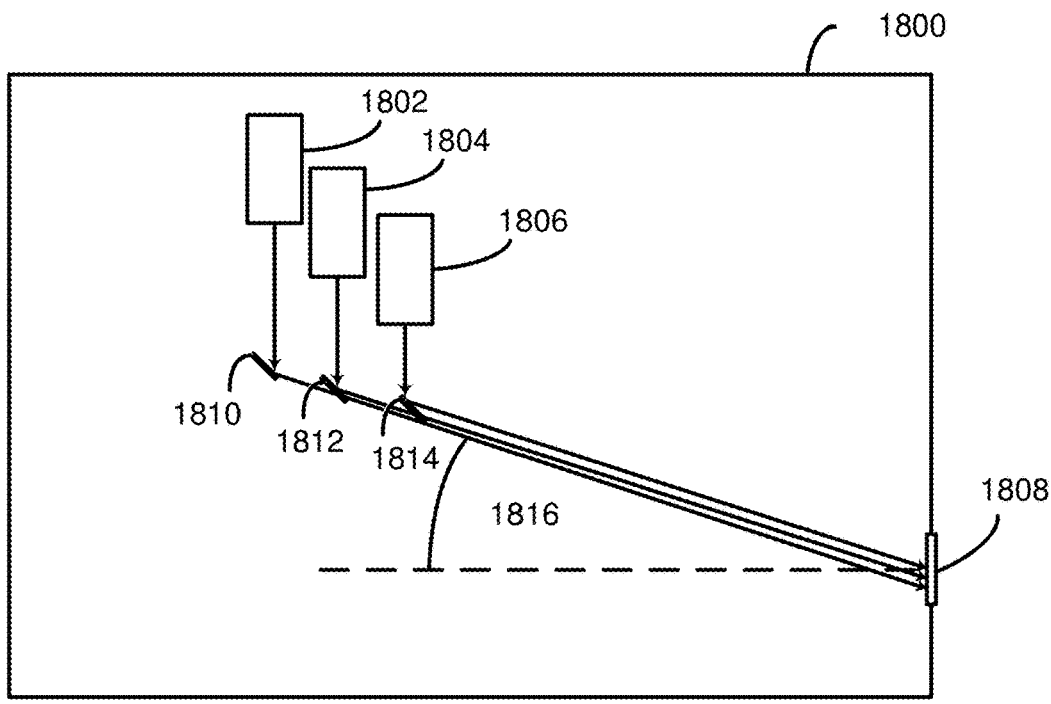

FIGS. 18A-18C each illustrate a light source 1800 having a plurality of emitters. The emitters include a first emitter 1802, a second emitter 1804, and a third emitter 1806. Additional emitters may be included, as discussed further below. The emitters 1802, 1804, and 1806 may include one or more laser emitters that emit light having different wavelengths. For example, the first emitter 1802 may emit a wavelength that is consistent with a blue laser, the second emitter 1804 may emit a wavelength that is consistent with a green laser, and the third emitter 1806 may emit a wavelength that is consistent with a red laser. For example, the first emitter 1802 may include one or more blue lasers, the second emitter 1804 may include one or more green lasers, and the third emitter 1806 may include one or more red lasers. The emitters 1802, 1804, 1806 emit laser beams toward a collection region 1808, which may be the location of a waveguide, lens, or other optical component for collecting and/or providing light to a waveguide, such as the jumper waveguide 206 or lumen waveguide 210 of FIG. 2.

In an implementation, the emitters 1802, 1804, and 1806 emit hyperspectral wavelengths of electromagnetic radiation. Certain hyperspectral wavelengths may pierce through tissue and enable a medical practitioner to "see through" tissues in the foreground to identify chemical processes, structures, compounds, biological processes, and so forth that are located behind the tissues in the foreground. The hyperspectral wavelengths may be specifically selected to identify a specific disease, tissue condition, biological process, chemical process, type of tissue, and so forth that is known to have a certain spectral response.

In an implementation where a patient has been administered a reagent or dye to aid in the identification of certain tissues, structures, chemical reactions, biological processes, and so forth, the emitters 1802, 1804, and 1806 may emit wavelength(s) for fluorescing the reagents or dyes. Such wavelength(s) may be determined based on the reagents or dyes administered to the patient. In such an embodiment, the emitters may need to be highly precise for emitting desired wavelength(s) to fluoresce or activate certain reagents or dyes.

In an implementation, the emitters 1802, 1804, and 1806 emit a laser scanning pattern for mapping a topology of a scene and/or for calculating dimensions and distances between objects in the scene. In an embodiment, the endoscopic imaging system is used in conjunction with multiple tools such as scalpels, retractors, forceps, and so forth. In such an embodiment, each of the emitters 1802, 1804, and 1806 may emit a laser scanning pattern such that a laser scanning pattern is projected on to each tool individually. In such an embodiment, the laser scanning data for each of the tools can be analyzed to identify distances between the tools and other objects in the scene.

In the embodiment of FIG. 18B, the emitters 1802, 1804, 1806 each deliver laser light to the collection region 1808 at different angles. The variation in angle can lead to variations where electromagnetic energy is located in an output waveguide. For example, if the light passes immediately into a fiber bundle (glass or plastic) at the collection region 1808, the varying angles may cause different amounts of light to enter different fibers. For example, the angle may result in intensity variations across the collection region 1808. Furthermore, light from the different emitters may not be homogenously mixed so some fibers may receive different amounts of light of different colors. Variation in the color or intensity of light in different fibers can lead to non-optimal illumination of a scene. For example, variations in delivered light or light intensities may result at the scene and captured images.

In one embodiment, an intervening optical element may be placed between a fiber bundle and the emitters 1802, 1804, 1806 to mix the different colors (wavelengths) of light before entry into the fibers or other waveguide. Example intervening optical elements include a diffuser, mixing rod, one or more lenses, or other optical components that mix the light so that a given fiber receive a same amount of each color (wavelength). For example, each fiber in the fiber bundle may have a same color. This mixing may lead to the same color in each fiber but may, in some embodiments, still result in different total brightness delivered to different fibers. In one embodiment, the intervening optical element may also spread out or even out the light over the collection region so that each fiber carries the same total amount of light (e.g., the light may be spread out in a top hat profile). A diffuser or mixing rod may lead to loss of light.

Although the collection region 1808 is represented as a physical component in FIG. 18A, the collection region 1808 may simply be a region where light from the emitters 1802, 1804, and 1806 is delivered. In some cases, the collection region 1808 may include an optical component such as a diffuser, mixing rod, lens, or any other intervening optical component between the emitters 1802, 1804, 1806 and an output waveguide.

FIG. 18C illustrates an embodiment of a light source 1800 with emitters 1802, 1804, 1806 that provide light to the collection region 1808 at the same or substantially same angle. The light is provided at an angle substantially perpendicular to the collection region 1808. The light source 1800 includes a plurality of dichroic mirrors including a first dichroic mirror 1810, a second dichroic mirror 1812, and a third dichroic mirror 1814. The dichroic mirrors 1810, 1812, 1814 include mirrors that reflect a first wavelength of light but transmit (or are transparent to) a second wavelength of light. For example, the third dichroic mirror 1814 may reflect blue laser light provided by the third emitter, while being transparent to the red and green light provided by the first emitter 1802 and the second emitter 1804, respectively. The second dichroic mirror 1812 may be transparent to red light from the first emitter 1802, but reflective to green light from the second emitter 1804. If other colors or wavelengths are included dichroic mirrors may be selected to reflect light corresponding to at least one emitter and be transparent to other emitters. For example, the third dichroic mirror 1814 reflect the light form the third emitter 1806 but is to emitters "behind" it, such as the first emitter 1802 and the second emitter 1804. In embodiments where tens or hundreds of emitters are present, each dichroic mirror may be reflective to a corresponding emitter and emitters in front of it while being transparent to emitters behind it. This may allow for tens or hundreds of emitters to emit electromagnetic energy to the collection region 1808 at a substantially same angle.

Because the dichroic mirrors allow other wavelengths to transmit or pass through, each of the wavelengths may arrive at the collection region 1808 from a same angle and/or with the same center or focal point. Providing light from the same angle and/or same focal/center point can significantly improve reception and color mixing at the collection region 1808. For example, a specific fiber may receive the different colors in the same proportions they were transmitted/reflected by the emitters 1802, 1804, 1806 and mirrors 1810, 1812, 1814. Light mixing may be significantly improved at the collection region compared to the embodiment of FIG. 18B. In one embodiment, any optical components discussed herein may be used at the collection region 1808 to collect light prior to providing it to a fiber or fiber bundle.

FIG. 18C illustrates an embodiment of a light source 1800 with emitters 1802, 1804, 1806 that also provide light to the collection region 1808 at the same or substantially same angle. However, the light incident on the collection region 1808 is offset from being perpendicular. Angle 1816 indicates the angle offset from perpendicular. In one embodiment, the laser emitters 1802, 1804, 1806 may have cross sectional intensity profiles that are Gaussian. As discussed previously, improved distribution of light energy between fibers may be accomplished by creating a more flat or top-hat shaped intensity profile. In one embodiment, as the angle 1816 is increased, the intensity across the collection region 1808 approaches a top hat profile. For example, a top-hat profile may be approximated even with a non-flat output beam by increasing the angle 1816 until the profile is sufficiently flat. The top hat profile may also be accomplished using one or more lenses, diffusers, mixing rods, or any other intervening optical component between the emitters 1802, 1804, 1806 and an output waveguide, fiber, or fiber optic bundle.

Figure 19:
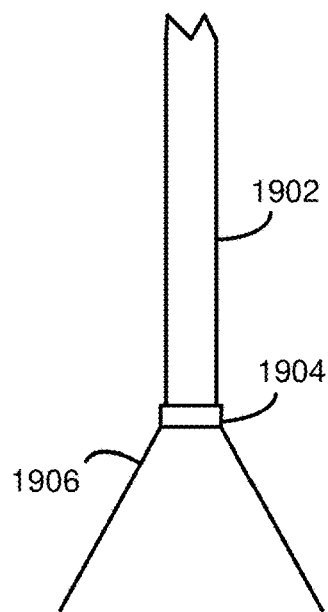
FIG. 19 illustrates a single optical fiber outputting via a diffuser at an output to illuminate a scene in a light deficient environment.

FIG. 19 is a schematic diagram illustrating a single optical fiber 1902 outputting via a diffuser 1904 at an output. In one embodiment, the optical fiber 1902 has a diameter of 500 microns, a numerical aperture of 0.65, and emits a light cone 1906 of about 70 or 80 degrees without a diffuser 1904. With the diffuser 1904, the light cone 1906 may have an angle of about 110 or 120 degrees. The light cone 1906 may be a majority of where all light goes and is evenly distributed. The diffuser 1904 may allow for more even distribution of electromagnetic energy of a scene observed by an image sensor.

In one embodiment, the lumen waveguide 210 includes a single plastic or glass optical fiber of about 500 microns. The plastic fiber may be low cost, but the width may allow the fiber to carry a sufficient amount of light to a scene, with coupling, diffusion, or other losses. For example, smaller fibers may not be able to carry as much light or power as a larger fiber. The lumen waveguide 210 may include a single or a plurality of optical fibers. The lumen waveguide 210 may receive light directly from the light source or via a jumper waveguide. A diffuser may be used to broaden the light output 206 for a desired field of view of the image sensor 214 or other optical components.

Although three emitters are shown in FIGS. 18A-18C, emitters numbering from one into the hundreds or more may be used in some embodiments. The emitters may have different wavelengths or spectrums of light that they emit, and which may be used to contiguously cover a desired portion of the electromagnetic spectrum (e.g., the visible spectrum as well as infrared and ultraviolet spectrums). The emitters may be configured to emit visible light such as red light, green light, and blue light, and may further be configured to emit hyperspectral emissions of electromagnetic radiation, fluorescence excitation wavelengths for fluorescing a reagent, and/or laser mapping patterns for calculating parameters and distances between objects in a scene.

Figure 20:
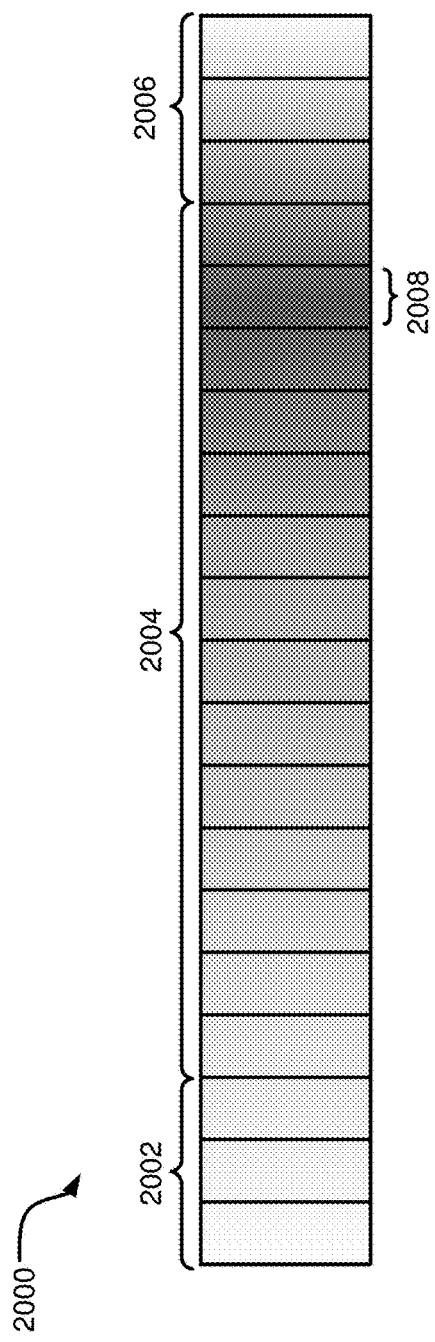
FIG. 20 illustrates a portion of the electromagnetic spectrum divided into a plurality of different sub-spectrums which may be emitted by emitters of a light source in accordance with the principles and teachings of the disclosure.

FIG. 20 illustrates a portion of the electromagnetic spectrum 2000 divided into twenty different sub-spectrums. The number of sub-spectrums is illustrative only. In at least one embodiment, the spectrum 2000 may be divided into hundreds of sub-spectrums, each with a small waveband. The spectrum may extend from the infrared spectrum 2002, through the visible spectrum 2004, and into the ultraviolet spectrum 2006. The sub-spectrums each have a waveband 2008 that covers a portion of the spectrum 2000. Each waveband may be defined by an upper wavelength and a lower wavelength.

Hyperspectral imaging includes imaging information from across the electromagnetic spectrum 2000. A hyperspectral pulse of electromagnetic radiation may include a plurality of sub-pulses spanning one or more portions of the electromagnetic spectrum 2000 or the entirety of the electromagnetic spectrum 2000. A hyperspectral pulse of electromagnetic radiation may include a single partition of wavelengths of electromagnetic radiation. A resulting hyperspectral exposure frame includes information sensed by the pixel array subsequent to a hyperspectral pulse of electromagnetic radiation. Therefore, a hyperspectral exposure frame may include data for any suitable partition of the electromagnetic spectrum 2000 and may include multiple exposure frames for multiple partitions of the electromagnetic spectrum 2000. In an embodiment, a hyperspectral exposure frame includes multiple hyperspectral exposure frames such that the combined hyperspectral exposure frame comprises data for the entirety of the electromagnetic spectrum 2000.

In one embodiment, at least one emitter (such as a laser emitter) is included in a light source (such as the light sources 202, 1800) for each sub-spectrum to provide complete and contiguous coverage of the whole spectrum 2000. For example, a light source for providing coverage of the illustrated sub-spectrums may include at least 20 different emitters, at least one for each sub-spectrum. In one embodiment, each emitter covers a spectrum covering 40 nanometers. For example, one emitter may emit light within a waveband from 500 nm to 540 nm while another emitter may emit light within a waveband from 540 nm to 580 nm. In another embodiment, emitters may cover other sizes of wavebands, depending on the types of emitters available or the imaging needs. For example, a plurality of emitters may include a first emitter that covers a waveband from 500 to 540 nm, a second emitter that covers a waveband from 540 nm to 640 nm, and a third emitter that covers a waveband from 640 nm to 650 nm. Each emitter may cover a different slice of the electromagnetic spectrum ranging from far infrared, mid infrared, near infrared, visible light, near ultraviolet and/or extreme ultraviolet. In some cases, a plurality of emitters of the same type or wavelength may be included to provide sufficient output power for imaging. The number of emitters needed for a specific waveband may depend on the sensitivity of a monochrome sensor to the waveband and/or the power output capability of emitters in that waveband.

The waveband widths and coverage provided by the emitters may be selected to provide any desired combination of spectrums. For example, contiguous coverage of a spectrum using very small waveband widths (e.g., 10 nm or less) may allow for highly selective hyperspectral and/or fluorescence imaging. The waveband widths may allow for selectively emitting the excitation wavelength(s) for one or more particular fluorescent reagents. Additionally, the waveband widths may allow for selectively emitting certain partitions of hyperspectral electromagnetic radiation for identifying specific structures, chemical processes, tissues, biological processes, and so forth. Because the wavelengths come from emitters which can be selectively activated, extreme flexibility for fluorescing one or more specific fluorescent reagents during an examination can be achieved. Additionally, extreme flexibility for identifying one or more objects or processes by way of hyperspectral imaging can be achieved. Thus, much more fluorescence and/or hyperspectral information may be achieved in less time and within a single examination which would have required multiple examinations, delays because of the administration of dyes or stains, or the like.

Figure 21:
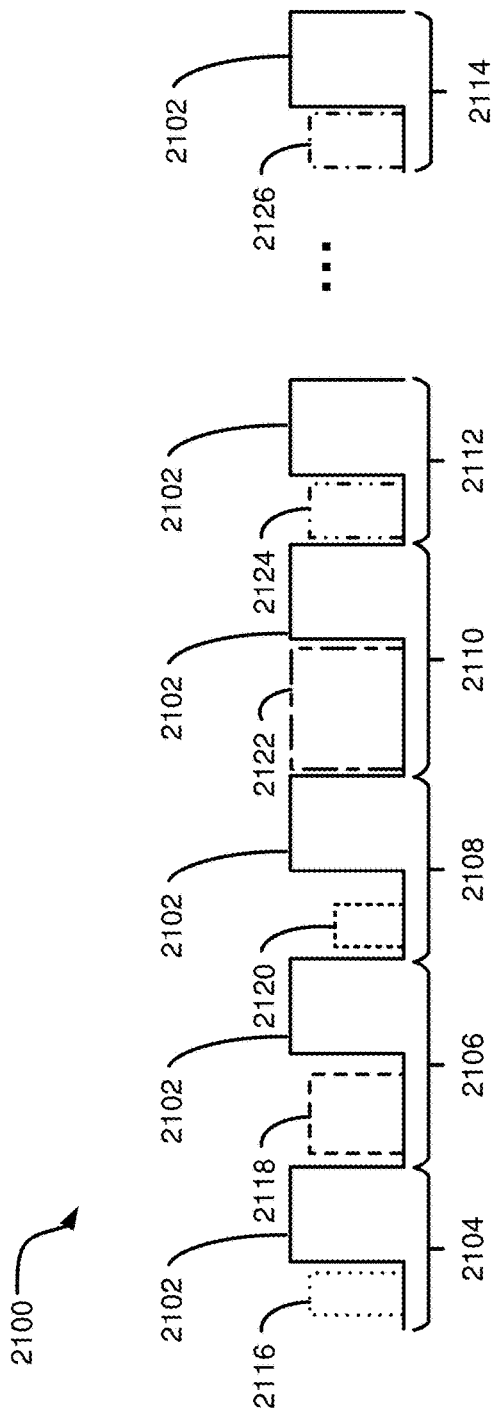
FIG. 21 is a schematic diagram illustrating a timing sequence for emission and readout for generating an image frame comprising a plurality of exposure frames resulting from differing partitions of pulsed light.

FIG. 21 is a schematic diagram illustrating a timing diagram 2100 for emission and readout for generating an image. The solid line represents readout (peaks 2102) and blanking periods (valleys) for capturing a series of exposure frames 2104-2114. The series of exposure frames 2104-2114 may include a repeating series of exposure frames which may be used for generating laser scanning, hyperspectral, and/or fluorescence data that may be overlaid on an RGB video stream. In an embodiment, a single image frame comprises information from multiple exposure frames, wherein one exposure frame includes red image data, another exposure frame includes green image data, and another exposure frame includes blue image data. Additionally, the single image frame may include one or more of hyperspectral image data, fluorescence image data, and laser scanning data. The multiple exposure frames are combined to produce the single image frame. The single image frame is an RGB image with hyperspectral imaging data. The series of exposure frames include a first exposure frame 2104, a second exposure frame 2106, a third exposure frame 2108, a fourth exposure frame 2110, a fifth exposure frame 2112, and an Nth exposure frame 2126.

Additionally, the hyperspectral image data, the fluorescence image data, and the laser scanning data can be used in combination to identify critical tissues or structures and further to measure the dimensions of those critical tissues or structures. For example, the hyperspectral image data may be provided to a corresponding system to identify certain critical structures in a body such as a nerve, ureter, blood vessel, cancerous tissue, and so forth. The location and identification of the critical structures may be received from the corresponding system and may further be used to generate topology of the critical structures using the laser scanning data. For example, a corresponding system determines the location of a cancerous tumor based on hyperspectral imaging data. Because the location of the cancerous tumor is known based on the hyperspectral imaging data, the topology and distances of the cancerous tumor may then be calculated based on laser scanning data. This example may also apply when a cancerous tumor or other structure is identified based on fluorescence imaging data.

In one embodiment, each exposure frame is generated based on at least one pulse of electromagnetic energy. The pulse of electromagnetic energy is reflected and detected by an image sensor and then read out in a subsequent readout (2102). Thus, each blanking period and readout results in an exposure frame for a specific spectrum of electromagnetic energy. For example, the first exposure frame 2104 may be generated based on a spectrum of a first one or more pulses 2116, a second exposure frame 2106 may be generated based on a spectrum of a second one or more pulses 2118, a third exposure frame 2108 may be generated based on a spectrum of a third one or more pulses 2120, a fourth exposure frame 2110 may be generated based on a spectrum of a fourth one or more pulses 2122, a fifth exposure frame 2112 may be generated based on a spectrum of a fifth one or more pulses 2124, and an Nth exposure frame 2126 may be generated based on a spectrum of an Nth one or more pulses 2126.

The pulses 2116-2126 may include energy from a single emitter or from a combination of two or more emitters. For example, the spectrum included in a single readout period or within the plurality of exposure frames 2104-2114 may be selected for a desired examination or detection of a specific tissue or condition. According to one embodiment, one or more pulses may include visible spectrum light for generating an RGB or black and white image while one or more additional pulses are emitted to sense a spectral response to a fluorescence wavelength of electromagnetic radiation. For example, pulse 2116 may include red light, pulse 2118 may include blue light, and pulse 2120 may include green light while the remaining pulses 2122-2126 may include wavelengths and spectrums for detecting a specific tissue type, fluorescing a reagent, and/or mapping the topology of the scene. As a further example, pulses for a single readout period include a spectrum generated from multiple different emitters (e.g., different slices of the electromagnetic spectrum) that can be used to detect a specific tissue type. For example, if the combination of wavelengths results in a pixel having a value exceeding or falling below a threshold, that pixel may be classified as corresponding to a specific type of tissue. Each frame may be used to further narrow the type of tissue that is present at that pixel (e.g., and each pixel in the image) to provide a very specific classification of the tissue and/or a state of the tissue (diseased/healthy) based on a spectral response of the tissue and/or whether a fluorescent reagent is present at the tissue.

The plurality of frames 2104-2114 is shown having varying lengths in readout periods and pulses having different lengths or intensities. The blanking period, pulse length or intensity, or the like may be selected based on the sensitivity of a monochromatic sensor to the specific wavelength, the power output capability of the emitter(s), and/or the carrying capacity of the waveguide.

In one embodiment, dual image sensors may be used to obtain three-dimensional images or video feeds. A three-dimensional examination may allow for improved understanding of a three-dimensional structure of the examined region as well as a mapping of the different tissue or material types within the region.

In an example implementation, a fluorescent reagent is provided to a patient, and the fluorescent reagent is configured to adhere to cancerous cells. The fluorescent reagent is known to fluoresce when radiated with a specific partition of electromagnetic radiation. The relaxation wavelength of the fluorescent reagent is also known. In the example implementation, the patient is imaged with an endoscopic imaging system as discussed herein. The endoscopic imaging system pulses partitions of red, green, and blue wavelengths of light to generate an RGB video stream of the interior of the patient's body. Additionally, the endoscopic imaging system pulses the excitation wavelength of electromagnetic radiation for the fluorescent reagent that was administered to the patient. In the example, the patient has cancerous cells and the fluorescent reagent has adhered to the cancerous cells. When the endoscopic imaging system pulses the excitation wavelength for the fluorescent reagent, the fluorescent reagent will fluoresce and emit a relaxation wavelength. If the cancerous cells are present in the scene being imaged by the endoscopic imaging system, then the fluorescent reagent will also be present in the scene and will emit its relaxation wavelength after fluorescing due to the emission of the excitation wavelength. The endoscopic imaging system senses the relaxation wavelength of the fluorescent reagent and thereby senses the presence of the fluorescent reagent in the scene. Because the fluorescent reagent is known to adhere to cancerous cells, the presence of the fluorescent reagent further indicates the presence of cancerous cells within the scene. The endoscopic imaging system thereby identifies the location of cancerous cells within the scene. The endoscopic imaging system may further emit a laser scanning pulsing scheme for generating a topology of the scene and calculating dimensions for objects within the scene. The location of the cancerous cells (as identified by the fluorescence imaging data) may be combined with the topology and dimensions information calculated based on the laser scanning data. Therefore, the precise location, size, dimensions, and topology of the cancerous cells may be identified. This information may be provided to a medical practitioner to aid in excising the cancerous cells. Additionally, this information may be provided to a robotic surgical system to enable the surgical system to excise the cancerous cells.

In a further example implementation, a patient is imaged with an endoscopic imaging system to identify quantitative diagnostic information about the patient's tissue pathology. In the example, the patient is suspected or known to suffer from a disease that can be tracked with hyperspectral imaging to observe the progression of the disease in the patient's tissue. The endoscopic imaging system pulses partitions of red, green, and blue wavelengths of light to generate an RGB video stream of the interior of the patient's body. Additionally, the endoscopic imaging system pulses one or more hyperspectral wavelengths of light that permit the system to "see through" some tissues and generate imaging of the tissue that is affected by the disease. The endoscopic imaging system senses the reflected hyperspectral electromagnetic radiation to generate hyperspectral imaging data of the diseased tissue, and thereby identifies the location of the diseased tissue within the patient's body. The endoscopic imaging system may further emit a laser scanning pulsing scheme for generating a topology of the scene and calculating dimensions of objects within the scene. The location of the diseased tissue (as identified by the hyperspectral imaging data) may be combined with the topology and dimensions information that is calculated with the laser scanning data. Therefore, the precise location, size, dimensions, and topology of the diseased tissue can be identified. This information may be provided to a medical practitioner to aid in excising, imaging, or studying the diseased tissue. Additionally, this information may be provided to a robotic surgical system to enable the surgical system to excise the diseased tissue.

Figure 22:
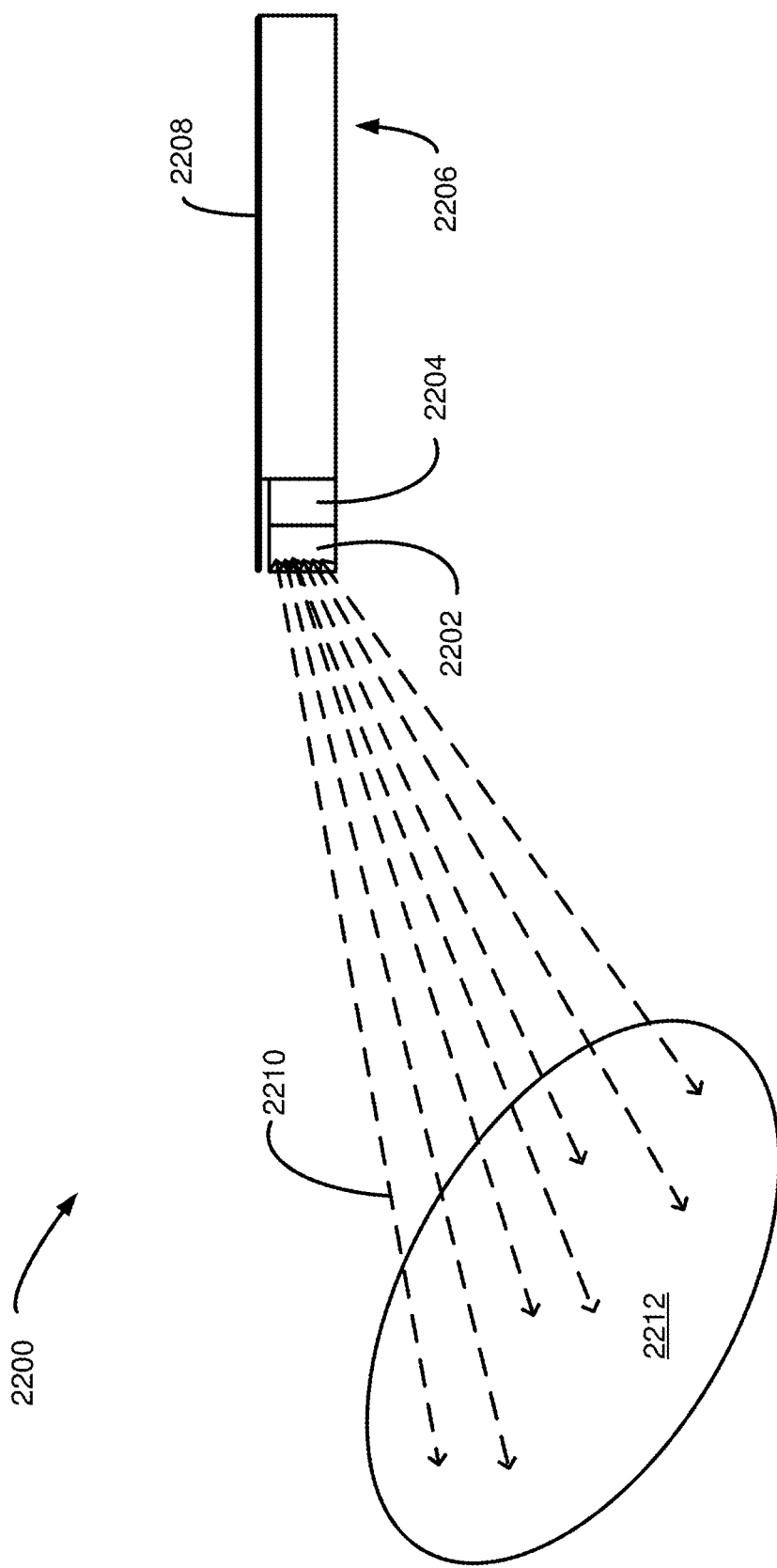
FIG. 22 illustrates an imaging system including a single cut filter for filtering wavelengths of electromagnetic radiation.

FIG. 22 is a schematic diagram of an imaging system 2200 having a single cut filter. The system 2200 includes an endoscope 2206 or other suitable imaging device having a light source 2208 for use in a light deficient environment. The endoscope 2206 includes an image sensor 2204 and a filter 2202 for filtering out unwanted wavelengths of light or other electromagnetic radiation before reaching the image sensor 2204. The light source 2208 transmits light that may illuminate the surface 2212 in a light deficient environment such as a body cavity. The light 2210 is reflected off the surface 2212 and passes through the filter 2202 before hitting the image sensor 2204.

The filter 2202 may be used in an implementation where a fluorescent reagent or dye has been administered. In such an embodiment, the light source 2208 emits the excitation wavelength for fluorescing the fluorescent reagent or dye. Commonly, the relaxation wavelength emitted by the fluorescent reagent or dye will be of a different wavelength than the excitation wavelength. The filter 2202 may be selected to filter out the excitation wavelength and permit only the relaxation wavelength to pass through the filter and be sensed by the image sensor 2204.

In one embodiment, the filter 2202 is configured to filter out an excitation wavelength of electromagnetic radiation that causes a reagent or dye to fluoresce such that only the expected relaxation wavelength of the fluoresced reagent or dye is permitted to pass through the filter 2202 and reach the image sensor 2204. In an embodiment, the filter 2202 filters out at least a fluorescent reagent excitation wavelength between 770 nm and 790 nm. In an embodiment, the filter 2202 filters out at least a fluorescent reagent excitation wavelength between 795 nm and 815 nm. In an embodiment, the filter 2202 filters out at least a fluorescent reagent excitation wavelength between 770 nm and 790 nm and between 795 nm and 815 nm. In these embodiments, the filter 2202 filters out the excitation wavelength of the reagent and permits only the relaxation wavelength of the fluoresced reagent to be read by the image sensor 2204. The image sensor 2204 may be a wavelength-agnostic image sensor and the filter 2202 may be configured to permit the image sensor 2204 to only receive the relaxation wavelength of the fluoresced reagent and not receive the emitted excitation wavelength for the reagent. The data determined by the image sensor 2204 may then indicate a presence of a critical body structure, tissue, biological process, or chemical process as determined by a location of the reagent or dye.

The filter 2202 may further be used in an implementation where a fluorescent reagent or dye has not been administered. The filter 2202 may be selected to permit wavelengths corresponding to a desired spectral response to pass through and be read by the image sensor 2204. The image sensor 2204 may be a monochromatic image sensor such that pixels of the captured image that exceed a threshold or fall below a threshold may be characterized as corresponding to a certain spectral response or fluorescence emission. The spectral response or fluorescence emission, as determined by the pixels captured by the image sensor 2204, may indicate the presence of a certain body tissue or structure, a certain condition, a certain chemical process, and so forth.

Figure 23:
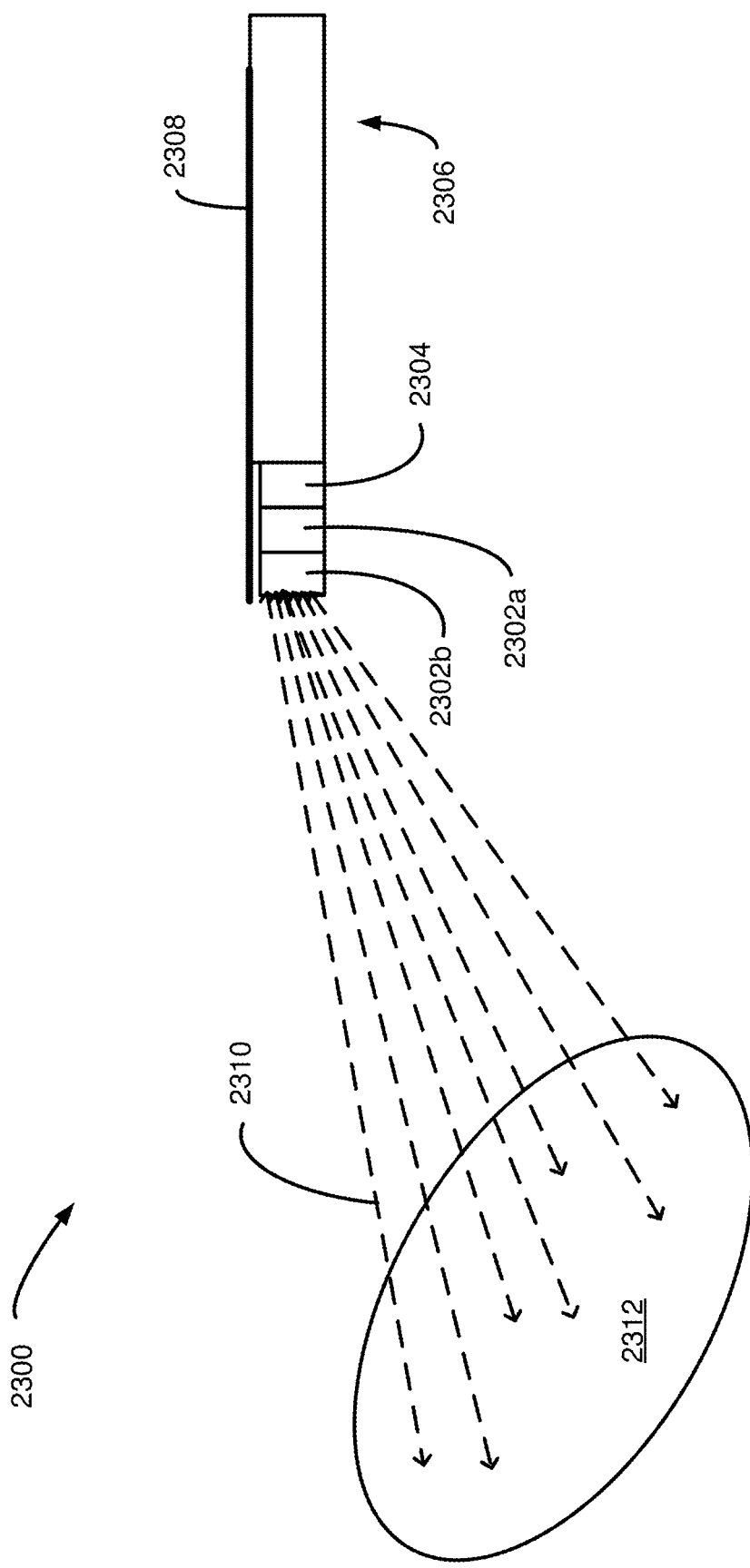
FIG. 23 illustrates an imaging system comprising a multiple cut filter for filtering wavelengths of electromagnetic radiation.

FIG. 23 is a schematic diagram of an imaging system 2300 having multiple cut filters. The system 2300 includes an endoscope 2306 or other suitable imaging device having a light source 2308 for use in a light deficient environment. The endoscope 2306 includes an image sensor 2304 and two filters 2302a, 2302b. It should be appreciated that in alternative embodiments, the system 2300 may include any number of filters, and the number of filters and the type of filters may be selected for a certain purpose e.g., for gathering imaging information of a particular body tissue, body condition, chemical process, and so forth. The filters 2302a, 2302b are configured for preventing unwanted wavelengths of light or other electromagnetic radiation from being sensed by the image sensor 2304. The filters 2302a, 2302b may be configured to filter out unwanted wavelengths from white light or other electromagnetic radiation that may be emitted by the light source 2308.

Further to the disclosure with respect to FIG. 22, the filters 2302a, 2302b may be used in an implementation where a fluorescent reagent or dye has been administered. The filters 2302a, 2302b may be configured for blocking an emitted excitation wavelength for the reagent or dye and permitting the image sensor 2304 to only read the relaxation wavelength of the reagent or dye. Further, the filters 2302a, 2302b may be used in an implementation where a fluorescent reagent or dye has not been administered. In such an implementation, the filters 2302a, 2302b may be selected to permit wavelengths corresponding to a desired spectral response to pass through and be read by the image sensor 2304.

The multiple filters 2302a, 2302b may each be configured for filtering out a different range of wavelengths of the electromagnetic spectrum. For example, one filter may be configured for filtering out wavelengths longer than a desired wavelength range and the additional filter may be configured for filtering out wavelengths shorter than the desired wavelength range. The combination of the two or more filters may result in only a certain wavelength or band of wavelengths being read by the image sensor 2304.

In an embodiment, the filters 2302a, 2302b are customized such that electromagnetic radiation between 513 nm and 545 nm contacts the image sensor 2304. In an embodiment, the filters 2302a, 2302b are customized such that electromagnetic radiation between 565 nm and 585 nm contacts the image sensor 2304. In an embodiment, the filters 2302a, 2302b are customized such that electromagnetic radiation between 900 nm and 1000 nm contacts the image sensor 2304. In an embodiment, the filters 2302a, 2302b are customized such that electromagnetic radiation between 425 nm and 475 nm contacts the image sensor 2304. In an embodiment, the filters 2302a, 2302b are customized such that electromagnetic radiation between 520 nm and 545 nm contacts the image sensor 2304. In an embodiment, the filters 2302a, 2302b are customized such that electromagnetic radiation between 625 nm and 645 nm contacts the image sensor 2304. In an embodiment, the filters 2302a, 2302b are customized such that electromagnetic radiation between 760 nm and 795 nm contacts the image sensor 2304. In an embodiment, the filters 2302a, 2302b are customized such that electromagnetic radiation between 795 nm and 815 nm contacts the image sensor 2304. In an embodiment, the filters 2302a, 2302b are customized such that electromagnetic radiation between 370 nm and 420 nm contacts the image sensor 2304. In an embodiment, the filters 2302a, 2302b are customized such that electromagnetic radiation between 600 nm and 670 nm contacts the image sensor 2304. In an embodiment, the filters 2302a, 2302b are configured for permitting only a certain fluorescence relaxation emission to pass through the filters 2302a, 2302b and contact the image sensor 2304.

In an embodiment, the system 2300 includes multiple image sensors 2304 and may particularly include two image sensors for use in generating a three-dimensional image. The image sensor(s) 2304 may be color/wavelength agnostic and configured for reading any wavelength of electromagnetic radiation that is reflected off the surface 2312. In an embodiment, the image sensors 2304 are each color dependent or wavelength dependent and configured for reading electromagnetic radiation of a particular wavelength that is reflected off the surface 2312 and back to the image sensors 2304. Alternatively, the image sensor 2304 may include a single image sensor with a plurality of different pixel sensors configured for reading different wavelengths or colors of light, such as a Bayer filter color filter array. Alternatively, the image sensor 2304 may include one or more color agnostic image sensors that may be configured for reading different wavelengths of electromagnetic radiation according to a pulsing schedule such as those illustrated in FIGS. 5-7E, for example.

FIGS. 24A and 24B illustrate a perspective view and a side view, respectively, of an implementation of an imaging sensor 2400 having a plurality of pixel arrays for producing a three-dimensional image. The three-dimensional image sensor may be built on a plurality of substrates and may comprise the plurality of pixel arrays and other associated circuitry, wherein a plurality of pixel columns 2404a forming the first pixel array and a plurality of pixel columns 2404b forming a second pixel array are located on respective substrates 2402a and 2402b, respectively, and a plurality of circuit columns 2408a and 2408b are located on a separate substrate 2406. Also illustrated are the electrical connections and communications between columns of pixels to associated or corresponding column of circuitry.

The plurality of pixel arrays may sense information simultaneously and the information from the plurality of pixel arrays may be combined to generate a three-dimensional image. In an embodiment, an endoscopic imaging system includes two or more pixel arrays that can be deployed to generate three-dimensional imaging. The endoscopic imaging system may include an emitter for emitting pulses of electromagnetic radiation during a blanking period of the pixel arrays. The pixel arrays may be synced such that the optical black pixels are read (i.e., the blanking period occurs) at the same time for the two or more pixel arrays. The emitter may emit pulses of electromagnetic radiation for charging each of the two or more pixel arrays. The two or more pixel arrays may read their respective charged pixels at the same time such that the readout periods for the two or more pixel arrays occur at the same time or at approximately the same time. In an embodiment, the endoscopic imaging system includes multiple emitters that are each individual synced with one or more pixel arrays of a plurality of pixel arrays. Information from a plurality of pixel arrays may be combined to generate three-dimensional image frames and video streams.

Figure 25A:
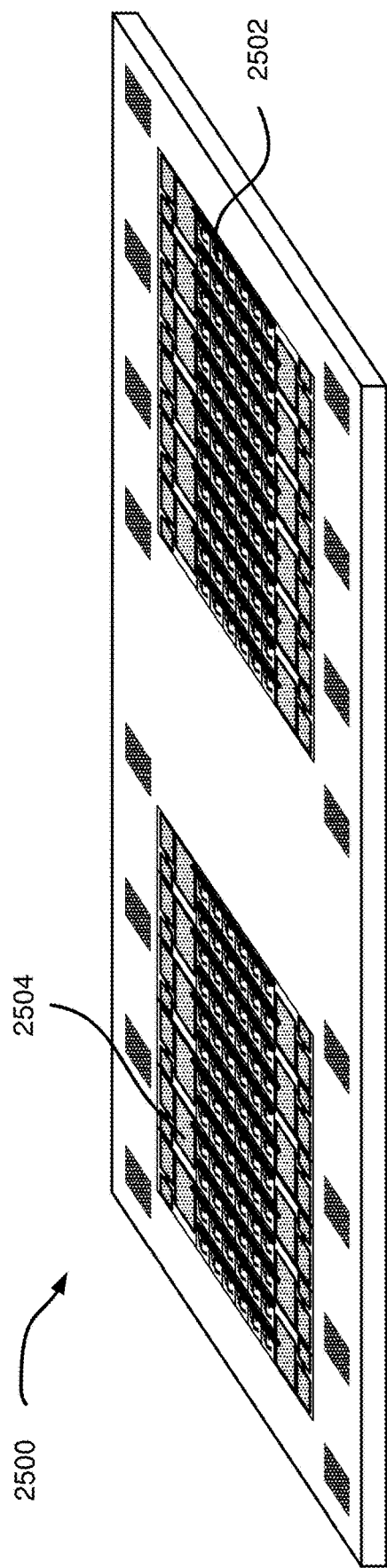
FIGS. 25A and 25B illustrate an implementation having a plurality of pixel arrays for producing a three-dimensional image in accordance with the principles and teachings of the disclosure.
Figure 25B:
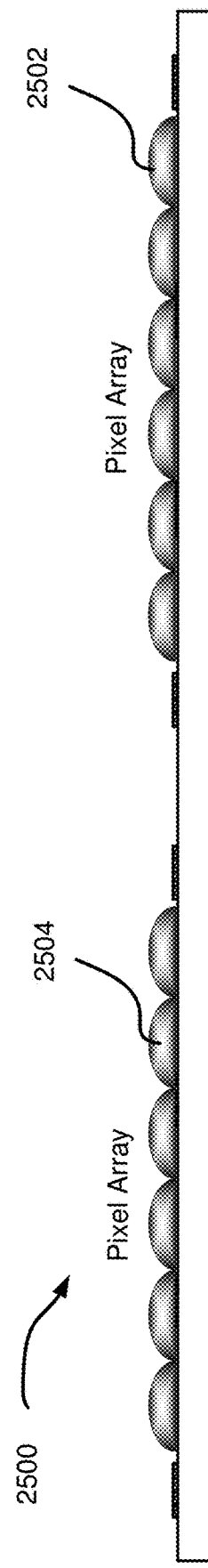

FIGS. 25A and 25B illustrate a perspective view and a side view, respectively, of an implementation of a monolithic sensor 2500 having a plurality of pixel arrays for producing a three-dimensional image in accordance with the teachings and principles of the disclosure. Such an implementation may be desirable for three-dimensional image capture, wherein the two-pixel arrays 2502 and 2504 may be offset during use. In another implementation, a first pixel array 2502 and a second pixel array 2504 may be dedicated to receiving a predetermined range of wave lengths of electromagnetic radiation, wherein the first pixel array is dedicated to a different range of wavelength electromagnetic radiation than the second pixel array.

Figure 26A:
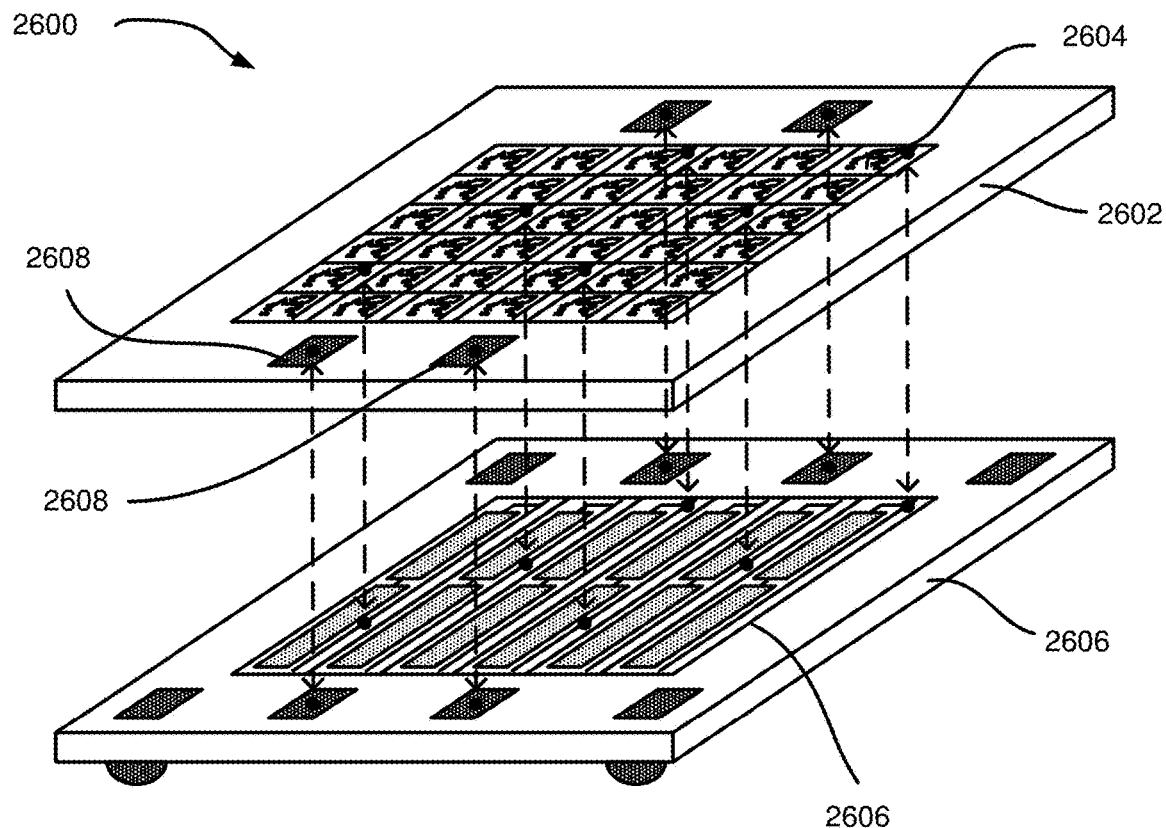
FIGS. 26A and 26B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 26B:
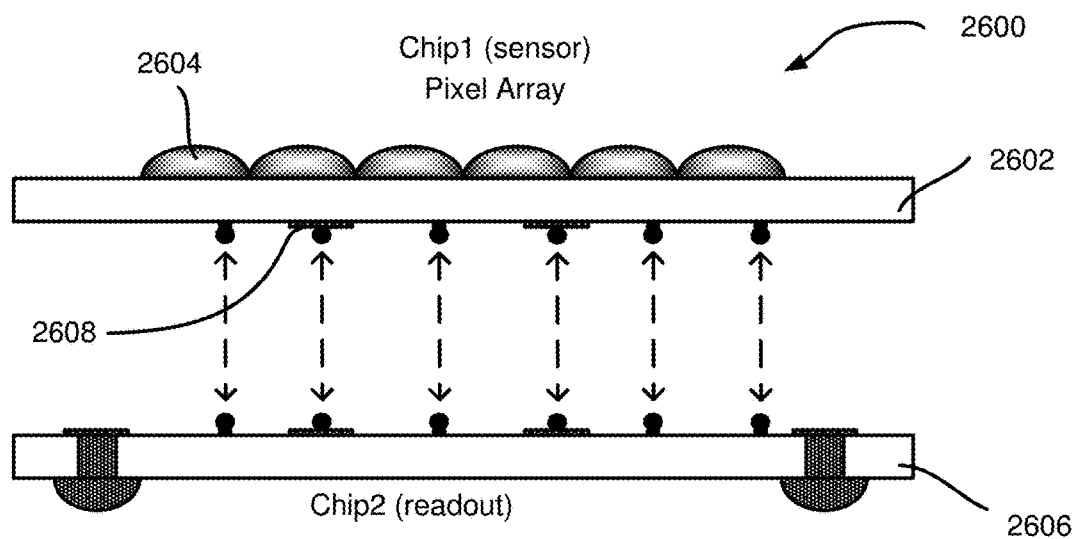

FIGS. 26A and 26B illustrate a perspective view and a side view, respectively, of an implementation of an imaging sensor 2600 built on a plurality of substrates. As illustrated, a plurality of pixel columns 2604 forming the pixel array are located on the first substrate 2602 and a plurality of circuit columns 2608 are located on a second substrate 2606. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 2602 of the two substrates/chips may be processed using an image CMOS process. The first substrate/chip 2602 may be comprised either of a pixel array exclusively or a pixel array surrounded by limited circuitry. The second or subsequent substrate/chip 2606 may be processed using any process and does not have to be from an image CMOS process. The second substrate/chip 2606 may be, but is not limited to, a highly dense digital process to integrate a variety and number of functions in a very limited space or area on the substrate/chip, or a mixed-mode or analog process to integrate for example precise analog functions, or a RF process to implement wireless capability, or MEMS (Micro-Electro-Mechanical Systems) to integrate MEMS devices. The image CMOS substrate/chip 2602 may be stacked with the second or subsequent substrate/chip 2606 using any three-dimensional technique. The second substrate/chip 2606 may support most, or a majority, of the circuitry that would have otherwise been implemented in the first image CMOS chip 2602 (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wire bonds, bump and/or TSV (Through Silicon Via).

It will be appreciated that the teachings and principles of the disclosure may be used in a reusable device platform, a limited use device platform, a re-posable use device platform, or a single use/disposable device platform without departing from the scope of the disclosure. It will be appreciated that in a re-usable device platform an end-user is responsible for cleaning and sterilization of the device. In a limited use device platform, the device can be used for some specified amount of times before becoming inoperable. Typical new device is delivered sterile with additional uses requiring the end-user to clean and sterilize before additional uses. In a re-posable use device platform, a third-party may reprocess the device (e.g., cleans, packages and sterilizes) a single-use device for additional uses at a lower cost than a new unit. In a single use/disposable device platform a device is provided sterile to the operating room and used only once before being disposed of.

EXAMPLES

The following examples pertain to preferred features of further embodiments:

Example 1 is a method. The method includes actuating an emitter to emit a plurality of pulses of electromagnetic radiation and sensing reflected electromagnetic radiation resulting from the plurality of pulses of electromagnetic radiation with a pixel array of an image sensor to generate a plurality of exposure frames. The method includes generating a reference frame for use in removing fixed pattern noise from the plurality of exposure frames, wherein the reference frame is based on dark frame data captured when the emitter is not emitting electromagnetic radiation. The method includes reducing fixed pattern noise in an exposure frame of the plurality of exposure frames by subtracting the reference frame from the exposure frame. The method is such that at least a portion of the plurality of pulses of electromagnetic radiation emitted by the emitter comprises one or more of electromagnetic radiation having a wavelength from about 770 nm to about 790 nm, or from about 795 nm to about 815 nm.

Example 2 is a method as in Example 1, further comprising: stopping the emitter from pulsing electromagnetic radiation; and sensing the dark frame data with the pixel array when the emitter is not emitting electromagnetic radiation.

Example 3 is a method as in any of Examples 1-2, wherein the plurality of pulses of electromagnetic radiation are emitted in a pattern of varying wavelengths of electromagnetic radiation, and wherein the emitter repeats the pattern of varying wavelengths of electromagnetic radiation.

Example 4 is a method as in any of Examples 1-3, wherein the pattern of varying wavelengths of electromagnetic radiation comprises a zero-emission period wherein the emitter does not pulse electromagnetic radiation, and wherein the method further comprises sensing the dark frame data with the pixel array during the zero-emission period.

Example 5 is a method as in any of Examples 1-4, further comprising sensing a plurality of dark exposure frames with the pixel array when the emitter is not emitting electromagnetic radiation, wherein each of the plurality of dark exposure frames comprises dark frame data.

Example 6 is a method as in any of Examples 1-5, wherein the plurality of dark exposure frames are interspersed within the plurality of exposure frames.

Example 7 is a method as in any of Examples 1-6, wherein generating the reference frame comprises generating a plurality of reference frames based on the plurality of dark exposure frames, and wherein the method further comprises enhancing precision of at least one reference frame of the plurality of reference frames by sampling subsequent dark frame data from subsequent dark exposure frames.

Example 8 is a method as in any of Examples 1-7, wherein enhancing precision of the at least one reference frame comprises accounting for the subsequent dark frame data from the subsequent dark exposure frames using exponential smoothing.

Example 9 is a method as in any of Examples 1-8, wherein generating the reference frame comprises interpolating two or more instances of dark frame data from two or more dark exposure frames captured at different integration times.

Example 10 is a method as in any of Examples 1-9, wherein sensing the reflected electromagnetic radiation comprises sensing during a readout period of the pixel array, wherein the readout period is a duration of time when active pixels in the pixel array are read.

Example 11 is a method as in any of Examples 1-10, wherein actuating the emitter comprises actuating the emitter to emit, during a pulse duration, a plurality of sub-pulses of electromagnetic radiation having a sub-duration shorter than the pulse duration.

Example 12 is a method as in any of Examples 1-11, wherein actuating the emitter comprises actuating the emitter to emit two or more wavelengths simultaneously as a single pulse or a single sub-pulse.

Example 13 is a method as in any of Examples 1-12, wherein sensing the reflected electromagnetic radiation comprises generating a fluorescence exposure frame, and wherein the method further comprises providing the fluorescence exposure frame to a corresponding system that determines a location of a critical tissue structure within a scene based on the fluorescence exposure frame.

Example 14 is a method as in any of Examples 1-13, further comprising: receiving the location of the critical tissue structure from the corresponding system; generating an overlay frame comprising the location of the critical tissue structure; and combining the overlay frame with a color image frame depicting the scene to indicate the location of the critical tissue structure within the scene.

Example 15 is a method as in any of Examples 1-14, wherein the critical tissue structure comprises one or more of a nerve, a ureter, a blood vessel, an artery, a blood flow, or a tumor.

Example 16 is a method as in any of Examples 1-15, further comprising synchronizing timing of the plurality of pulses of electromagnetic radiation to be emitted during a blanking period of the image sensor, wherein the blanking period corresponds to a time between a readout of a last row of active pixels in the pixel array and a beginning of a next subsequent readout of active pixels in the pixel array.

Example 17 is a method as in any of Examples 1-16, wherein sensing the reflected electromagnetic radiation comprises sensing with a first pixel array and a second pixel array such that a three-dimensional image can be generated based on the sensed reflected electromagnetic radiation.

Example 18 is a method as in any of Examples 1-17, wherein actuating the emitter comprises actuating the emitter to emit a sequence of pulses of electromagnetic radiation repeatedly sufficient for generating a video stream comprising a plurality of image frames, wherein each image frame in the video stream comprises data from a plurality of exposure frames, and wherein each of the exposure frames corresponds to a pulse of electromagnetic radiation.

Example 19 is a method as in any of Examples 1-18, wherein at least a portion of the plurality of pulses of electromagnetic radiation emitted by the emitter is an excitation wavelength for fluorescing a reagent, and wherein at least a portion of the reflected electromagnetic radiation sensed by the pixel array is a relaxation wavelength of the reagent.

Example 20 is a system. The system includes an emitter for emitting a plurality of pulses of electromagnetic radiation and an image sensor comprising a pixel array for sensing reflected electromagnetic radiation to generate a plurality of exposure frames. The system includes one or more processors configurable to execute instructions stored in non-transitory computer readable storage media. The instructions includes generating a reference frame for use in removing fixed pattern noise from the plurality of exposure frames, wherein the reference frame is based on dark frame data. The instructions includes reducing fixed pattern noise in an exposure frame of the plurality of exposure frames by subtracting the reference frame from the exposure frame. The system is such that at least a portion of the pulses of electromagnetic radiation emitted by the emitter comprises one or more of: electromagnetic radiation having a wavelength from about 770 nm to about 790 nm; or electromagnetic radiation having a wavelength from about 795 nm to about 815 nm.

Example 21 is a system as in Example 20, wherein the instructions further comprise: stopping the emitter from pulsing electromagnetic radiation; and sensing the dark frame data with the pixel array when the emitter is not emitting electromagnetic radiation.

Example 22 is a system as in any of Examples 20-21, wherein the plurality of pulses of electromagnetic radiation are emitted in a pattern of varying wavelengths of electromagnetic radiation, and wherein the emitter repeats the pattern of varying wavelengths of electromagnetic radiation.

Example 23 is a system as in any of Examples 20-22, wherein the pattern of varying wavelengths of electromagnetic radiation comprises a zero-emission period wherein the emitter does not pulse electromagnetic radiation, and wherein the method further comprises sensing the dark frame data with the pixel array during the zero-emission period.

Example 24 is a system as in any of Examples 20-23, wherein the pixel array senses a plurality of dark exposure frames over a plurality of instances when the emitter is not emitting electromagnetic radiation, wherein each of the plurality of dark exposure frames comprises dark frame data.

Example 25 is a system as in any of Examples 20-24, wherein the instructions are such that generating the reference frame comprises generating a plurality of reference frames based on the plurality of dark exposure frames, and wherein the method further comprises enhancing precision of at least one reference frame of the plurality of reference frames by sampling subsequent dark frame data from subsequent dark exposure frames.

Example 26 is a system as in any of Examples 20-25, wherein at least a portion of the pulses of electromagnetic radiation emitted by the emitter results in a fluorescence exposure frame created by the image sensor, and wherein the instructions further comprise providing the fluorescence exposure frame to a corresponding system that determines a location of a critical tissue structure within a scene based on the fluorescence exposure frame.

Example 27 is a system as in any of Examples 20-26, wherein the instructions further comprise: receiving the location of the critical tissue structure from the corresponding system; generating an overlay frame comprising the location of the critical tissue structure; and combining the overlay frame with a color image frame depicting the scene to indicate the location of the critical tissue structure within the scene.

Example 28 is a system as in any of Examples 20-27, wherein the critical tissue structure comprises one or more of a nerve, a ureter, a blood vessel, an artery, a blood flow, or a tumor.

Example 29 is a system as in any of Examples 20-28, wherein the image sensor comprises a first image sensor and a second image sensor such that the image sensor can generate a three-dimensional image.

Example 30 is a system as in any of Examples 20-29, further comprising a filter that filters electromagnetic radiation having a wavelength from about 770 nm to about 790 nm.

Example 31 is a system as in any of Examples 20-30, further comprising a filter that filters electromagnetic radiation having a wavelength from about 795 nm to about 815 nm.

Example 32 is a means for performing any of the methods depicted in Examples 1-19.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that any features of the above-described arrangements, examples, and embodiments may be combined in a single embodiment comprising a combination of features taken from any of the disclosed arrangements, examples, and embodiments.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A method comprising:
   actuating an emitter to emit a plurality of pulses of electromagnetic radiation;
   sensing reflected electromagnetic radiation resulting from the plurality of pulses of electromagnetic radiation with a pixel array of an image sensor to generate a plurality of exposure frames, wherein the plurality of exposure frames comprises a fluorescence exposure frame sensed in response to an emission of a fluorescence excitation wavelength of electromagnetic radiation for fluorescing a reagent;
   generating a reference frame for use in removing fixed pattern noise from the plurality of exposure frames, wherein the reference frame is based on dark frame data captured when the emitter is not emitting electromagnetic radiation; and
   reducing fixed pattern noise in an exposure frame of the plurality of exposure frames by subtracting the reference frame from the exposure frame;
   filtering electromagnetic radiation to prevent the image sensor from sensing the fluorescence excitation wavelength of electromagnetic radiation; and
   providing the fluorescence exposure frame to a corresponding system configured to determine a location of a tissue structure within a scene based on the fluorescence exposure frame;
   wherein at least a portion of the plurality of pulses of electromagnetic radiation emitted by the emitter comprises one or more of:
      electromagnetic radiation having a wavelength from 770 nm to 795 nm; or
      electromagnetic radiation having a wavelength from 790 nm to 815 nm.

2. The method of claim 1, further comprising: stopping the emitter from pulsing electromagnetic radiation; and sensing the dark frame data with the pixel array when the emitter is not emitting electromagnetic radiation.

3. The method of claim 1, wherein the plurality of pulses of electromagnetic radiation are emitted in a pattern of varying wavelengths of electromagnetic radiation, and wherein the emitter repeats the pattern of varying wavelengths of electromagnetic radiation.

4. The method of claim 3, wherein the pattern of varying wavelengths of electromagnetic radiation comprises a zero-emission period wherein the emitter does not pulse electromagnetic radiation, and wherein the method further comprises sensing the dark frame data with the pixel array during the zero-emission period.

5. The method of claim 1, further comprising sensing a plurality of dark exposure frames with the pixel array when the emitter is not emitting electromagnetic radiation, wherein each of the plurality of dark exposure frames comprises dark frame data.

6. The method of claim 5, wherein the plurality of dark exposure frames are interspersed within the plurality of exposure frames.

7. The method of claim 5, wherein generating the reference frame comprises generating a plurality of reference frames based on the plurality of dark exposure frames, and wherein the method further comprises enhancing precision of at least one reference frame of the plurality of reference frames by sampling subsequent dark frame data from subsequent dark exposure frames.

8. The method of claim 7, wherein enhancing precision of the at least one reference frame comprises accounting for the subsequent dark frame data from the subsequent dark exposure frames using exponential smoothing.

9. The method of claim 1, wherein generating the reference frame comprises interpolating two or more instances of dark frame data from two or more dark expsosure frames captured at different integration times.

10. The method of claim 1, wherein sensing the reflected electromagnetic radiation comprises sensing during a readout period of the pixel array, wherein the readout period is a duration of time when active pixels in the pixel array are read.

11. The method of claim 1, wherein actuating the emitter comprises actuating the emitter to emit, during a pulse duration, a plurality of sub-pulses of electromagnetic radiation having a sub-duratin shorter than the pulse duration.

12. The method of claim 1, wherein actuating the emitter comprises actuating the emitter to emit two or more wavelengths simultaneously as a single pulse or a single sub-pulse.

13. The method of claim 1, further comprising: receiving the location of the tissue structure from the corresponding system; generating an overlay frame comprising the location of the tissue structure; and combining the overlay frame with a color image frame depicting the scene to indicate the location of the tissue structure within the scene.

14. The method of claim 13, wherein the tissue structure comprises one or more of a nerve, a ureter, a blood vessel, an artery, a blood flow, or a tumor.

15. The method of claim 1, further comprising synchronizing timing of the plurality of pulses of electromagnetic radiation to be emitted during a blanking period of the image sensor, wherein the blanking period corresponds to a time between a readout of a last row of active pixels in the pixel array and a beginning of a next subsequent readout of active pixels in the pixel array.

16. The method of claim 1, wherein sensing the reflected electromagnetic radiation comprises sensing with a first pixel array and a second pixel array such that a three-dimensional image can be generated based on the sensed reflected electromagnetic radiation.

17. The method of claim 1, wherein actuating the emitter comprises actuating the emitter to emit a sequence of pulses of electromagnetic radiation repeatedly sufficient for generating a video stream comprising a plurality of image frames, wherein each image frame in the video stream comprises data from a plurality of exposure frames, and wherein each of the exposure frames corresponds to a pulse of electromagnetic radiation.

18. The method of claim 1, wherein at least a portion of the plurality of pulses of electromagnetic radiation emitted by the emitter is an excitation wavelength for fluorescing a reagnet, and wherein at least a portion of the reflected electromagnetic radiation sensed by the pixel array is a relaxation wavelength of the reagent.

19. A system comprising:
an emitter for emitting a plurality of pulses of electromagnetic radiation;
an image sensor comprising a pixel array for sensing reflected electromagnetic radiation to generate a plurality of exposure frames, wherein the plurality of exposure frames comprises a fluorescence exposure frame sensed in response to an emission of a fluorescence excitation wavelength of electromagnetic radiation for fluorescing a reagent; and
one or more processors configurable to execute instructions stored in non-transitory computer readable storage media, the instructions comprising:
generating a reference frame for use in removing fixed pattern noise from the plurality of exposure frames, wherein the reference frame is based on dark frame data captured when the emitter is not emitting electromagnetic radiation; and
reducing fixed pattern noise in an exposure frame of the plurality of exposure frames by subtracting the reference frame from the exposure frame;
filtering electromagnetic radiation to prevent the image sensor from sensing the fluorescence excitation wavelength of electromagnetic radiation; and
providing the fluorescence exposure frame to a corresponding system configured to determine a location of a tissue structure within a scene based on the fluorescence exposure frame;
wherein at least a portion of the pulses of electromagnetic radiation emitted by the emitter comprises one or more of:
electromagnetic radiation having a wavelength from about 770 nm to about 795 nm; or
electromagnetic radiation having a wavelength from about 790 nm to about 815 nm.

20. The system of claim 19, wherein the instructions further comprise: stopping the emitter from pulsing electromagnetic radiation; and sensing the dark frame data with the pixel array when the emitter is not emitting electromagnetic radiation.

21. The system of claim 19, wherein the plurality of pulses of electromagnetic radiation are emitted in a pattern of varying wavelengths of electromagnetic radiation, and wherein the emitter repeats the pattern of varying wavelengths of electromagnetic radiation.

22. The system of claim 21, wherein the pattern of varying wavelengths of electromagnetic radiation comprises a zero-emission period wherein the emitter does not pulse electromagnetic radiation, and wherein the instructions further comprise sensing the dark frame data with the pixel array during the zero-emission period.

23. The system of claim 19, wherein the pixel array senses a plurality of dark exposure frames over a plurality of instances when the emitter is not emitting electromagnetic radiation, wherein each of the plurality of dark exposure frames comprises dark frame data.

24. The system of claim 23, wherein the instructions are such that generating the reference frame comprises generating a plurality of reference frames based on the plurality of dark exposure frames, and wherein the instructions further comprise enhancing precision of at least one reference frame of the plurality of reference frames by sampling subsequent dark frame data from subsequent dark exposure frames.

25. The system of claim 19, wherein at least a portion of the pulses of electromagnetic radiation emitted by the emitter results in a fluorescence exposure frame created by the image sensor, and wherein the instructions further comprise providing the fluorescence exposure frame to a corresponding system that determines a location of a tissue structure within a scene based on the fluorescence exposure frame.

26. The system of claim 25, wherein the instructions further comprise: receiving the location of the tissue structure from the corresponding system; generating an overlay frame comprising the location of the tissue structure; and combining the overlay frame with a color image frame depicting the scene to indicate the location of the tissue structure within the scene.

27. The system of claim 26, wherein the tissue structure comprises one or more of a nerve, a ureter, a blood vessel, and artery, a blood flow, or a tumor.

28. The system of claim 19, wherein the image sensor comprises a first image sensor and a second image sensor such that the image sensor can generate a three-dimensional image.

29. The system of claim 23, further comprising a filter that filters electromagnetic radiation having a wavelength from about 770 nm to about 795 nm.

30. The system of claim 19, further comprising a filter that filters electromagnetic radiation having a wavelength from about 770 nm to about 815 nm.

* * * * *